(12) United States Patent
Fletcher

(10) Patent No.: US 9,242,944 B2
(45) Date of Patent: Jan. 26, 2016

(54) POTENT ANALOGUES OF THE C-MYC INHIBITOR 10074-G5 WITH IMPROVED CELL PERMEABILITY

(71) Applicant: UNIVERSITY OF MARYLAND, BALTIMORE, Baltimore, MD (US)

(72) Inventor: Steven Fletcher, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 14/227,243

(22) Filed: Mar. 27, 2014

(65) Prior Publication Data

US 2014/0296307 A1 Oct. 2, 2014

Related U.S. Application Data

(60) Provisional application No. 61/805,623, filed on Mar. 27, 2013, provisional application No. 61/866,763, filed on Aug. 16, 2013.

(51) Int. Cl.
C07D 271/12 (2006.01)

(52) U.S. Cl.
CPC .................................. *C07D 271/12* (2013.01)

(58) Field of Classification Search
CPC . A61K 31/4245; C07D 271/08; C07D 271/12
See application file for complete search history.

(56) References Cited

U.S. PATENT DOCUMENTS 8,637,556 B2   1/2014   Metallo et al.

FOREIGN PATENT DOCUMENTS

WO   WO 2010083404 A2 *   7/2010

OTHER PUBLICATIONS

Gura, Science Nov. 7, 1997: vol. 278. No. 5340, pp. 1041-1042.*
Leaf, Clifton, Health Administrator vol. XVII, No. 1: 172-183, 2005.*
"Expert Scientific Group on Phase One Clinical Trials Final Report" Nov. 30, 2006, pp. C1, C35-C38.*
Cancer Drug Design and Discovery Neidle, Stephen, ed. (Elsevier/Academic Press, 2008) pp. 427-431.*
Kamb, Nature Reviews Drug Discovery 4, 161-165 (Feb. 2005).*
Luo et al. Cell 2009, 136, 823-837.*
Mokhtari et al. C. R. Chimie 2009, 12, 1102-1108.*
Hecht et al. Journal of Clinical Oncology 2000, 18, 3707-3721.*
Delgado et al. Genes & Cancer 2010, 1, 605-616.*
CAS entry for Acheson et al. Journal of Chemical Research 1986, 8, 269.*
Dang et al. Cell, 2012, 149, 22-35.*
Roberts, Jr et al., JAMA 292(17): 2130-2140 (2004).*
Kola, Nature Reviews Drug Discovery 3, 711-715 (2004).*
PubChem entry for CID 71521277, which has a create date of Jun. 11, 2013.*
CAS Registry Entry for Registry No. 413611-97-9, which entered STN on May 12, 2002.*
CAS Registry Entry for Registry No. 314030-64-3, which entered STN on Jan. 16, 2001.*
CAS Registry Entry for Registry No. 377052-84-1, which entered STN on Dec. 20, 2001.*
Halle et al. Can. J. Chem. 1997, 75, 1240-1247.*
Adhikary, S. et al. Transcriptional Regulation and Transformation by MYC Proteins, *Nat. Rev. Mol. Cell Biol.* 2005, 6, 635-645.
Berg, T. et al. Small-molecule antagonists of Myc/Max dimerization inhibit Myc-induced transformation of chicken embryo fibroblasts, *Proc. Natl. Acad. Sci. USA* 2002, 99, 3830-3835.
Berns, E. M. J. J. et al. c-*myc* Amplification is a Better Prognostic Factor then *HER2/neu* Amplification Primary Breast Cancer, *Cancer Res* 1992.
Blackwood, E. M. et al. Max: A Helix-Loop-Helix Zipper Protein That Forms a Sequence-Specific DNA-Binding Complex with Myc, *Science* 1991, 251, 1211-1217.
Boger, D. L. et al. Two Comparisons of the Performance of Positional Scanning and Deletion Synthesis for the Identification of Active Constituents in Mixture Combinatorial Libraries, *J. Org. Chem.* 2000, 65, 1467-1474.
Boxer, L. M. et al. Translocations involving c-myc and c-myc funcation, *Oncogene* 2001, 20, 5595-5610.
Buchholz, M. et al. Overexpression of c-myc in pancreatic cancer caused by ectopic activation of NFATcl and $Ca^{2+}$/calcineurin singaling pathway, *Embo J.* 2006, 25, 3714-3724.
Clausen, D.M. et al. In Vitro Cytotoxity and In Vivo Efficacy, Pharmacokinectics, and Metabolism of 10074-G5, a Novel Small-Molecule Inhibitor of c-Myc/Max Dimerization, *J. Pharmacol. Exp. Ther.* 2010, 335, 715-727.
Dalla-Favera, R.et al. Human c-*myc one* gene is located on the region of chromosomes 8 that is translocated in Burkitt lymphoma cells, *Proc. Natl. Acad. Sci. USA* 1982, 79, 7824-7827.
Dang, C.V. c-Myc Target Genes Involved in Cell Growth, Apoptosis, and Metabolism, *Cell Biol.* 1999, 19, 1-11.
Delgado, M. D. et al. Myc Roles in Hematopoiesis and Leukemia, *Genes Cancer* 2010,1, 605-616.
Delmore, J. E. et al . BET Bromodomain Inhibition as a Therapeutic Stategy to Target c-Myc, *Cell* 2011, 146, 904-917.
Erisman, M.D. et al. Deregulation of c-*myc* Gene Expression in Human Colon Carcinoma is Not Accompanied by Amplification or Rearrangement of the Gene, *Mol. Cell. Biol.* 1985, 5,1969-1976.
Felsher, D. W. et al. Reversible Tumorigenesis by Myc in Hematopoietic Lineages, *Mol. Cell.* 1999, 4, 199-207.
Filippakopoulos, P. et al. Selective inhibition of BET bromodomains, *Nature* 2010, 468, 1067-1073.

(Continued)

*Primary Examiner* — Matthew Coughlin
(74) *Attorney, Agent, or Firm* — Marianne Fuierer; Moore & Van Allen, PLLC

(57) ABSTRACT

The present invention relates compounds and compositions for interfering with the association of Myc and Max. These compounds and compositions are useful in methods for inhibiting growth or proliferation of a cell. Methods of inhibiting growth or proliferation of a cell comprise contacting the cell with an amount of a compound that interferes with Myc and Max association effective to inhibit growth or proliferation of the cell. The compounds exhibit increased inhibitory activity against c-Myc relative to the known c-Myc inhibitor small-molecule benzofurazan N-([1,1'-biphenyl]-2-yl)-7-nitrobenzo[c][1,2,5]oxadiazol-4-amine (10074-G5).

11 Claims, 13 Drawing Sheets

(56) References Cited

OTHER PUBLICATIONS

Follis, A.V. Structural Rationale for the Coupled Binding and Unfolding of the c-Myc Oncoprotein by Small Molecules, *Chem. Biol.* 2008, 15, 1149-1155.

Gardner, L. B. et al. *c-myc* Protooncogne, *Encyclopedia of Cancer*, 2002, 2nd Ed (Bertino J Eds) pp. 555-561, Elsevier Science, Burlington, MA.

Guo, J. et al. Efficacy, pharmacokinetics, tissue distribution, and metabolism of the Myc-Max disruptor, 10058-F4 [Z,E]-5-[4-ethylbenzylidine]-2-thioxothiazolidin-4-one, in mice, *Cancer Chemother. Pharmacol.* 2009, 63, 615-625.

Hammoudeh, D.I. et al. Multiple Independent Binding Sites for Small-Molecule Inhibitors on the Oncoprotein c-Myc, *J. Am. Chem. Soc.* 2009, 131, 7390-7401.

Hecht, J. L. et al. Molecular Biology of Burkitt's Lymphoma, *J. Clin. Oncol.* 2000, 18, 3707-3721.

Hermeking, H. et al. Identification of CDK4 as a targt of c-Myc, *Proc Natl Acad Sci U S A* 2000, 97, 2229-2234.

Huang, M. J. et al. A small-molecule c-Myc inhibitor, 10058-F4, induces cell-cycle arrent, apoptosis, and myeloid differentiation of human acute myeloid leukemia, *Exp. Hematol.* 2006, 34, 1480-1489.

Jagodzinska, M. et al. Assessing the Bioisosterism of the Trifluoromethyl Group with a Protease Probe, *ChemMedChem* 2008, 4, 49-51.

Jung, M. E. Improved synthesis of 4-amino-7-nitrobenz-2,1,3-oxadiazoles using NBD fluoride (NBD-F), *Tetrahedron Lett.* 2011, 52, 2533-2535.

Kiessling, A. et al. Selective Inhibtion of c-Myc/Max Dimerization and DMA Binding by Small Molecules, *Chem. Biol.* 2006, 13, 745-751.

Kiessling, A. et al. Selective Inhibition of c-Myc/Max Dimerization by a Pyrazolo[1,5-a]-pyrimidine, *ChemMedChem*, 2007, 2, 627-630.

Kretzner, L. et al. Myc and Max proteins possess distinct transcriptional acitivities, *Nature* 1992, 359, 426-429.

Lin, C.Y. et al. Transcriptional Amplification in Tumor Cells with Elevated c-Myc, *Cell* 2012, 151, 56-67.

Michel, J. et al. The Impact of Small Molecule Binding on the Energy Landscape of the Intrinsically Disordered Protein C-Myc, *PLoS One* 2012. 7, e41070.

Mitani, S. Analysis of c-muc DNA amplification in non-small cell lung carcinoma in comparison with small cell lung carcinoma using polymerase chain reaction, *Clin. Exp. Med.* 2001, 1, 105-111.

Mo, H. et al. Identification of small molecules that induce apoptosis in a Myc-dependent manner and inhibit Myc-driven transformation, *Proc. Natl. Acad. Sci. USA* 2006, 103, 6344-6349.

Nair, S. K. et al. X-Ray Structures of Myc-Max and Mad-Max Recognizing DNA: Molecular Bases of Regulation by Proto-Oncogenic Transcription Factor, *Cell* 2003, 112, 193-205.

Nesbit, C.E. et al. *MYC* oncogenes and human neoplastic disease, *Oncogene* 1999, 18, 3004-3016.

Nie, Z. et al. c-Myc is a Universal Amplifier of Expressed Genes in Lymphocytes and Embryonic Stem Cells, *Cell* 2012, 151, 68-79.

Park, C.M. et al. Discovery of an Orally Bioavailable Small Molecule Inhibitor of Prosurvival B-Cell Lymphoma 2 Proteins. *J. Med. Chem.* 2008, 51, 6902-6915.

Pelengaris, S. et al. c-MYC: More Than Just a Matter of Life and Death, *Nat. Rev. Cancer* 2002, 2, 764-776.

Prendergast, G. C. et al. Association of Myn, the Murine Homolog of Max, with c-Myc Stimulates Methylation-Sensitive DNA Binding and Ras Cotransformation, *Cell* 1991, 65, 395-407.

Prochownik, E.V. et al. Therapeutic Targeting of Myc, *Genes Cancer* 2010, 1, 650-659.

Rapp, U.R. et al. Myc is a Metastasis Gene for Non-Small-Cell Lung Cancer, *PLoS One* 2009, 4, e6029.

Shi, J. et al. Small molecule inhibitors of Myc/Max dimerization and Myc-induced cell transformation, *Bioorg. Med. Chem. Lett.* 2009, 19, 6038-6041.

Soucek, L. et al. Modelling Myc Inhibition as a cancer therapy, *Nature* 2008, 455, 679-683.

Soucek, L. et al. The ups and downs of Myc biology, *Curr. Opin. Genet. Dev.* 2010, 20:91-95.

Soucek, L. et al. Inhibition of Myc family proteins eradicates KRas-driven.lung cancer in mice, *Genes Dev.* 2013, 27, 504-513.

Wang, H. et al. Improved low molecular weight Myc-Max inhibitors, *Mol. Cancer Ther.* 2007, 6, 2399-2408.

Wang, H. et al. Disruption of Myc-Max Heterodimerization with Improved Cell-Penetrating Analogs of the Small Molecule 10074-G5, *Oncotarget* 2013, 4:936-947.

Xu, Y. et al. A credit-card library approach for disrupting protein-protein interactions, *Bioorg. Med. Chem.* 2006, 14, 2660-2673.

Yap, J.L. et al. Small-molecule inhibitors of dimeric transcription factors: Antagonism of protein-protein and protein-DNA interactions, *Med. Chem. Commun.* 2012, 3, 541-551.

Yap, J. L. et al. Pharmacophore identification of c-Myc inhibitor 10074-G5, *Bioorg. Med. Chem. Lett.* 2013, 23, 370-374.

Yin, X. et al. Low molecular weight inhibitors of Myc-Max interaction and function, *Oncogene* 2003, 22, 6151-6159.

www.cancer.org, Sep. 25, 2014.

\* cited by examiner

| Compound | IC$_{50}$ (μM) | |
|---|---|---|
| | HL60 | Daudi |
| JY-3-094 | >100 | >100 |
| 3JC-91-1 | 20 | 7.8 |
| 3JC-91-2 | 7.2 | 3.5 |
| 3JC-91-3 | >25 | 7.4 |
| 3JC-91-4 | 9.3 | 3.1 |
| 3JC-91-5 | 31.9 | 30.7 |
| 3JC-91-7 | 8.5 | 1.9 |
| SF-4-017 | 9.6 | 3.1 |

Figure 7

POTENT ANALOGUES OF THE C-MYC INHIBITOR 10074-G5 WITH IMPROVED CELL PERMEABILITY

CROSS-REFERENCE TO RELATED APPLICATION

The present application claims priority to U.S. Provisional Application Nos. 61/805,623, filed on Mar. 27, 2013 and 61/866,763, filed on Aug. 16, 2013, the contents of both applications are hereby incorporated by reference herein for all purposes.

BACKGROUND OF THE INVENTION

1. Field of the Invention

The present invention relates to compounds and compositions for interfering with the association of Myc and Max. These compounds and compositions are useful in methods for inhibiting growth or proliferation of a cell. Methods of inhibiting growth or proliferation of a cell comprise contacting the cell with an amount of a compound that interferes with Myc and Max association effective to inhibit growth or proliferation of the cell. The compounds exhibit increased inhibitory activity against c-Myc relative to the known c-Myc inhibitor small-molecule N-([1,1'-biphenyl]-2-yl)-7-nitrobenzo[c][1,2,5]oxadiazol-4-amine (10074-G5).

2. Description of the Related Art c-Myc is important in the transcription of a myriad of genes involved in roles that include cell proliferation, apoptosis, differentiation and metabolism.(1-6) Though Myc is essential for normal cell function, its over-expression and/or dys-regulation is associated with a wide variety of human cancers, including, but not limited to, leukaemias and Burkitt's lymphoma, as well as cancers of the breast, pancreatic, lung and colon. (8-14, 20-21) Given its central role in many key cellular processes, there is concern that, by definition, c-Myc must possess a narrow therapeutic window, which would render the development of c-Myc inhibitors that are non-toxic to normal cells especially challenging. (15) However, recently there have been several reports that the inhibition of c-Myc, whilst lethal to transformed cells, exhibits only mild and reversible effects on normal cells.(8,16,17) Moreover, it now appears that c-Myc actually exerts an amplifying control on transcription of its target genes,(18,19) such that its inhibition would not result in complete inactivation of transcription. Together, these findings support the idea that the inhibition of c-Myc is a viable strategy towards the development of targeted antineoplastics.

In 2012, it was estimated there would be about 577,190 cancer deaths in the United States alone (39), about one-seventh of which will be associated with tumours exhibiting changes in the c-myc proto-oncogene or its expression (1). Inactivation of Myc results in cell-cycle arrest, apoptosis and tumour regression (40-42). Thus, the inhibition of Myc function is an appealing tactic to expand the arsenal of anticancer therapeutics in a highly targeted manner. Currently, there is no such "Myc drug" in the clinic, and the most potent Myc inhibitors to date exhibit only low micromolar $IC_{50}$ values (20). Given the significant role of Myc in the development and progression of a wide variety of cancers, there is an urgent need for more potent and diverse Myc inhibitors.

c-Myc (Myc) is a short-lived ($t_{1/2}$=20-30 min) nuclear oncoprotein and is a member of the basic-helix-loop-helix leucine zipper (bHLH-LZ) protein family of transcription factors that includes its obligate binding partner, Max, and its antagonist proteins of the Mad family (1). In its monomeric form, c-Myc is intrinsically disordered and transcriptionally inactive. However, upon dimerization with the bHLH-ZIP relative Max, an obligatory event that is required for all of c-Myc's known biological activities,(1-5) c-Myc and Max assume a coiled coil structure that recognizes the E-box sequence (5'-CACGTG-3') in DNA.(6) Subsequently, various co-activators are recruited to initiate transcription. Unlike c-Myc, Max is capable of forming homodimers, as well as heterodimers with other bHLH-ZIP family members that include Mad, Mxi-1 (Mad2) and Mnt.(7) Although they repress transcription, Max-Max, Max-Mad and Max-Mxi-1 dimers retain the ability to bind E-box elements, and, therefore, compete with c-Myc-Max heterodimers, which provides a means by which c-Myc's transcriptional activity is kept in check.(7)

In its monomeric form, the bHLH-LZ domain of Myc (and Max) is intrinsically disordered, presenting no obvious binding sites for the development of inhibitors (6). Myc becomes transcriptionally functional only upon its heterodimerization with Max, an event in which the two proteins act as each other's chaperone to generate a parallel, left-handed four-helix bundle structure that recognizes the obligate E-box DNA sequence CAC/TGTG. The Myc-Max heterodimer thus serves as an excellent example of the coupled folding and binding of two intrinsically disorderd proteins. Indeed, most biological activities of Myc require this interaction (43-45). The basic regions of Myc and Max bind the DNA, while the HLH and LZ domains form the dimerization interface. Unlike Myc, Max is constitutively expressed, is stable ($t_{1/2}$>24 h) and can also homodimerize. Max-Max homodimers bind the same DNA sequence as Myc-Max heterodimers but rather inhibit transcription, which is manifested through the direct competition for Max and for the common DNA site.

Since the dimerization of c-Myc and Max is an essential criterion for c-Myc to become functional, it follows that the disruption of the protein-protein interactions between c-Myc and Max should be an effective approach towards the inhibition of c-Myc's transcriptional activity. However, monomeric c-Myc's intrinsic disorder renders rational drug design a significant challenge, with the protein bereft of any recognizable sites that molecules could dock into or that computationally assisted docking programs could enlist as potential binding sites in virtual screens. (20,21) Furthermore, there does not appear to be any obvious binding pockets on the structure c-Myc-Max heterodimer, either. Unsurprisingly, therefore, the majority of small-molecule inhibitors of c-Myc-Max dimerization have been identified through screening large chemical libraries, and span structurally diverse chemotypes. (20) These small-molecules include rhodanine and thiazolidine-2,5-dione derivatives,(22,23) peptidomimetic-based inhibitors,(24,25) "credit-card" compounds that are based on planar, hydrophobic scaffolds designed to "slot" into the c-Myc-Max leucine zipper,(26) and the pyrazolo[1,5-a]pyrimidine "Mycro" compounds,(27, 28) as well as indirect c-Myc inhibitors, such as "JQ-1", a thieno-triazolobenzo-1,4-diazepine that inhibits bromodomain-containing proteins. (29) A select few of these have been characterized more fully and shown to operate through the recognition and stabilization of monomeric, transcriptionally inactive c-Myc, preventing it from undergoing its obligatory dimerization with Max. (30,31) Two such compounds are 10058-F4 ((Z)-5-(4-ethylbenzylidene)thiazolidine-2,4-dione) and 10074-G5 (N-([1,1'-biphenyl]-2-yl)-7-nitrobenzo[c][1,2,5]oxadiazol-4-amine), the former of which was previously developed into more potent congeners.(23)

Owing to a lack of recognizable binding clefts or motifs, coupled with an inability to predict the structures of potential Myc-Max disruptors, the majority of inhibitors reported to date have been identified by screening large libraries of compounds, as stated above, and most compounds identified to date have been hampered by low affinity binding and/or poor in vivo activity against Myc-dependent tumors (21, 35, 49). Accordingly, there is a need for new compounds that inhibit Myc-activity.

SUMMARY OF THE INVENTION

The present invention provides for small molecules that inhibit the activity of the oncogenic protein c-Myc and interfere with c-Myc-Max dimerization and/or Max-Max dimerization.

In one aspect, the present invention provides for methods, compounds and compositions for disruption of c-Myc binding and activation. In certain embodiments, the compositions comprise moieties that specifically bind c-Myc and further disrupt its association with its binding partner Max.

In another aspect, the present invention provides for the analogues of 10074-G5 as described herein and that specifically bind to c-Myc with increased affinity relative to 10074-G5.

In yet another aspect, the present invention provides for c-Myc binding moieties having a formula selected from:

JY-3-094

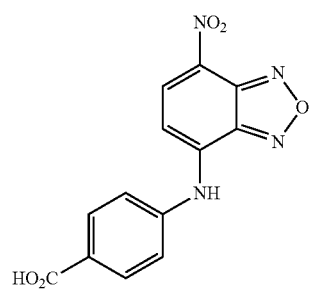

3jc48-3

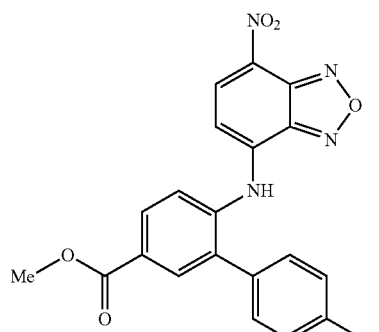

4jc23-4

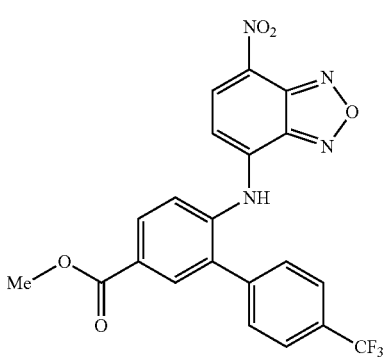

SF-3-103B

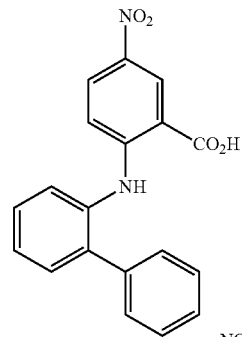

SF-4-017

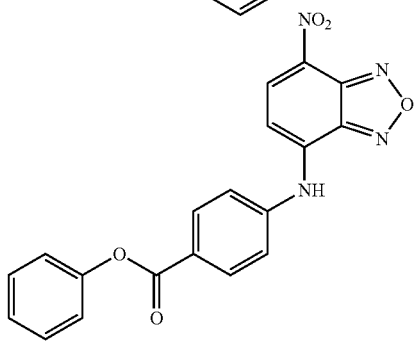

JY-5-261

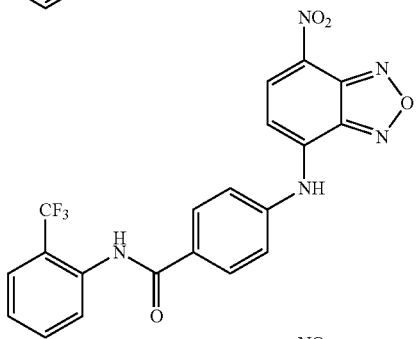

JY-5-195

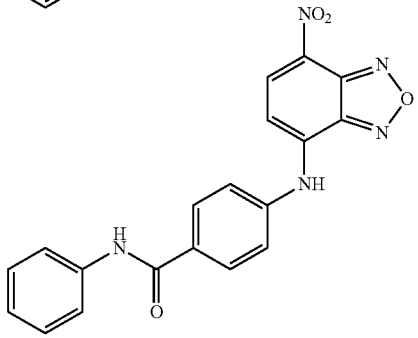

3jc53-3

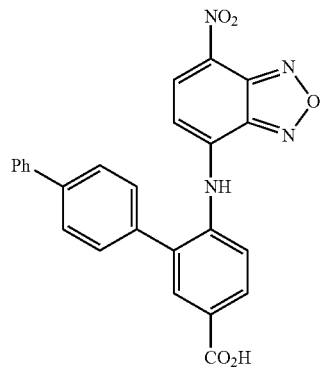

-continued

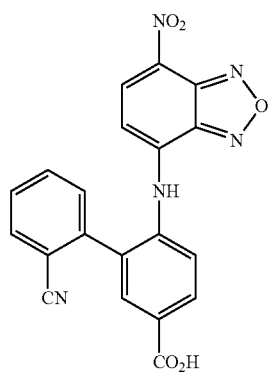
3jc53-7 or pharmaceutically acceptable salt thereof.

In a still further aspect, the present invention provides for methods of treatment for diseases wherein dimerization of c-Myc-Max or c-Myc dysregulation contributes to pathogenesis. For example, in certain embodiments, the compounds described herein can be formulated as pharmaceuticals designed to treat diseases such as Burkitt's lymphoma cell; non-Burkitt's lymphoma; prostate cancer; breast cancer; gastrointestinal cancer melanoma; multiple myeloma; myeloid leukemia, and others.

Another aspect of the present invention provides for a method for interfering with Myc function, cell growth and/or tumor growth that includes the steps of contacting a cell or tumor, or administering to a patient, an amount of an active compound effective to interfere with Myc function, inhibit cell growth and/or inhibit tumor growth. Compounds useful in these methods include nine parent compounds of the formula selected from:

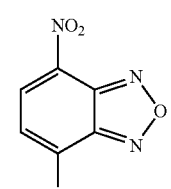
JY-3-094

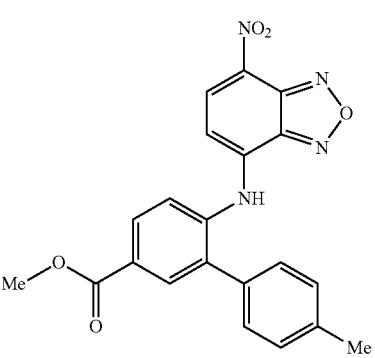
3jc48-3

-continued

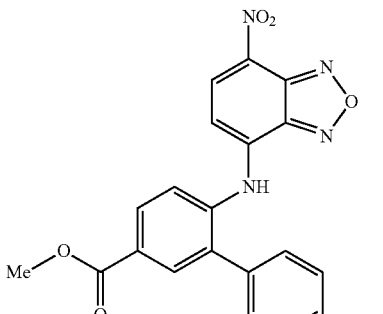
4jc23-4

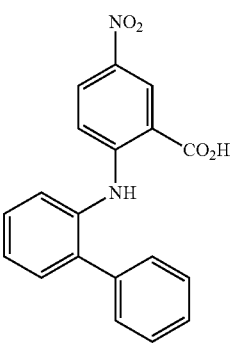
SF-3-103B

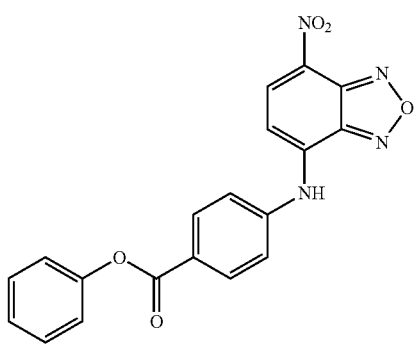
SF-4-017

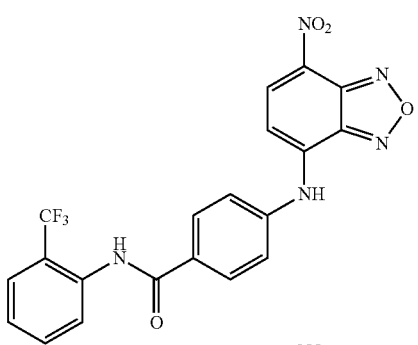
JY-5-261

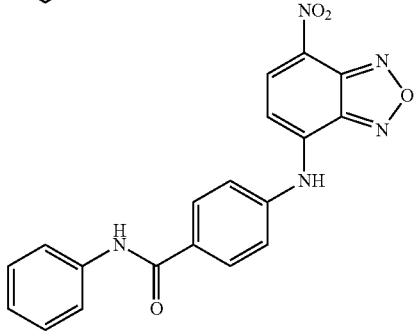
JY-5-195

-continued

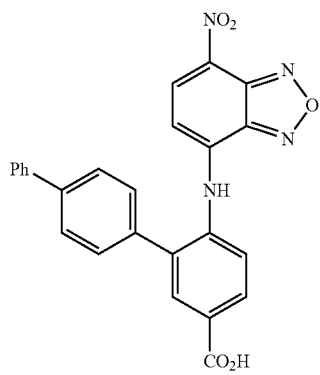
3jc53-3

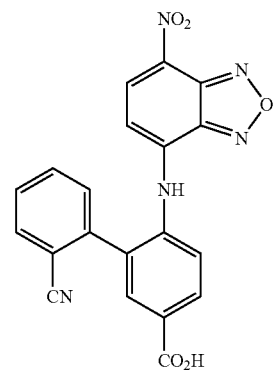
3jc53-7 or pharmaceutically acceptable salts thereof.

Also useful in the methods described herein are derivatives and salts of the described compounds of the present invention that interfere with Myc and Max association function and cell or tumor growth as determined by the assays described herein.

Another aspect of the present invention provides for a compound having a formula:

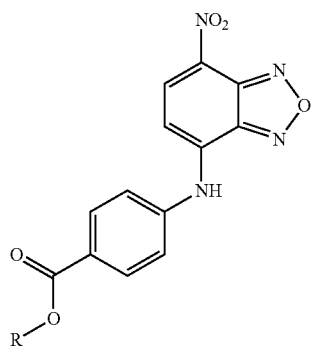

wherein R is H, $CH_3$, Bn, $CH_2CH_3$, $CH_2O(CO)CH_3$, $CH_2CF_3$, aryl, alkyl or Ph.

In yet another aspect, the present invention provides for a compound having a formula:

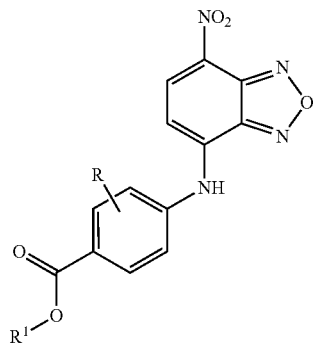

wherein R is H, alkyl, aryl, heteroaryl, CN, $CO_2H$, $CONH_2$, OH, halogen, $NH_2$ or $NO_2$ and $R^1$ is alkyl, aryl, cycloalkyl, benzyl, $CH_2CF_3$, $CF_2CF_3$ or $CH_2O(CO)CH_3$.

In a still further aspect, the present invention provides for a compound having a formula:

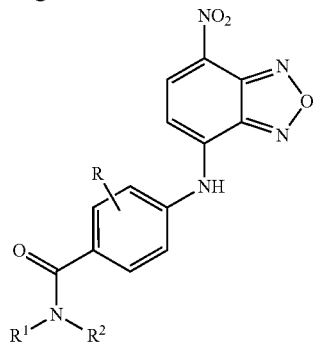

wherein R is H, alkyl, aryl, heteroaryl, CN, $CO_2H$, $CONH_2$, OH, halogen, $NH_2$ or $NO_2$ and $R^1$ and $R^2$ is H, alkyl, aryl, cycloalkyl or benzyl.

In another aspect, the present invention provides for a compound having a formula:

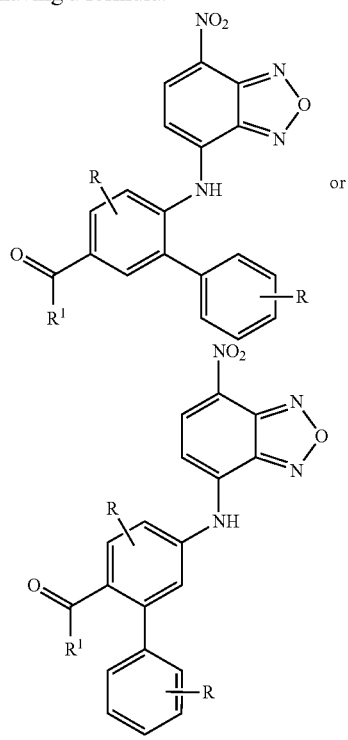

or wherein R is H, alkyl, aryl, heteroaryl, CN, CO₂H, CONH₂, OH, halogen NH₂ or NO₂ and R¹ is alkyl $C_1$ to $C_4$ or OH.
In yet another aspect, the present invention provides for analogues of a parent compound, wherein one or more groups of the parent compound is substituted with a different group, wherein the parent compound has a formula selected from:
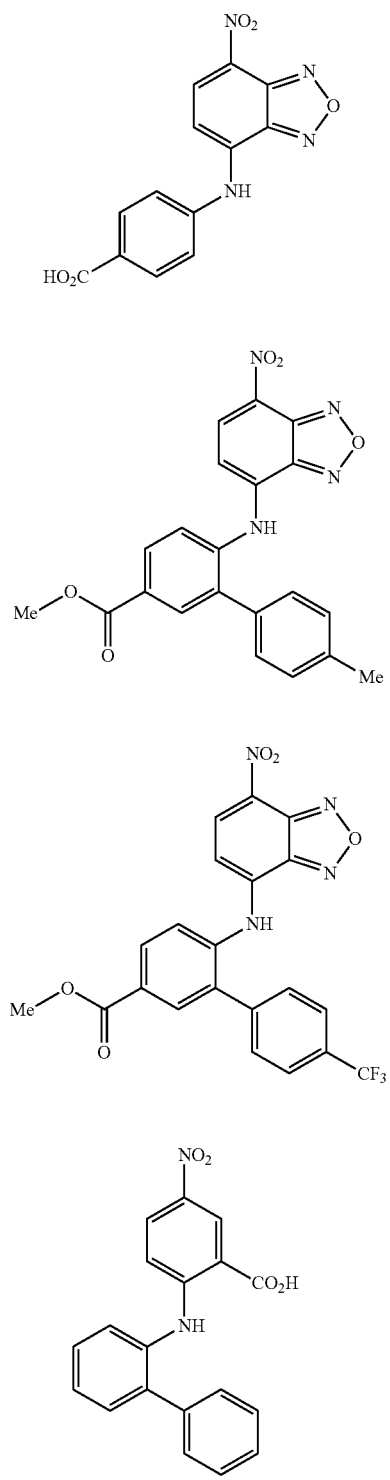
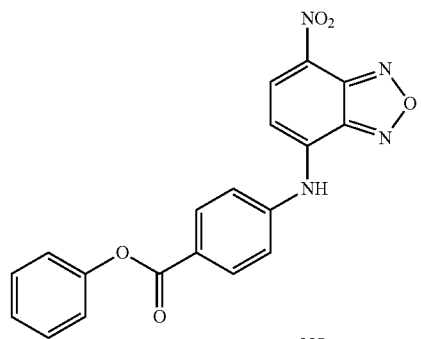
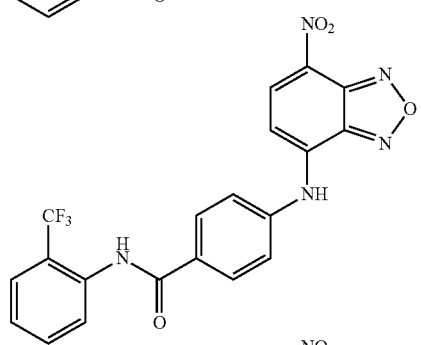
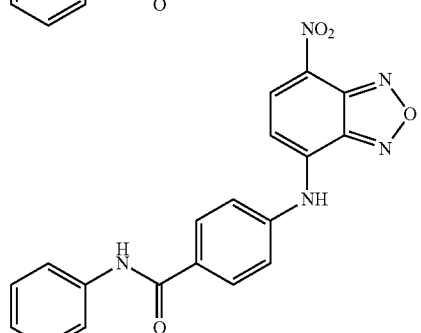
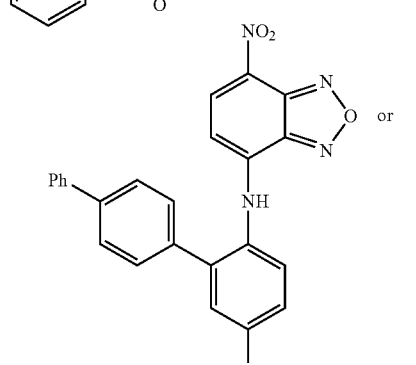
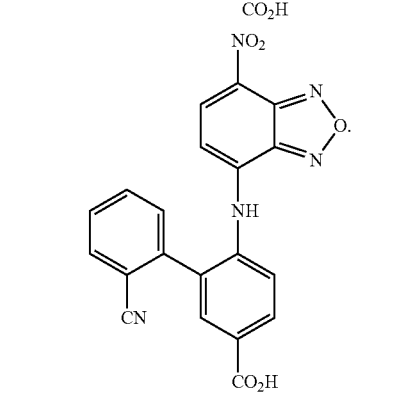

The above-described active compounds are demonstrated as useful in inhibiting cell growth and tumor formation. Compositions therefore are provided that facilitate delivery of those active compounds, such as emulsions, including oil in water emulsions and liposomes, and complexes with solubilizing agents, such as cyclodextrins and polyoxyethylene-conjugated vegetable oils. The compositions include an active compound, as described herein, and an excipient.

The above described parent compounds are also useful as starting points for rational drug development methods, either in silico or by more conventional "wet" chemical synthesis and screening methods. In the in silico methods, computerized processes are used to screen derivatives of the lead compounds for their effect on the association of Myc and Max. Additional derivatives having one or more groups substituted with a different group. Any derivative can be screened according to methods described herein.

Other aspects, features and embodiments of the invention will be more fully apparent from the ensuing disclosure and appended claims.

BRIEF DESCRIPTION OF THE FIGURES

FIG. 7 shows the results of Pro-drug cytotoxicites (XTT assay) in HL60 and Daudi c-Myc-overexpressing cells.

DETAILED DESCRIPTION OF THE PRESENT INVENTION

Figure 1:
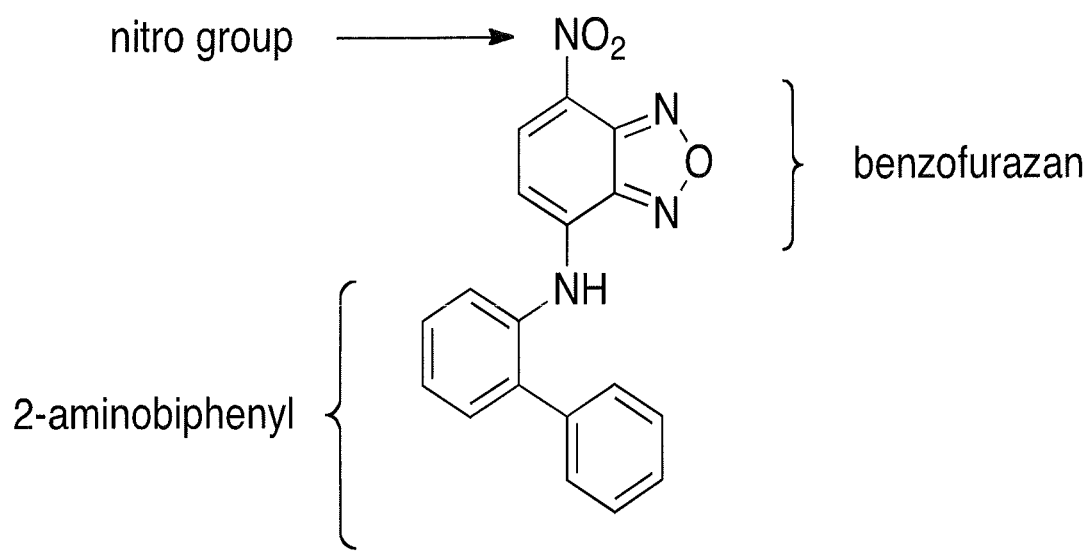
FIG. 1 shows the chemical structure of Myc inhibitor 10074-G5 and its three components that may be readily modulated in an SAR research program.

The Myc-Max dimerization inhibitors: the rhodanine derivative (Z)-5-(4-ethylbenzylidene)-2-thioxothiazolidin-4-one (10058-F4) and N-([1,1'-biphenyl]-2-yl)-7-nitrobenzo[c][1,2,5]oxadiazol-4-amine (10074-G5)(22) were characterized and it was found that the mode of Myc-Max dimerization inhibition by these two small-molecules is through the direct binding of the Myc monomer (10058-F4 binds $Myc_{402-412}$, 10074-G5 binds $Myc_{363-381}$), thereby limiting its ability to interact with Max (30, 31). FIG. 1 shows the chemical structure of Myc inhibitor 10074-G5 and its three components, that being, the biphenyl, the benzofurazan and the nitro group.

Figure 2:
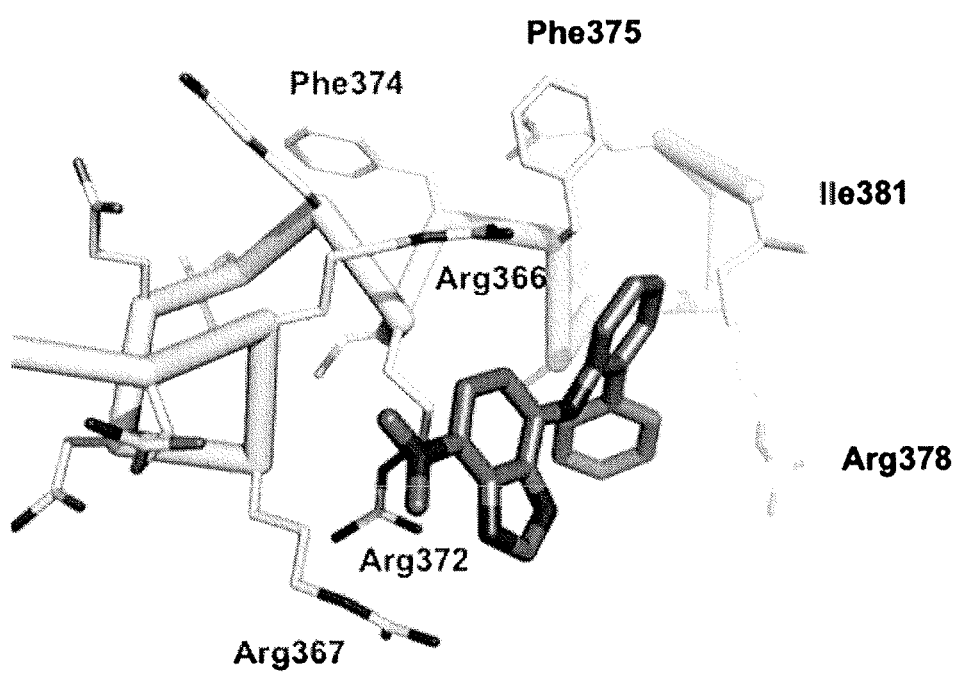
FIG. 2 shows the docking between 10074-G5 and Myc363-381.

It has recently been demonstrated that 10074-G5 binds Myc in the region Arg363-Ile381 (FIG. 2) (30,31). More particularly, NMR NOESY analysis and docking studies independently suggested that 10074-G5 binds in a cavity that is created by a kink (Asp379-Ile381) in the N-terminus of an induced helical domain (Leu370-Arg378), with the biphenyl moiety observed in the hydrophobic domain formed by Phe375, Ile381 and the side chain methylenes of Arg378, and the electron rich 1,2,5-oxadiazole ring and nitro group found near the positively-charged residues Arg366 and Arg367.

The pharmacophore of 10074-G5 was determined by an SAR study that explored the significance of the biphenyl, the aniline NH, the benzofurazan and the nitro group, as shown in FIG. 1. Maximal Myc inhibitory activity requires the electron rich 7-nitrobenzofurazan ring, which is consistent with its predicted binding mode to the positively-charged residues Arg366 and Arg367 that would be expected to contribute considerably to the binding energy. Furthermore, the 7-nitrobenzofurazan is preferably substituted with a secondary aniline (or phenol) at the 4-position. More particularly, this aniline preferably requires a bulky, hydrophobic substituent (e.g. phenyl) at the ortho position, which may engage in van der Waals interactions with Phe375 and Ile381, or a carboxylic acid at the para position, which may be involved in a salt bridge with Arg378 that is located at the N-terminus of the induced helix.

Variations of the biphenyl moiety were accomplished by reacting 4-chloro-7-nitrobenzofurazan 2 with a range of anilines and aliphatic amines ($RNH_2$) to furnish target molecules 3a-3q (Table 1) in moderate to excellent yields. The requisite chemical reactions were straightforward and are illustrated in Scheme 1, shown below:

Scheme 1.

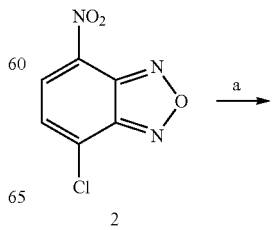

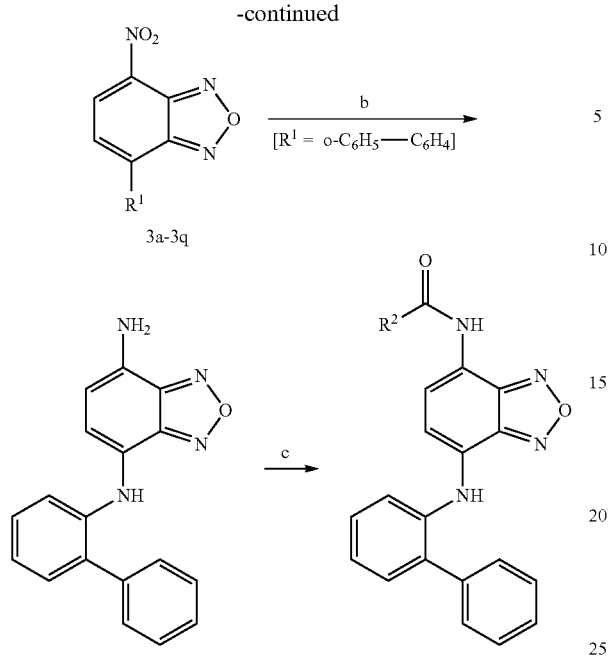

a) RNH₂, CH₃CN, DIPEA, reflux 16 h, 35-99%; b) H₂, 10% Pd/C, MeOH, RT, 16 h, 76%; c) R₂COX, CH₂Cl₂, Et₃N, 0° C. to RT (or 40° C.), 16 h, 38-95%.

Hydrogenation of the nitro group of 10074-G5 provided the corresponding aniline 4 (shown above and in Table 2) that was subsequently reacted with various acylating agents to deliver compounds 5a-5c (Table 2). Finally, N-arylation of 2-aminobiphenyl with 4-fluoronitrobenzene 6 delivered secondary aniline 7.

Analogues of 10074-G5 were initially screened at 100 μM in an electrophoretic mobility shift assay (EMSA) (50). Effective compounds disrupted the interaction of homogeneously purified recombinant Myc bHLH-LZ domain and Max proteins with a fluorescently-tagged (FAM) E-Box-containing double-stranded oligonucleotide. The results are shown below in Tables 1 and 2, and are reported as percentage inhibitions that were determined through comparison of Myc-Max/DNA band intensities in the presence of the candidate inhibitor relative to the control band intensity acquired in its absence.

TABLE 1

Structural Analogues of Compound No. 10074-G5.

| Compound | R¹ | Inhibition at 100 μM (%) |
|---|---|---|
| 10074-G5 | HN-(2-biphenyl) | 38 |
| 3a | HN-phenyl | 2 |
| 3b | HN-cyclohexyl | 11 |
| 3c | HN-CH₂-phenyl | 0 |
| 3d | piperidinyl (N-linked) | 10 |
| 3e | HN-(2-methylphenyl) | 11 |
| 3f | HN-(2-bromophenyl) | 39 |
| 3g | HN-(2-hydroxyphenyl) | 13 |
| 3h | HN-(2-methoxyphenyl) | 0 |

TABLE 1-continued

Structural Analogues of Compound No. 10074-G5.

[Structure: 7-nitrobenzofurazan with R¹ substituent at 4-position]

| Compound | R¹ | Inhibition at 100 μM (%) |
|---|---|---|
| 3i | -HN-C₆H₄-COOH (ortho) | 8 |
| 3j | -O-C₆H₄-C₆H₅ (ortho-biphenyl ether) | 36 |
| 3k | -HN-naphthalen-1-yl | 0 |
| 3l | -HN-C₆H₅ | 20 |
| 3m | -HN-C₆H₄-COOH (meta) | 0 |
| 3n | -HN-C₆H₄-C₆H₅ (para-biphenyl) | 28 |
| 3o | -HN-C₆H₄-CH₃ (para) | 0 |
| 3p | -HN-C₆H₄-OH (para) | 0 |
| 3q ("JY-3-094") | -HN-C₆H₄-COOH (para) | 93 |

First, as shown by the activity for 3a, an unsubstituted aniline at the 4-position of the 7-nitrobenzofurazan nucleus was insufficient for activity. Furthermore, a small hydrophobic group (3e) or hydrophilic group (3g) at the ortho position afforded compounds with minimal Myc-Max inhibitory activities. On the other hand, bulky, hydrophobic groups at the ortho position (phenyl (10074-G5), bromo (3f)) furnished inhibitors that exhibited about 40% disruption of the Myc-Max dimer. These groups may be directed into the hydrophobic domain composed of Phe375 and Ile381. Shifting the ortho-phenyl ring to the meta and para positions (3l and 3n, respectively) led to a reduction in activity, underscoring the importance of hydrophobicity at the ortho site. Consistent with this is the observation that polar carboxylic acids were poorly tolerated at the ortho and meta positions (3i and 3m, respectively) but afforded excellent inhibition of Myc-Max dimers at the para position (3q, hereafter "JY-3-094"). This trend also suggests that the promising activity of JY-3-094 is not simply a consequence of improved solubility by virtue of the ionizable carboxylic acid since the regioisomers 3i and 3n would be expected to exhibit comparable solubility, yet they demonstrated little to no inhibitory activities. The isosteric replacement of the aniline NH group with oxygen (compound 3j) had no impact on the disruption of the Myc-Max dimer, indicating that a hydrogen bond donor may have a minimal role here. Reduction of the nitro group to the corresponding amine (38) was not tolerated, and this may be a consequence of the loss of the interaction between the electron rich nitro group and the positively-charged Arg366 and Arg367 residues.

Acetylation of the primary amino group of 4 to furnish acetamide 5a did not lead to recovery of Myc inhibitory activity, as shown in the results of Table 2. However, replacement of the acetyl group with the more-electron rich trifluoroacetyl bioisostere delivered inhibitor 5b that effected 25% inhibition of the Myc-Max heterodimer. Moreover, the coupling of 4 to diglycolic anhydride furnished N-acyl derivative 5e with a carboxylic acid that demonstrated even greater inhibition of the Myc-Max heterodimer (33%). Taken together, these data suggest the nitro group of 10074-G5 does, indeed, make contacts with positively-charged residues, such as Arg367. Deletion of the 1,2,5-oxadiazole ring of the bicyclic benzofurazan system to give 7 abolished activity, indicating the importance of the nitrogen and oxygen heteroatoms that may be involved in polar interactions with Arg366 and Arg367 as originally proposed (30,31). The nitro group and benzofurazan ring, therefore, appear critical for Myc inhibitory activity.

TABLE 2

Structural Analogues of Compound No. 10074-G5.

| Compound | Structure | Inhibition at 100 µM (%) |
|---|---|---|
| 4 | 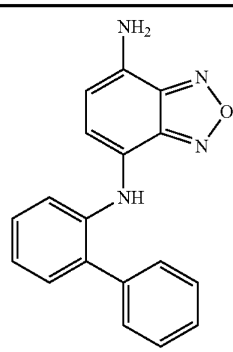 | 2 |
| 5a | 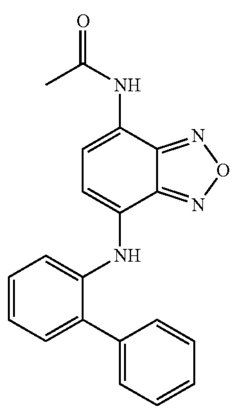 [SMILES: CC(=O)Nc1ccc(Nc2ccccc2-c2ccccc2)c2nonc12] | 2 |
| 5b | 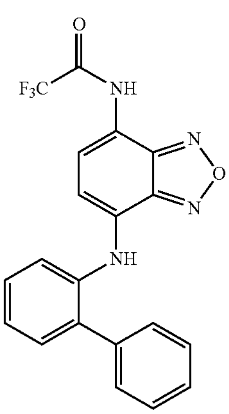 [SMILES: O=C(Nc1ccc(Nc2ccccc2-c2ccccc2)c2nonc12)C(F)(F)F] | 25 |
| 5c | | 0 |
| 5d | | 17 |
| 5e | | |

TABLE 2-continued

Structural Analogues of Compound No. 10074-G5.

| Compound | Structure | Inhibition at 100 μM (%) |
|---|---|---|
| 7 | 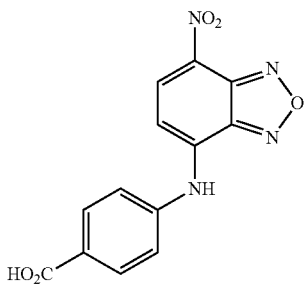 | 0 |

Additional structural analogues of Compound No. 10074-G5 are shown in Table 5.

Figure 3:
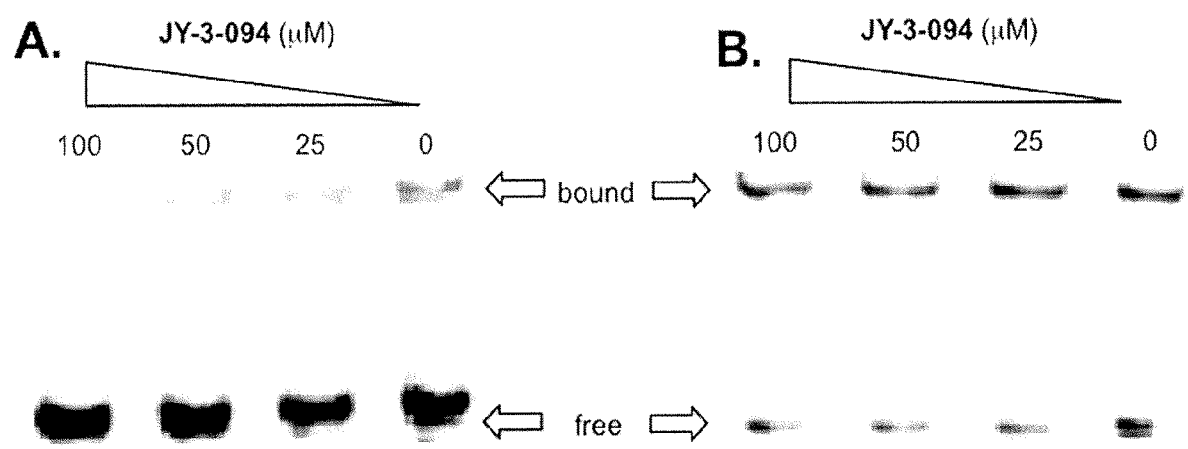
FIG. 3 shows that the analogue JY-3-094 exhibits a dose-dependent inhibition of the Myc-Max heterodimer, with no effect against Max-Max homodimers, as demonstrated by (A) a reduction in the Myc-Max/DNA band intensity and (B) no change in the Max-Max/DNA band intensity in EMSA assays.
Figure 4:
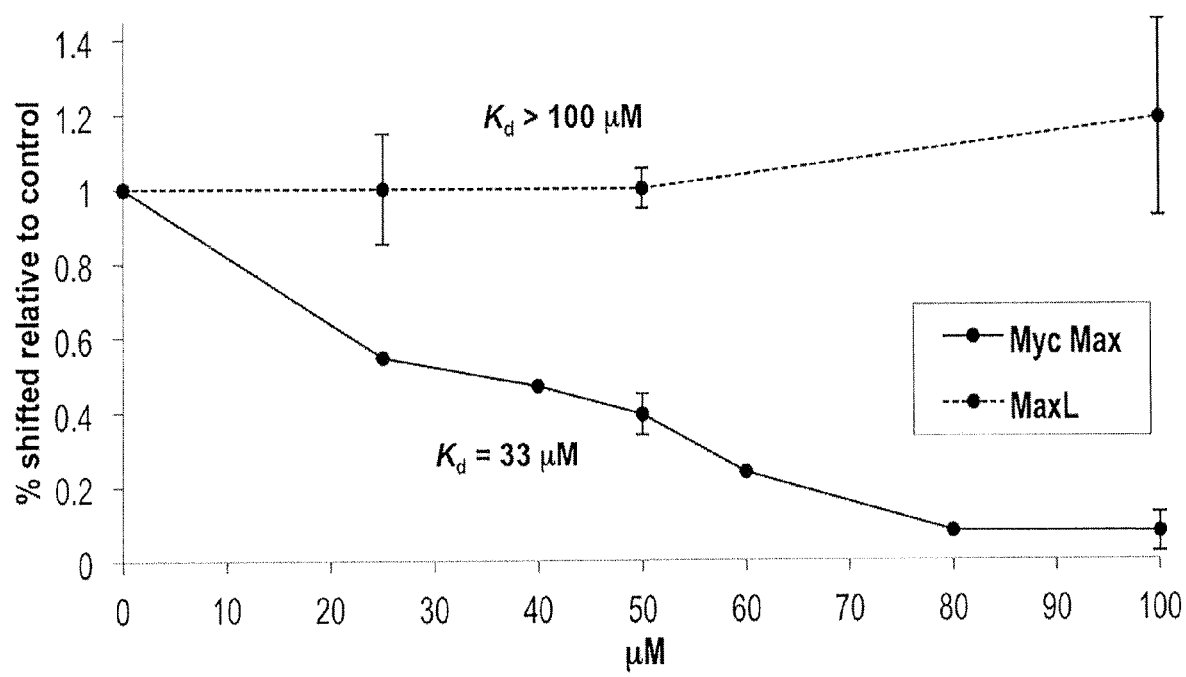
FIG. 4 shows that JY-3-094 is selective for Myc-Max heterodimers over Max-Max homodimers, as determined by EMSA assays.

Upon further characterization, JY-3-094 (compound 3q in Table 1, and structure shown below) was tested and shown to exhibit a dose-response inhibitory effect against Myc-Max dimerization (FIG. 3), with a $K_d$ value of 33 μM (FIG. 4), which is around five-fold as potent as the original lead 10074-G5 ($K_d$=146 μM). Notably, JY-3-094 showed no activity against Max-Max homodimers at 100 μM (FIGS. 3 & 4), demonstrating a greater than three-fold selectivity for Myc-Max heterodimers.

Next, the activity of JY-3-094, the structure shown below, in Myc-overexpressing cell lines was investigated.

Daudi Burkitt lymphoma cells and HL60 promyelocytic leukaemia cells both express high levels of Myc. The lead compound 10074-G5 performs well in these cell lines, with $IC_{50}$ values of about 30 μM in HL60 cells and about 10 μM in Daudi cells (22). JY-3-094 demonstrated no cytotoxicities toward these cell lines, with $IC_{50}$s>100 μM in both HL60 and Daudi cells. This lack of cytotoxicity has been theorized to be ascribed to its charged carboxylic acid that inhibits cell entry. This was remedied by esterifying the carboxylic acid to generate a series of ester pro-drugs, all of which exhibited low micromolar $IC_{50}$ values in the above cell lines as shown hereinbelow. Whereas this proved an effective strategy for enhancing the cellular activity of c-Myc-Max inhibitor JY-3-094, the activity of the pro-drug will always be limited by the activity of its acid metabolite, if formed during metabolism.

However, further efforts to optimize 10074-G5 has found that a phenol ester pro-drug of JY-3-094, namely SF-4-017, is itself also a potent inhibitor of c-Myc-Max dimerization.

Importantly, the 7-nitro group and 1,2,5-oxadiazole of the benzofurazan moiety are both crucial for activity. Furthermore, a substituted aniline (or phenol) is necessary at the 4-position of the benzofurazan: ortho-substitution requires a bulky, hydrophobic group; para-substitution requires a carboxylic acid function. Re-introduction of the ortho-phenyl ring into the Myc inhibitor JY-3-provides for further improvement in Myc inhibitory activity through restoration of interactions with the hydrophobic pocket created by Phe375 and Ile381. In fact, the incorporation of especially hydrophobic groups to target the aforementioned hydrophobic pocket will be facilitated by the ionizable carboxylic acid that promotes the solubility of JY-3-094. Tables 3, 4, 6 and 7 provide for additional analogues of JY-3-094.

Ester Prodrugs of JY-3-094

In order to realize c-Myc inhibitory activity within cells, the carboxylic acid of JY-3-094 was esterified either by HBTU-mediated coupling of the acid to the appropriate alcohol, or by direct alkylation of the acid with the relevant bromide or iodide. Temporarily blocking a carboxylic acid as a metabolically-labile ester prodrug has been found to impart cell permeability to an otherwise cell impervious compound. The panel of ester pro-drugs that was prepared according to the synthesis as shown in Scheme 2 below with the results shown in Table 3A.

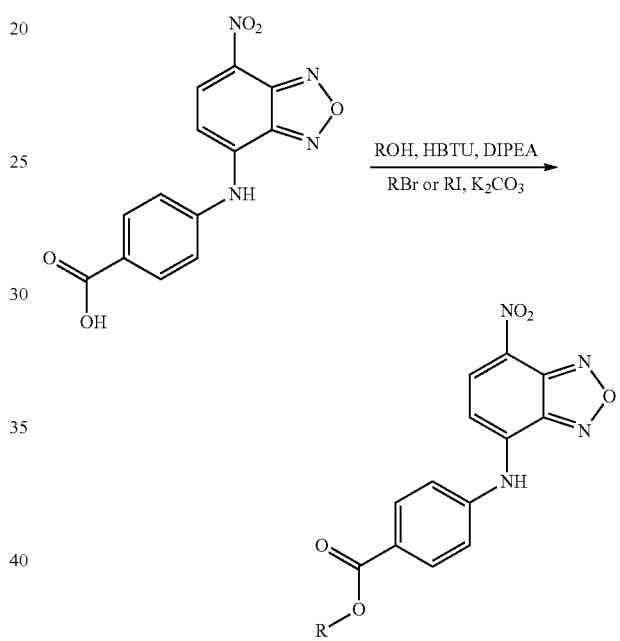

Figure 5:
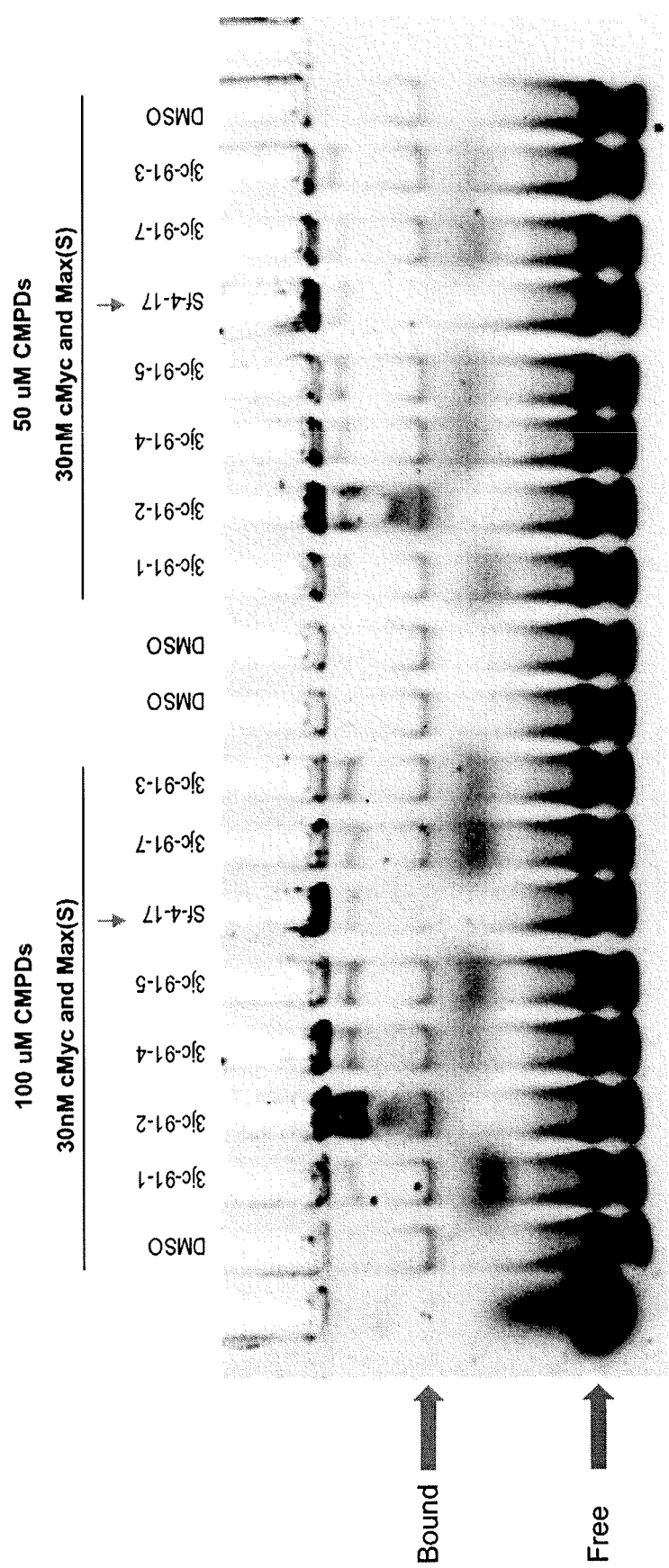
FIG. 5 shows the in vitro EMSA screen of prodrugs for their abilities to disrupt c-Myc-Max dimerization.

However, in most cases, blocking the carboxylic acid function of JY-3-094 led to a loss of c-Myc-Max dimerization inhibition, as assessed by an in vitro EMSA assay (FIG. 5).

Figure 6:
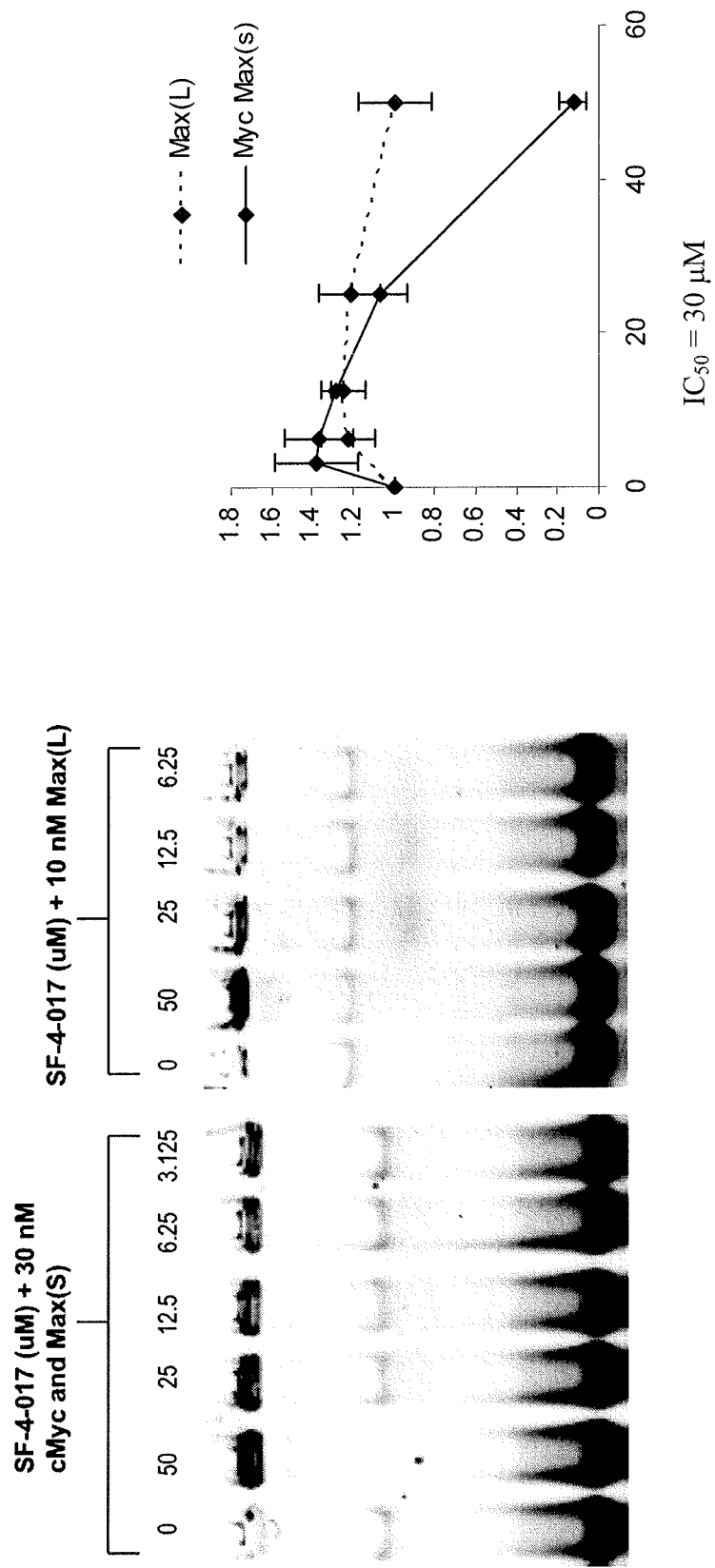
FIG. 6 shows the EMSA results performed with Myc-Max (S) heterodimers, representative EMSA performed with Max (L) homodimers (blots) and that SF-4-017 exhibits a dose response effect for inhibition of c-Myc-Max heterodimers ($IC_{50}=30$ uM).

Importantly and surprisingly, in the case of SF-4-017 (the phenol ester pro-drug and structure shown below),

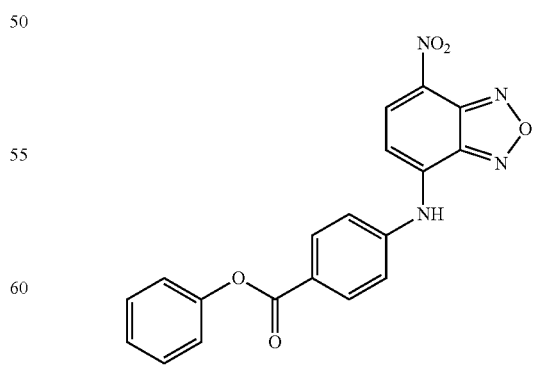

the inhibition of c-Myc-Max dimerization in vitro was found to be approximately as potent as the parent compound JY-3-094 ($IC_{50}$=30 μM), as shown in FIG. 6.

This finding coupled with the fact that SF-4-017, like all of the ester pro-drugs, exhibited much-improved cell activity in the c-Myc overexpressing HL60 and Daudi cells (FIG. 7) relative to JY-3-094 and these results suggest that SF-4-017 represents a new lead c-Myc inhibitor that is active in cells.

Figure 8:
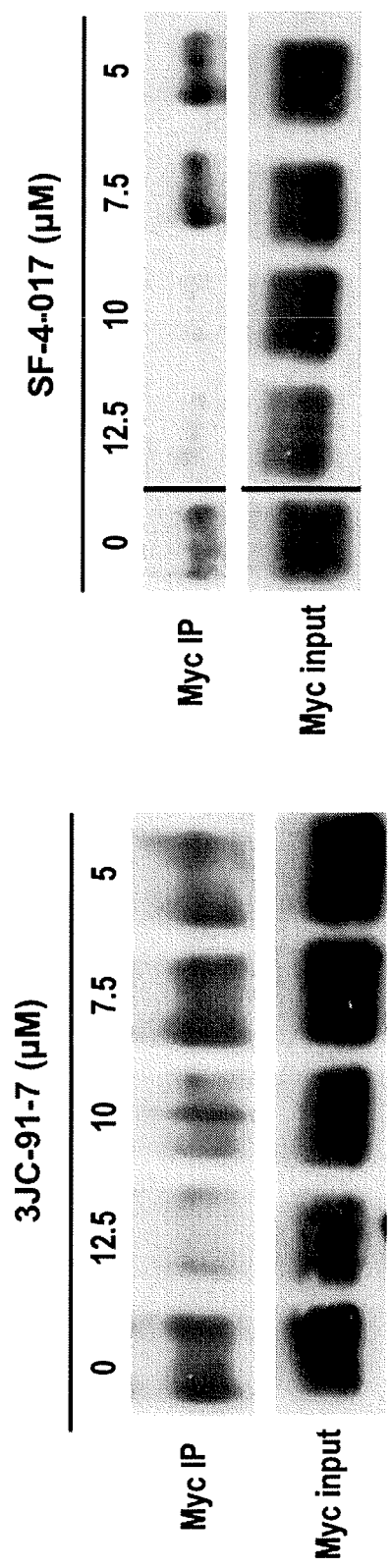
FIG. 8 shows the co-IPs of 3jc91-7 and SF-4-017 that demonstrate these compounds inhibit c-Myc-Max dimerization in cells.

Finally, several of the ester pro-drugs were subjected to co-IP experiments in cells, and were found to bind c-Myc, suggesting that their cytotoxic effects, at least in part, are due to their anticipated metabolism within cells to the c-Myc inhibitor JY-3-094 (FIG. 8).

Nitro and Carboxylic Acid Bioisosteres of JY-3-094 (and 10074-G5)

Aromatic nitro groups in drug molecules are often readily reduced in vivo to toxic metabolites, such as the highly nucleophilic hydroxylamine derivatives. The nitro group in 10074-G5 is no exception. The final reduction product of an aryl nitro species is the corresponding aniline. The aniline analogue of 10074-G5 was prepared and it was observed that the Myc-Max inhibitory activity was abolished, indicating the importance of the nitro group. It was found that functionalization of the aniline group with diglycolic anhydride led to almost a complete restoration in Myc-Max disruption. It is pertinent to identify functional nitro group bioisosteres of JY-3-094. Elmore and co-workers of Abbott Laboratories (36) have shown bioisosteric replacements for the nitro group in ABT-737, and have shown that a trifluoromethylsulfonyl group represents a functional bioisostere. Diglycoleamate also appears to be a good nitro group bioisostere. In addition to synthesizing these derivatives of JY-3-094 (Table 6) a variety of other potential nitro group replacements can be synthesized, many of which recapitulate the trigonal planar geometry of the nitro group with electron rich heteroatoms that are predicted to make contacts with Arg366 and Arg367 analogous to the nitro group in 10074-G5. The introduction of a sulfonyl group (Table 6) is particularly interesting as the +6 oxidation state of the sulfur atom allows for the attachment of further functionality that can engage in additional interactions with Myc in the region Asp363-Gln368. Likewise with the oxazole derivative of Table 6.

The carboxylic acid of JY-3-094 can be modified. The acid is critical to Myc-Max inhibition, possibly interacting with Arg378, since its esterification can abolish activity. However, the phenyl amide analogue in Table 7 (R=Ph, X=NO$_2$) exhibited moderate inhibitory activity of Myc-Max dimerization and, unlike JY-3-094, also demonstrated good cytotoxicity towards HL60 and Daudi cells, indicating that amidation of the acid of JY-3-094 can be a viable means towards improving cell activity. Furthermore, the introduction of the aniline moiety provides an opportunity to achieve additional interactions with the Myc protein, particularly in the region Phe374-Ile381, whose predominantly hydrophobic nature dictates the incorporation of hydrophobic anilines into JY-3-094. Complementary to this approach, the carboxylic acid of JY-3-094 can be modified to hydroxyisoxazole (Table 7), since hydroxyisoxazoles are known bioisosteres of carboxylic acids. Unlike the acid in JY-3-094, however, the hydroxisoxazole motif can add additional functionality to target Phe374-Ile381 whilst keeping the ionizable group intact—this can prove particularly important with more hydrophobic molecules. Similarly, the acylsulfonamide compound analogue in Table 7 is also a carboxylic acid bioisostere that allows for the introduction of additional functionality.

One of the attractions of 10074-G5 as a lead compound is that it can be accessed in just one chemical reaction from commercially available starting materials, which facilitates its optimization. Accordingly, the 2-aminobiphenyl (FIG. 1) was first modified through nucleophilic aromatic substitutions (S$_N$Ar) of 4-chloro-7-nitrobenzo[c][1,2,5]oxadiazole 2 with various anilines. In instances where the aniline was hindered and/or electronically deactivated, the coupling with 2 failed and so the more reactive 4-fluoro-7-nitrobenzo[c][1,2,5]oxadiazole(34) 3 was synthesized as previously described and then employed as the aryl halide coupling partner. Reduction of the nitro group delivered compound 4, which was smoothly acylated and acoylated to furnish compounds 5. Finally, S$_N$Ar reactions of aryl fluorides and chlorides 6 with 2-aminobiphenyl generated the library of compounds 7 wherein the nitrobenzofurazan was varied, as shown in Scheme 3, below.

Scheme 3.

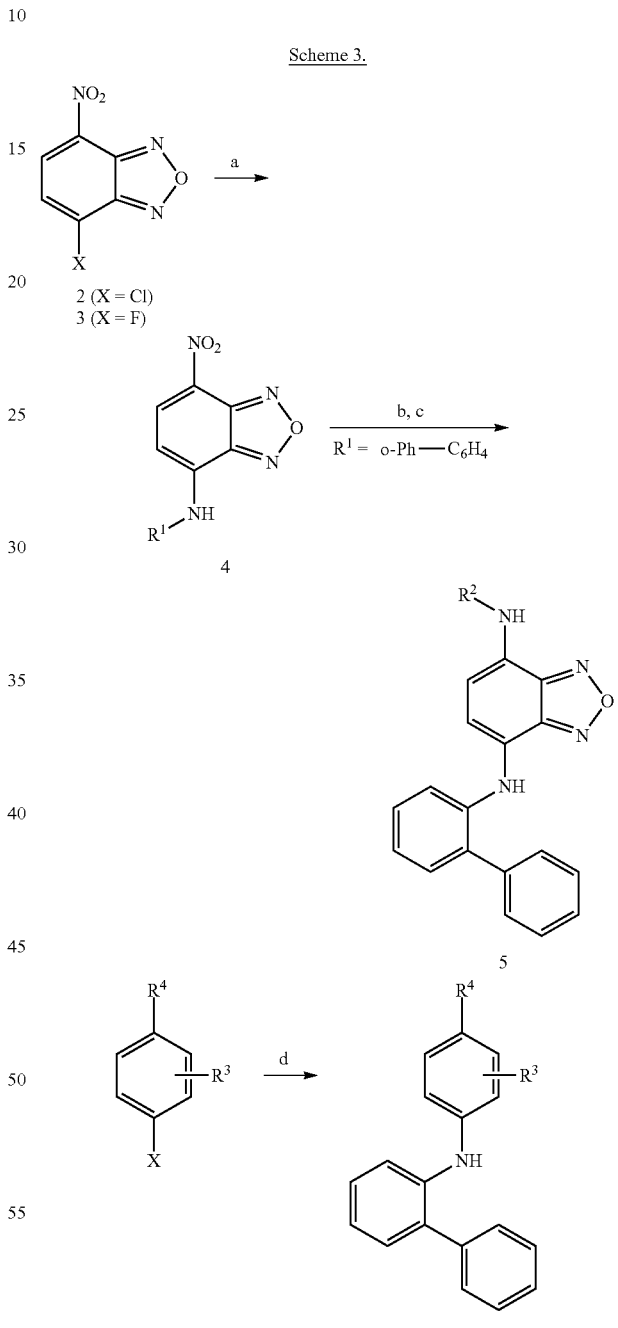

(a) R$^1$NH$_2$, CH$_3$CN, reflux, 16-20 h, 35-99%; (b) H$_2$, 10% Pd/C, MeOH, RT, 16 h, 76%; (c) R$^2$COX, Et$_3$N, CH$_2$Cl$_2$, 0° C. to RT, 16 h, 38-95%; (d) 2-aminobiphenyl, KOtBu, DMSO, 16 h.

Figure 9:
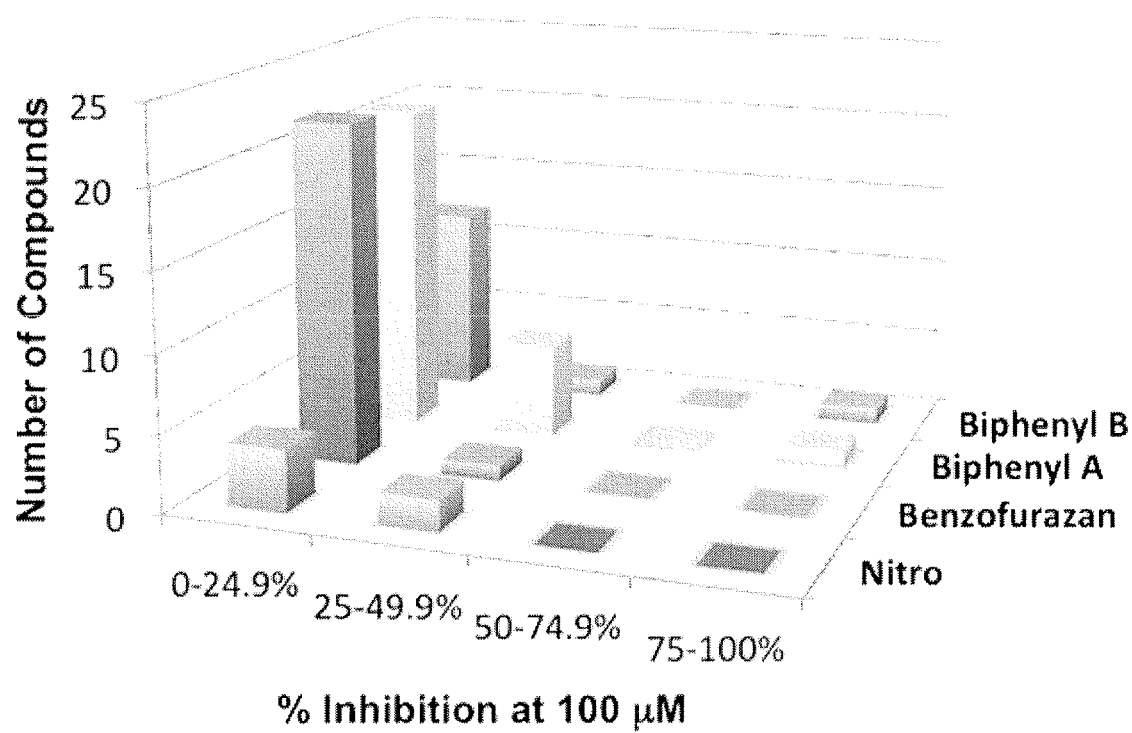
FIG. 9 shows the library members of 10074-G5 analogues that were screened for their abilities to inhibit c-Myc-Max dimerization at 100 uM, according to an EMSA assay. Labels on the right refer to the moiety of 10074-G5 was varied. "Biphenyl A" means the 2-aminobiphenyl was varied to mostly other 2-aminobiphenyls, as well as a few 3-aminobiphenyls, whereas "Biphenyl B" means the 2-aminobiphenyl was varied to a series of anilines. Full chemical structures and % inhibitions given in SI.

The ability of a small-molecule to interfere with c-Myc-Max dimerization is conveniently assessed through the disruption of the c-Myc-Max/DNA ternary complex by an electrophoretic mobility shift assay (EMSA) using fluorescently-labelled DNA, and subsequently quantified by densitometry. (23) Accordingly, a 100-member library was screened for the ability to disrupt the c-Myc-Max dimer. The c-Myc inhibitors 10074-G5 and JY-3-094 were included as positive controls. Consistent with other reports on the quest to identify c-Myc inhibitors,(22, 24-28) the "hit rate" of the 100 member library was rather low. As shown in FIG. 9, only 13 compounds effected ≥25% disruption of c-Myc-Max dimerization at 100 uM. Tables 10 and 11 provide full details on % disruption of c-Myc-Max dimerization at 100 uM. Several of the more promising compounds identified by this assay (typically, those that achieved ≥50% inhibition) were selected for further evaluation to determine $IC_{50}$ values for the disruption of c-Myc-Max dimerization and Max-Max dimerization, and this data is presented in Table 8.

SF-3-103B (Table 11) was the only active member (≥33% inhibition of c-Myc-Max) of a subset of about 20 compounds that investigated the effect of the structural variation of the benzofurazan moiety. The $IC_{50}$ value for SF-3-103B was subsequently calculated to be 84 uM, which is nearly two-fold more potent than the lead 10074-G5. As the solitary active compound in this particular subset, these findings are consistent with earlier reports on a focused group of congeners that the nitro group and furazan ring are essential components of 10074-G5 for c-Myc-Max inhibitory activity. The half-life of 10074-G5 in blood plasma is short ($t_{1/2}$=37 min), and this is believed to be partially due to reduction of the nitro group to the corresponding primary amine, (35) which has been previously shown to be inactive.(32)

The discovery that hydrophobic groups at the ortho position of the 2-aminobiphenyl are favoured whilst a carboxylic acid is preferred at the para position prompted the preparation of a library of compounds incorporating both of these functionalities, in combination, to provide more potent compounds. The amalgamation of a para-carboxylic acid, as in JY-3-094, and various ortho-aryl (and a few meta-aryl) moieties, as in 10074-G5, afforded a library of about 20 compounds, but did not furnish any inhibitors of c-Myc-Max dimerization ($IC_{50}$>100 uM). An example of one such compound is 3jc53-6 (Table 10). A lack of additivity is not unusual in drug design, but it is surprising that a complete loss in inhibitory activity was observed. Since monomeric c-Myc is unstructured and small-molecule inhibitors of c-Myc create their own binding sites, it is possible that JY-3-094 and 10074-G5 craft different binding pockets, neither of which can accommodate the additional functionality from the other small-molecule. Several of the methyl ester precursors to this series of compounds were screened and such screening identified 3jc48-3 (Table 10) with an $IC_{50}$ value of 34.8 uM for the disruption of c-Myc-Max heterodimerization. This represents an approximately five-fold improvement over the parent compound and a two-fold selectivity over the inhibition of Max-Max homodimerization. Analogue 4jc23-4 (also in Table 10) exhibited a two-fold reduction in c-Myc-Max inhibitory activity, relative to 3jc48-3, indicating that the $CF_3$ group is poorly bioisosteric, in agreement with a recent study that re-assessed the controversial bioisosterism of the $CF_3$ group.(37) Since 3jc53-6 is inactive in vitro and methyl ester 3jc48-3 is likely metabolized to 3jc53-6 in cells, it may be important to replace the methyl ester with more hindered, metabolically stable esters and/or amide isosteres.

Replacement of the ortho-phenyl ring in 10074-G5 with a para-carboxylic acid furnished JY-3-094, which, as previously stated, resulted in an improvement in c-Myc-Max dimerization inhibition of around five-fold ($IC_{50}$=33 uM). JY-3-094 is also at least three-fold selective for c-Myc-Max heterodimers over Max-Max homodimers. Esterification of the carboxylic acid of JY-3-094 resulted in phenyl ester SF-4-017 that retained the inhibitory activity of JY-3-094 in vitro. (33) Notably SF-4-017 functions in cells as a pro-drug of JY-3-094, and, therefore, the inhibitory activity of SF-4-017 is limited to that of its metabolite JY-3-094. Thus, it would be effective to prepare metabolically more stable amide derivatives to ensure the pro-drug form would persist for longer. Accordingly, phenyl amide JY-5-195 (shown in Table 8) was synthesized, which proved similarly active in vitro to SF-4-017, indicating that amidation of the carboxylic acid of JY-3-094 is a viable route towards the further optimization of 10074-G5. This was further validated by the data for amide JY-5-261 (Table 8) ($IC_{50}$=71 uM).

The cellular activities of the lead inhibitors of c-Myc-Max dimerization was evaluated in the c-Myc overexpressing HL60 and Daudi cell lines using a standard MTT assay. As Table 9 shows, 10074-G5 was moderately inhibitory towards both HL60 and Daudi cells, with $IC_{50}$ values of 10 uM and 30 uM, respectively. JY-3-094, SF-3-103B and 3jc53-6 were all inactive in these cell lines, which is presumably a consequence of their carboxylic acid functionalities whose charges at physiological pH impede cell permeation. In keeping with this hypothesis, esterification and amidation of the carboxylic acid of JY-3-094 afforded compounds SF-4-017, JY-5-195 and JY-5-261 that inhibited HL60 and Daudi cells with much-improved, single-digit micromolar $IC_{50}$ values. 3jc48-3 was also particularly inhibitory in both cell lines with $IC_{50}$ values of 3.8 uM (HL60) and 1.3 uM (Daudi). Trifluoromethyl-biphenyl compound 4jc23-4 proved especially cytotoxic, with $IC_{50}$ values of 877 nM against HL60 cells and 500 nM against Daudi cells. However, upon comparing the in vitro and cell data for congeners 3jc48-3 and 4jc23-4, it is surmised that 4jc23-4 has significant off-target effects, which is likely due to the particularly lipophilic/hydrophobic $CF_3$ group (c Log Ps: 6.46 (3jc48-3) and 6.84 (4jc23-4)). In order to maintain specificity for c-Myc, as well as to enhance inhibitory activity, it may be preferable to ensure the c Log P of future 10074-G5 analogues is maintained at or below 6.46.

Figure 10:
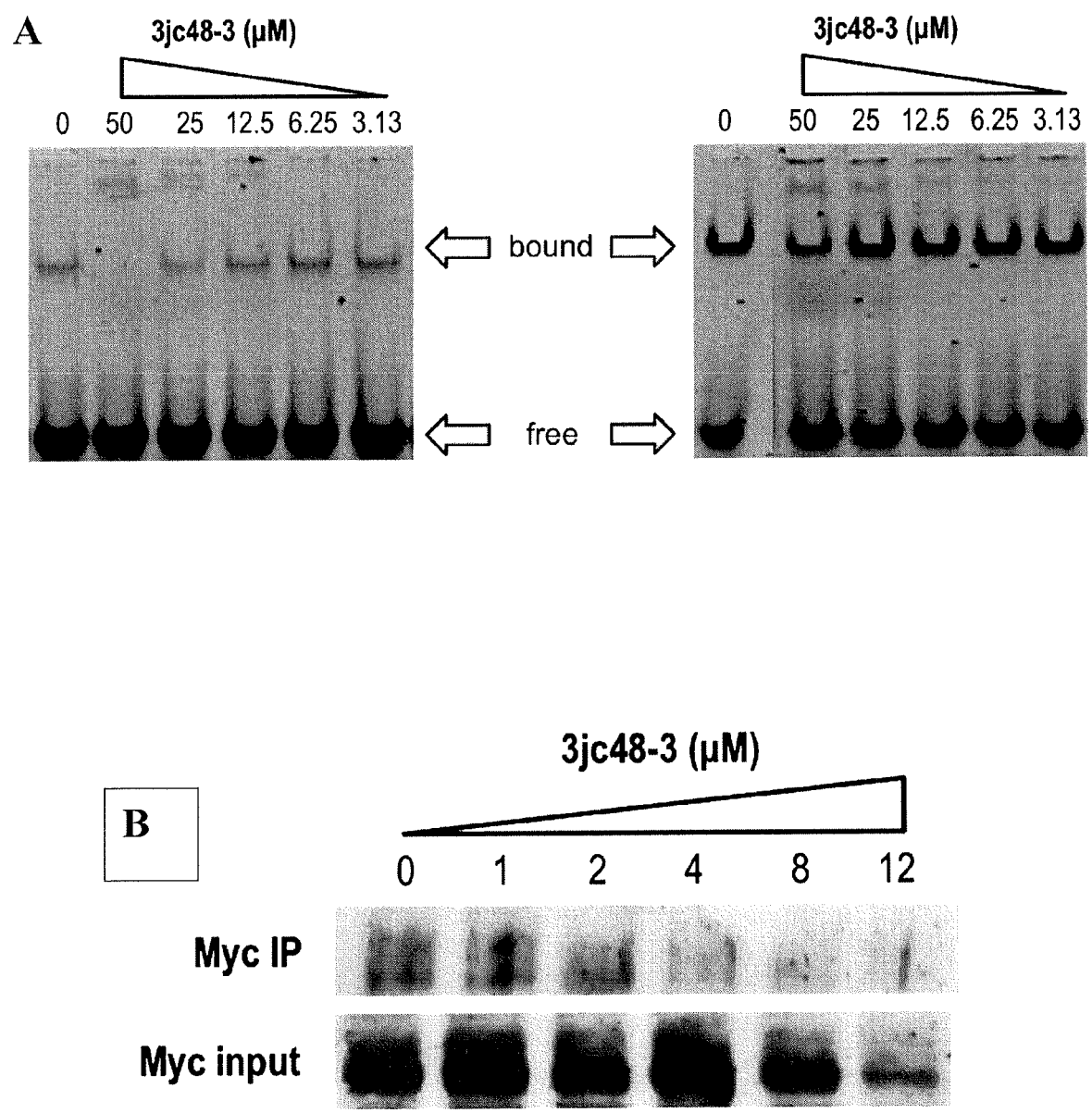
FIG. 10 shows the biological characterization of 3jc48-3. A. 3jc48-3 inhibits c-Myc-Max dimerization (left) and is about two-fold selective for c-Myc-Max heterodimers over Max-Max homodimers (right), as analysed by an EMSA. Either 30 nM of each of c-Myc and Max or 60 nM of Max incubated with 20 nM 5'-hexachlorofluoresceine-CACCCG-GTCACGTGGCCTACAC-3' (SEQ ID NO: 1) and the indicated concentrations of 3jc48-3. B. Co-immunoprecipitation. 3jc48-3 was incubated with $5 \times 10^6$ HL60 cells at the concentrations indicated. After 7 h, the cells were pelleted by centrifugation, washed and lysed. Total Max was precipitated with polyclonal rabbit anti-Max antibody.
Figure 11:
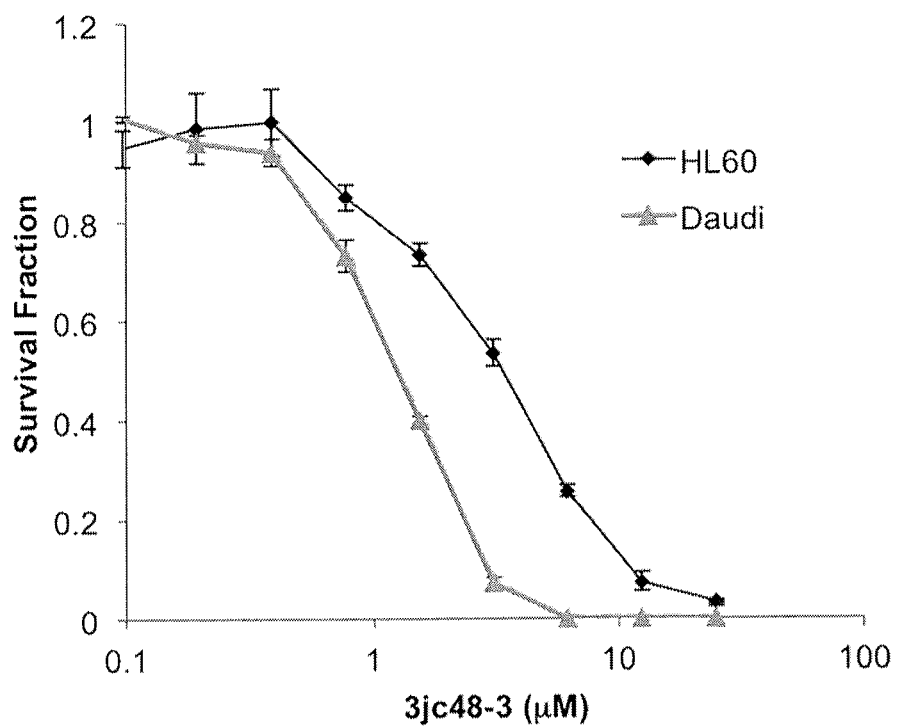
FIG. 11 shows the cytotoxicities of 3jc48-3 in HL60 and Daudi cells as determined at the indicated concentrations of 3jc48-3 after 72 h by the MTT assay.
Figure 12:
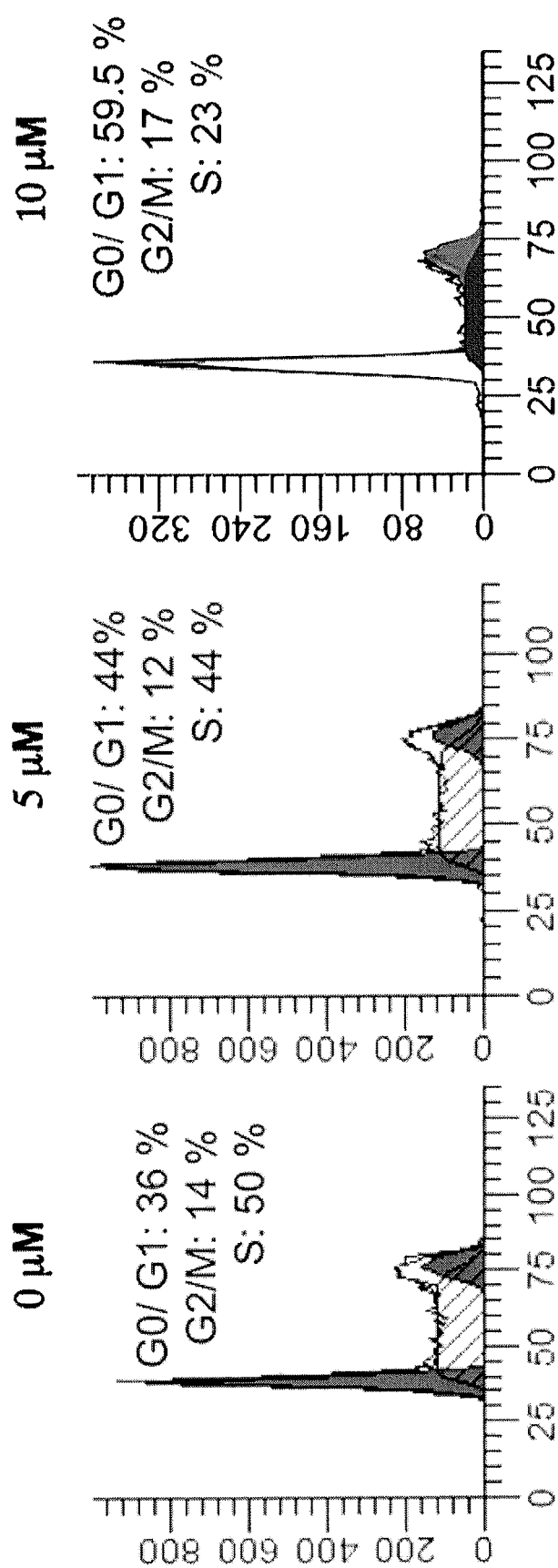
FIG. 12 shows that 3jc48-3 dose-dependently inhibits HL60 cell proliferation by blocking progression of the cell cycle beyond the G0/G1 phase after 24 h.
Figure 13:
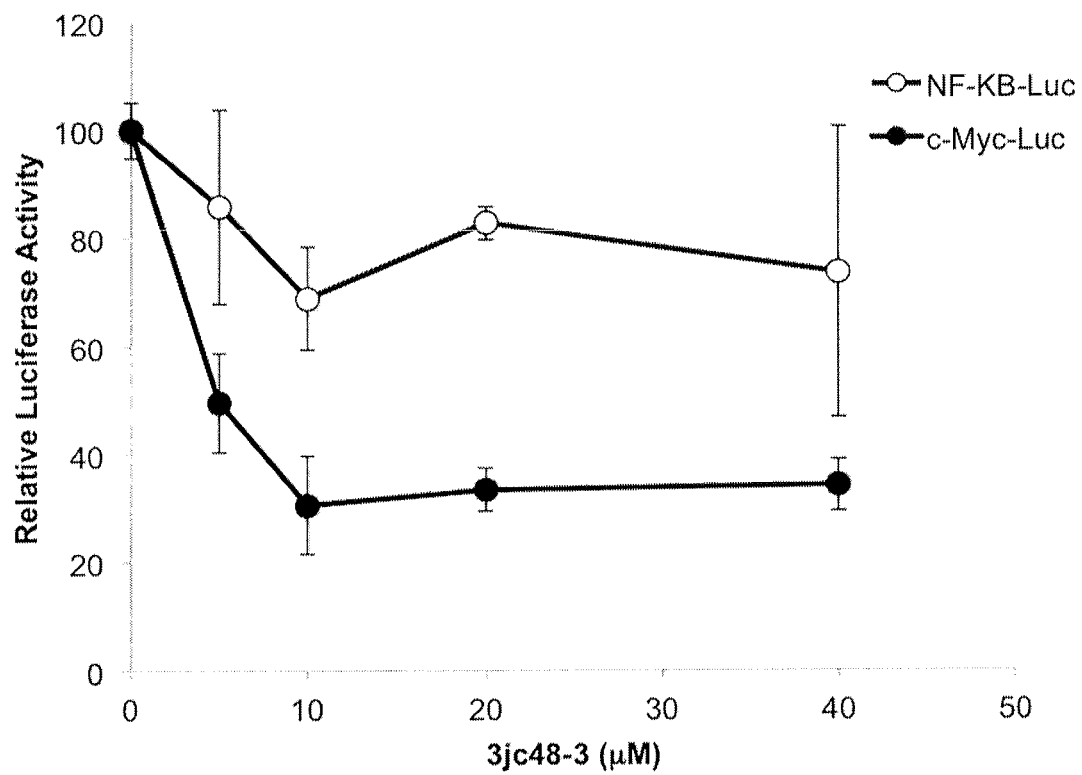
FIG. 13 shows that 3jc48-3 selectively inhibits the expression of the luciferase gene under the control of a c-Myc promoter.

Given their abilities to disrupt c-Myc-Max dimerization in vitro, it is likely that the cellular efficacies of the compounds described herein are, to some degree, due to their abilities to inhibit the transcriptional activity of c-Myc. To investigate this possibility, 3jc48-3 was selected for further biological characterization. To explore further the finding that 3jc48-3 disrupts c-Myc-Max dimerization in vitro (FIG. 10A, EMSA), a co-immunoprecipitation assay of 3jc48-3 in HL60 cells demonstrated that the inhibitor is capable of disrupting c-Myc-Max dimerization within cells (FIG. 10B). The origin of cell proliferation inhibition by 3jc48-3 (FIG. 11) was next investigated. In a cell-cycle arrest assay, 3jc48-3 dose-dependently increased the percentage of HL60 cells in the G0/G1 stage, indicating that the cells were growth-arrested, which is a typical response to c-Myc inhibition (FIG. 12). Finally, in an assay in which the expression of a highly unstable luciferase reporter is regulated by either a c-Myc-responsive or NF-κB-responsive promoter, 3jc48-3 selectively inhibited the c-Myc-driven gene causing luciferase activity to become markedly diminished within 6 h of compound addition (FIG. 13). Collectively, these data support the conclusion that the novel small-molecule 3jc48-3 causes cell death in c-Myc overexpressing cell lines through disruption of c-Myc transcriptional activity by inhibiting c-Myc-Max dimerization.

Towards the optimization of the c-Myc inhibitor 10074-G5, efforts to combine the ortho-phenyl ring of 10074-G5 and the para-carboxylic acid of JY-3-094 led to the discovery of 3jc48-3, which is one of the most potent inhibitors of c-Myc-Max dimerization in vitro ($IC_{50}$=34.8 uM) and in cells reported to date. Furthermore, 3jc48-3 inhibits the proliferation of HL60 and Daudi cells with single-digit micromolar $IC_{50}$ values in a manner that correlates with blocking cell cycle progression beyond the G0/G1 phase. Additional conformation that 3jc48-3 is an inhibitor of c-Myc was provided by the selective inhibition of a c-Myc-responsive luciferase reporter. In tandem with this optimization strategy, it is shown that esterification of the carboxylic acid of JY-3-094 is an effective approach towards enhancing the cell activity of a poorly cell permeable c-Myc-Max dimerization inhibitor. However, this tactic represents an impasse since the inhibitory activity of the ester pro-drug will be limited by that of the acid metabolite JY-3-094 ($IC_{50}$=33 uM). Therefore, metabolically more stable amide isosteres were prepared, such as JY-5-195 and JY-5-261 described above, and found some of these to be potent inhibitors of c-Myc-Max dimerization as well as effective proliferation inhibitors of HL60 and Daudi cells.

The compounds described herein can be used to treat a subject, such as a patient, with a cancer that implicates c-Myc. Increased activity by c-Myc is broadly known for its central role in many cancers. Non-limiting examples of diseases implicating a role of c-Myc include: Burkitt's lymphoma, non-Burkitt's lymphoma, prostate cancer; breast cancer; gastrointestinal cancer; melanoma; multiple myeloma; and myeloid leukemia. As shown herein, the compounds and compositions described herein are shown to directly affect growth of members of this group, including myeloid Leukemia (HL-60) cells. As such, methods are provided for reducing cell growth rates of tumor (proliferating) cells in a subject (e.g., patient, or a human subject or patient) having a cancer in which interference with c-Myc expression, e.g., interference with Myc-Max binding results in decreased growth rate of the tumor cells, which is readily determinable by a person of ordinary skill using the binding assays and/or growth assays, such as the fluorescent polarization, EMSA and MTT assays described herein. As indicated above, and in the data presented herein, those cancers include, without limitation one or more of Burkitt's lymphoma; non-Burkitt's lymphoma; prostate cancer; breast cancer; gastrointestinal cancer; melanoma; multiple myeloma; and myeloid leukemia.

As used herein, "pharmaceutically acceptable," means acceptable for use in humans and animals. "Excipients" include, without limitation, one or more suitable: vehicle(s), solvent(s), diluent(s), pH modifier(s), buffer(s), salt(s), colorant(s), rheology modifier(s), lubricant(s), filler(s), antifoaming agent(s), erodeable polymer(s), hydrogel(s), surfactant(s), emulsifier(s), adjuvant(s), preservative(s), phospholipid(s), fatty acid(s), mono-, di- and tri-glyceride(s) and derivatives thereof, wax(es), oil(s) and water. The choice of excipient depends on the dosage form in question.

The compounds described herein may be administered by any effective route. Typical administration routes for anti-cancer drugs include, without limitation, oral and parenteral routes, such as intravenous (IV) injection. The compounds described herein are useful in interfering with c-Myc and Max association. A typical dosage form would contain an amount of a compound effective to inhibit cell growth to a desired extent and a pharmaceutically acceptable excipient or excipients. This amount would naturally vary depending on the specific activity of the compound, the delivery route and the choice of solubilizing agents, among other factors. For example, a dosage form might include about 1 µg per kg of a patient's body weight to about 1 mg per kg of the patient's body weight of the compound, effective ranges might be narrower to range from about 100 µg per kg of patient body weight to about 1 mg per kg of patient body weight. In any case, as used herein, any agent used for interfering with Myc and Max association is administered in an amount effective to slow or stop growth of a cell in an amount and in a dosage regimen effective to prevent, reduce the rate of cellular growth.

Parenteral administration may require at a minimum buffers and salts to match physiological conditions, and thus, includes salt and buffer, such as, without limitation, normal saline or phosphate-buffered saline. Depending on the solubility of the compound (active ingredient), the dosage form may be aqueous, micellular (including liposomes) or lipophilic. Formulation of a drug product and choice of suitable excipient(s) with adequate bioavailability is within the average skill of those in the pharmaceutical and formulary arts. For example and without limitation, an HCl salt of a compound described herein may be administered intravenously or intramuscularly in normal saline, or may be administered in tablet or capsule form with appropriate excipients. A large variety of dosage forms are known in the pharmaceutical arts, and many of which may be appropriate for treatment using the methods and compositions described herein (see generally, Troy, D B, Editor, Remington: The Science and Practice of Pharmacy, $21^{st}$ Edition, Lippincott, Williams & Wilkins (2005)).

Different excipients or reagent systems, dosage forms, administration routes and salt or free-base forms of the active ingredients would be expected to affect bioavailability and the specific activity of the active agent, and thus the ability of any given active ingredient to decrease cellular growth rates in an individual. Administration of different amounts or concentrations of the active ingredient using different dosage regimens will achieve similar results, with the drug product administered, typically and without limitation, from one to ten times daily, including 2, 3, 4, 5, 6, 7, 8, 9 and 10 times daily. The amount of the drug product administered to the subject, also may vary depending on the dosage form. A person of average skill in the pharmaceutical and medical arts will appreciate that it will be a matter of simple design choice and optimization to identify a suitable dosage regimen for treatment of any given disease state (e.g., cancer).

Pharmaceutically acceptable salts are, because their solubility in water is greater than that of the initial or basic compounds, particularly suitable for medical applications. These salts have a pharmaceutically acceptable anion or cation. Suitable pharmaceutically acceptable acid addition salts of the compounds of the invention include, without limitation, salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts include without limitation, ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine. Pharmaceutically acceptable salts may be prepared from parent compounds by any useful method, as are well known in the chemistry and pharmaceutical arts.

Methods

All chemicals were purchased from Sigma-Aldrich, VWR or Oakwood Chemicals. Anhydrous solvents were purchased from Sigma-Aldrich and used without further purification.

10074-G5 was purchased from Santa Cruz Biotech. All reactions were performed with oven-dried glassware and under an inert atmosphere of $N_2$. Crude material was purified using silica gel flash column chromatography. Purities of final compounds were >90% as assessed by a Waters 2535 Quaternary Reverse Phase HPLC, using a λ=214 nm and a gradient of 100% solvent A to 100% solvent B over 22 min followed by holding at 100% B for 8 min (solvent A=100:0.1, $H_2O$/TFA; solvent B=90:10:0.1, ACN/$H_2O$/TFA). Purities are stated after retention times, $t_R$. NMR spectra were calibrated to residual proton isotopic peaks (CDCl$_3$: $\delta_H$=7.26, $\delta_C$=77.23; d$_6$-DMSO: $\delta_H$=2.50, $\delta_C$=39.51).

General Procedure to Prepare Compounds 10074-G5 and 3a-3q

To a solution of 4-chloro-7-nitrobenzofurazan (NBD-Cl, 2; 1 eq.) in acetonitrile (0.1 M) was added the requisite amine (1.1 eq.) followed by triethylamine (2 eq.). The reaction mixture was then stirred at reflux under an inert atmosphere ($N_2$) for 16 h. The solvent was removed in vacuo, then the residue was re-dissolved in EtOAc, washed with 1 M HCl, water, brine, dried ($Na_2SO_4$), filtered and concentrated. The crude material was purified over silica gel, eluting with a gradient of EtOAc in Hexanes.

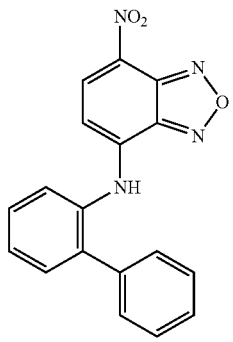

10074-G5

N-([1,1'-Biphenyl]-2-yl)-7-nitrobenzo[c][1,2,5]oxadiazol-4-amine (10074-G5): yield=300 mg, 90%; brick-red solid; $^1$H NMR (400 MHz; DMSO-d$_6$) $\delta_H$ 11.01 (1H, s, Ar—H), 8.38 (1H, d, Ar—H, J=9 Hz), 7.55-7.23 (9H, m, Ar—H), 6.06 (1H, d, Ar—H, J=9 Hz); $^{13}$C NMR (100 MHz; DMSO-d$_6$) $\delta_C$ 144.6, 144.4, 139.2, 138.5, 137.9, 134.9, 131.7, 129.4, 129.1, 128.9, 128.8, 128.5, 127.9, 122.4, 102.2; m/z (ESI) 333.0 (M+H)$^+$.

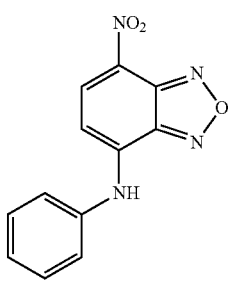

3a

7-Nitro-N-phenylbenzo[c][1,2,5]oxadiazol-4-amine (3a): yield=223 mg, 87%; red solid; $^1$H NMR (400 MHz; DMSO-d$_6$, TMS) $\delta_H$ 11.05 (1H, s, Ar—NH), 8.54 (1H, d, Ar—H, J=9 Hz), 7.54-7.5 (4H, m, Ar—H), 7.33 (1H, t, Ar—H, J=6 Hz), 6.72 (1H, d, Ar—H, J=9 Hz); $^{13}$C NMR (100 MHz; CDCl$_3$) $\delta_C$ 144.7, 143.8, 141.1, 136.6, 136, 130.1, 127.3, 125.6, 123.6, 100.9; m/z (ESI) 257.0 (M+H)$^+$.

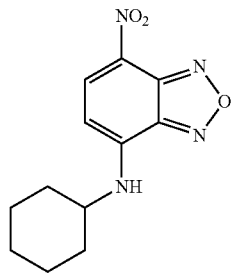

3b

N-Cyclohexyl-7-nitrobenzo[c][1,2,5]oxadiazol-4-amine (3b): yield=142 mg, 43%; red solid; $^1$H NMR (500 MHz; CDCl$_3$) $\delta_H$ 8.42 (1H, d, Ar—H, J=8.8 Hz), 6.25 (1H, d. Ar—NH, J=5.6 Hz), 6.17 (1H, d, Ar—H, J=8.8 Hz), 3.66 (1H, s, CH$_2$), 2.14 (2H, s, CH$_2$), 1.84 (2H, s, CH$_2$), 1.70 (1H, d, CH, J=6.0 Hz), 1.43 (4H, m, (CH$_2$)$_2$), 1.29 (1H, s, CH); $^{13}$C NMR (100 MHz; CDCl$_3$) $\delta_C$ 144.3 143.9, 143, 136.6, 123.2, 98.6, 52.9, 32.1, 25.1, 24.5 m/z (ESI) 263.0 (M+H)$^+$.

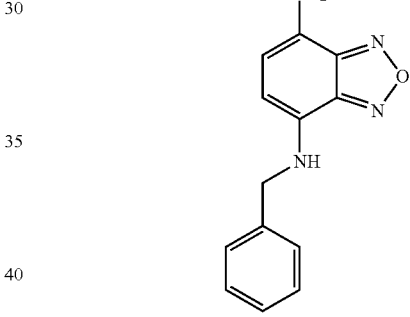

3c

N-Benzyl-7-nitrobenzo[c][1,2,5]oxadiazol-4-amine (3c): yield=217 mg, 64%; red solid; $^1$H NMR (400 MHz; DMSO-d$_6$) $\delta_H$ 9.98 (1H, s, Ar—NH), 8.48 (1H, d, Ar—H, J=7.8 Hz), 7.42-7.25 (5H, m, Ph), 6.36 (1H, d, Ar—H, J=7.8 Hz), 4.72 (2H, s, CH$_2$); $^{13}$C NMR (100 MHz; CDCl$_3$) $\delta_C$ 145.8, 145.4, 145, 138.7, 137.8, 129.5, 128.3, 128.2, 128, 122.2, 100.6, 47.2; m/z (ESI) 271 (M+H)$^+$.

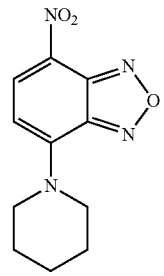

3d

4-Nitro-7-(piperidin-1-yl)benzo[c][1,2,5]oxadiazole (3d): yield=307 mg, 99%; red solid; $^1$H NMR (500 MHz; DMSO-d$_6$) $\delta_H$ 8.45 (1H, d, Ar—H, J=8.7 Hz), 6.65 (1H, d, Ar—H, J=8.7 Hz), 4.14 (4H, s, 2(C$\underline{H}_2$)), 1.74 (6H, s, 3×C$\underline{H}_2$); $^{13}$C NMR (100 MHz; CDCl$_3$) $\delta_C$ 145.1, 144.9, 144.7, 135.4, 101.9, 51.2, 26, 23.9; m/z (ESI) 249.0 (M+H)$^+$.

152.7, 144.8, 144.5, 144.1, 138, 129.3, 127.8, 124.5, 122.3, 120, 117.3, 102.6; m/z (ESI) 295.2 (M+Na)$^+$.

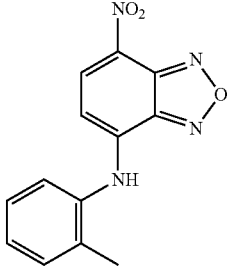

3e

7-Nitro-N-(o-tolyl)benzo[c][1,2,5]oxadiazol-4-amine (3e): yield=100 mg, 60%; red crystals; $^1$H NMR (400 MHz; DMSO-d$_6$) 8.39 (1H, d, Ar—$\underline{H}$, J=8.8 Hz), 7.58 (1H, s, Ar—N$\underline{H}$), 7.35 (4H, m, Ar—$\underline{H}$), 6.23 (1H, d, Ar—$\underline{H}$, J=8.8 Hz), 2.32 (3H, s, C$\underline{H}_3$); $^{13}$C-NMR (100 MHz; CDCl$_3$) 144.4, 143.9, 142, 136, 134.6, 134.2, 131.9, 128.4, 127.6, 125.9, 100.8, 29.6; m/z (ESI) 271.0 (M+H)$^+$.

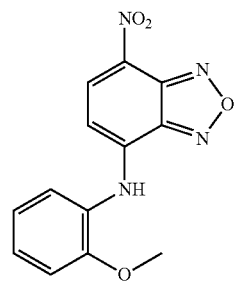

3h

N-(2-Methoxyphenyl)-7-nitrobenzo[c][1,2,5]oxadiazol-4-amine (3h): yield=205 mg, 70%; red crystals; $^1$H NMR (500 MHz; CDCl$_3$) $\delta_H$ 10.8 (1H, s, Ar—NH), 8.54 (1H, d, Ar—H, J=8.8 Hz), 7.48-7.41 (2H, m, Ar—H), 7.28 (1H, d, Ar—H, J=8.8 Hz), 7.12 (1H, t, Ar—H, J=7.4 Hz), 6.15 (1H, d, Ar—H, J=8.8 Hz), 3.83 (3H, s, OCH$_3$); $^{13}$C NMR (100 MHz; CDCl$_3$) $\delta_C$ 151.7, 145.3, 144.1, 140.4, 136.2, 127.4, 126.1, 122.1, 121.1, 111.9 101.2, 56.0; m/z (ESI): 309.0 (M+Na)$^+$.

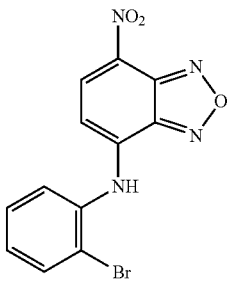

3f

N-(2-Bromophenyl)-7-nitrobenzo[c][1,2,5]oxadiazol-4-amine (3f): yield=44 mg, 13%; red solid; $^1$H NMR (400 MHz; DMSO-d$_6$) $\delta_H$ 10.97 (1H, s, Ar—H), 8.50 (1H, d, Ar—$\underline{H}$, J=8.6 Hz), 7.83 (1H, d, Ar—$\underline{H}$, J=8 Hz), 7.53 (2H, d, Ar—$\underline{H}$, J=4 Hz), 7.40-7.30 (1H, m, Ar—$\underline{H}$), 6.05 (1H, d, Ar—$\underline{H}$, J=8.6 Hz); $^{13}$C-NMR (100 MHz; DMSO-d$_6$) $\delta_C$ 144.7, 144.5, 143.7, 137.8, 136.7, 134.2, 130.4, 129.9, 129.7, 123.6, 121.8, 102.7; m/z (ESI) found 358.9 (M+Na)$^+$.

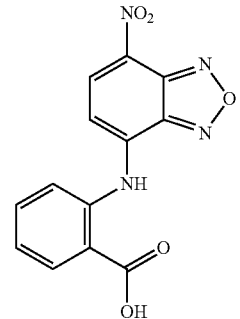

3i 2-((7-Nitrobenzo[c][1,2,5]oxadiazol-4-yl)amino)benzoic acid (3i): yield=466 mg, 99%; red solid; $^1$H NMR (400 MHz; DMSO-d$_6$) $\delta_H$ 8.56 (1H, d, Ar—$\underline{H}$, J=8.6 Hz), 8.07 (1H, d, Ar—$\underline{H}$, J=7.7 Hz), 7.77 (1H, d, Ar—$\underline{H}$, J=7.8 Hz), 7.71 (1H, t, Ar—$\underline{H}$, J=7.7 Hz), 7.36 (1H, t, Ar—$\underline{H}$, J=7.8 Hz), 6.95 (1H, d, Ar—$\underline{H}$, J=8.6 Hz); $^{13}$C NMR (100 MHz; DMSO-d$_6$) $\delta_C$ 168.7, 145.9, 144.3, 140.8, 139.4, 137.8, 134.4, 132.3, 125.8, 124.9, 123.2, 122.6, 103.7; m/z (ESI) 323.0 (M+Na)$^+$.

3g 2-((7-Nitrobenzo[c][1,2,5]oxadiazol-4-yl)amino)phenol (3g): yield=122 mg, 44%; dark red solid; $^1$H NMR (400 MHz; DMSO-d$_6$) $\delta_H$ 10.7 (1H, s, Ar—O$\underline{H}$), 10.0 (1H, s, Ar—N$\underline{H}$), 8.56 (1H, d, Ar—$\underline{H}$, J=9 Hz), 7.33-7.27 (2H, m, Ar—$\underline{H}$), 7.07 (1H, d, Ar—$\underline{H}$, J=8 Hz), 6.97 (1H, t, Ar—$\underline{H}$, J=7.2 Hz), 6.13 (1H, d, Ar—$\underline{H}$, J=9 Hz); $^{13}$C NMR (100 MHz; DMSO-d$_6$) $\delta_C$ 3j 4-([1,1'-Biphenyl]-2-yloxy)-7-nitrobenzo[c][1,2,5]oxadiazole (3j): yield=139 mg, 33%; yellow solid; $^1$H NMR (400 MHz; DMSO-d$_6$) $\delta_H$ 8.55 (1H, d, Ar—$\underline{H}$, J=8.6 Hz), 7.66-7.47 (6H, m, Ar—$\underline{H}$), 7.34-7.24 (3H, m, Ar—$\underline{H}$), 6.66 (1H, d, Ar—$\underline{H}$, J=8.6 Hz); $^{13}$C-NMR (100 MHz; CDCl$_3$); $\delta_C$ 153.6, 149.6, 144.7, 143.9, 135.7, 134.5, 133.2, 131.9, 130.2, 129.6, 128.62, 128.6, 128.1, 127.8, 121.9, 107.6; m/z found 356.0 (M+Na)$^+$.

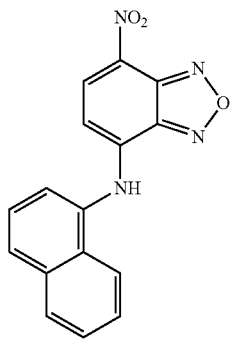
3k

N-(Naphthalen-1-yl)-7-nitrobenzo[c][1,2,5]oxadiazol-4-amine (3k): yield=109 mg, 35%; red solid; $^1$H NMR (400 MHz; DMSO-d$_6$) $\delta_H$ 11.3 (1H, s, Ar—NH), 8.48 (1H, d, Ar—H, J=9 Hz), 8.13-8.08 (2H, m, Ar—H), 7.98 (1H, d, Ar—H, J=8.4 Hz), 7.73-7.58 (4H, m, Ar—H), 6.01 (1H, d, Ar—H, J=9 Hz); $^{13}$C NMR (100 MHz; CDCl$_3$) $\delta_C$ 144.9, 144.6, 144.3, 137.6, 134.2, 133.5, 128.9, 128.5, 128.3, 127, 126.8, 126.1, 124.7, 122.8, 122.6, 101.9; m/z (ESI) 329.0 (M+Na)$^+$.

3l

N-([1,1'-Biphenyl]-4-yl)-7-nitrobenzo[c][1,2,5]oxadiazol-4-amine (3l): yield=261 mg, 78%; red crystals; $^1$H NMR (500 MHz; DMSO-d$_6$) $\delta_H$ 11.1 (1H, s, Ar—NH), 8.56 (1H, d, Ar—H, J=8.8 Hz), 7.77 (1H, s, Ar—H), 7.71 (2H, d, Ar—H, J=6.8 Hz), 7.62-7.58 (2H, app. t, Ar—H), 7.51-7.48 (3H, app. t, Ar—H), 7.41 (1H, t, Ar—H, J=7.6 Hz), 6.85 (1H, d, Ar—H, J=8.8 Hz); $^{13}$C NMR (100 MHz; DMSO-d$_6$) $\delta_C$ 146.1, 145.2, 143.3, 142.7, 140.3, 139.5, 138.8, 131.3, 130.1, 129, 127.8, 125.7, 124.2, 123.7, 123, 103.1; m/z (ESI) 333.0 (M+H)$^+$.

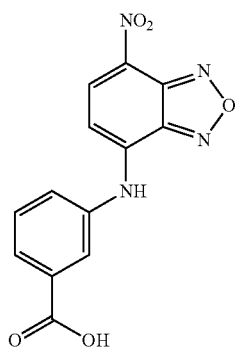
3m 3-((7-Nitrobenzo[c][1,2,5]oxadiazol-4-yl)amino)benzoic acid (3m): yield=145 mg, 48%; red solid; $^1$H NMR (400 MHz; DMSO-d$_6$) $\delta_H$ 13.2 (1H, s, CO$_2$H), 11.1 (1H, s, Ar—NH), 8.60 (1H, d, Ar—H, J=8.6 Hz), 8.06 (1H, s, Ar—H), 7.91 (1H, d, Ar—H, J=7.4 Hz), 7.78 (1H, d, Ar—H, J=7.4 Hz), 7.68 (1H, t, Ar—H, J=7.4 Hz), 6.81 (1H, d, Ar—H, J=8.6 Hz); $^{13}$C NMR (100 MHz; DMSO-d$_6$) $\delta_C$ 166.6, 145.1, 144.1, 142.1, 138.3, 137.6, 132.2, 130, 128, 126.9, 124.3, 123.6, 102.0; m/z (ESI) 323.0 (M+Na)$^+$.

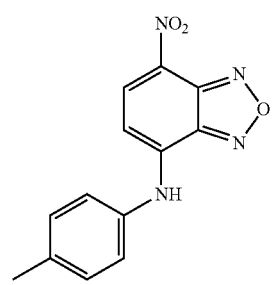
3o

7-Nitro-N-(p-tolyl)benzo[c][1,2,5]oxadiazol-4-amine (3o): yield=105 mg, 58%; violet crystals; $^1$H NMR (400 MHz; CDCl$_3$) 8.41 (1H, d, Ar—H, J=8.4 Hz), 7.75 (1H, s, Ar—NH), 7.28 (4H, m, Ar—H), 6.62 (1H, d, Ar—H, J=8.4 Hz), 2.40 (3H, s, CH$_3$); $^{13}$C NMR (100 MHz; CDCl$_3$) 144.6, 143.8, 141.4, 137.5, 136, 133.8, 130.7, 125.3, 123.7, 100.6, 29.6; m/z (ESI) 271.0 (M+H)$^+$.

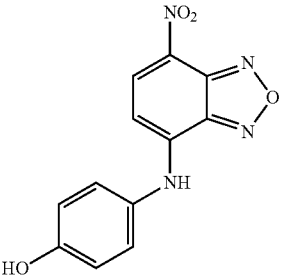
3p 4-((7-nitrobenzo[c][1,2,5]oxadiazol-4-yl)amino)phenol (3p): yield=272 mg, 62%; violet crystals; $^1$H NMR (400 MHz; DMSO-d$_6$) 10.9 (1H, s, Ar—OH), 9.79 (1H, s, Ar—NH), 8.50 (1H, d, Ar—H, J=8.8 Hz), 7.30 (2H, d, Ar—H, J=8.6 Hz), 6.92 (2H, d, Ar—H, J=8.6 Hz), 6.51 (1H, d, Ar—H, J=8.8 Hz); $^{13}$C NMR (100 MHz; DMSO-d$_6$) 157.2, 145.6, 145.2, 144.3, 138.7, 129.5, 126.9, 122.8, 117, 101.8 m/z found: 273.0 (M+H)$^+$.

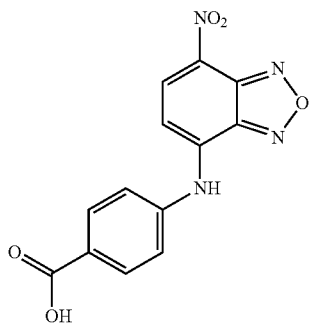
3q (JY-3-094)

4-((7-Nitrobenzo[c][1,2,5]oxadiazol-4-yl)amino)benzoic acid (3q, "JY-3-094"): yield=46 mg, 15%; red crystals; $^1$H NMR (400 MHz; DMSO-d$_6$) $\delta_H$ 12.94 (1H, s, CO$_2$H), 11.20

(1H, s, Ar—NH), 8.55 (1H, d, Ar—H, J=8.8 Hz), 8.06 (1H, d, Ar—H, J=8.4 Hz), 7.60 (1H, d, Ar—H, J=8.4 Hz), 6.94 (1H, d, Ar—H, J=8.8 Hz); $^{13}$C NMR (100 MHz; DMSO-d$_6$) δ$_C$ 167.6, 146.5, 145.2, 144, 142.4, 138, 131.8, 128.2, 124.5, 123.2, 104.4; m/z (ESI) 323.0 (M+Na)$^+$.

Compound 4 in Scheme 1

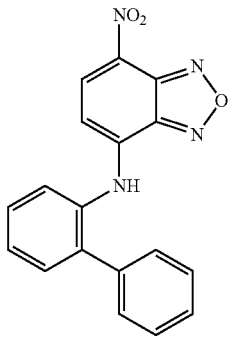

N-4-([1,1'-Biphenyl]-2-yl)benzo[c][1,2,5]oxadiazole-4,7-diamine (4): 10074-G5 (500 mg, 1.50 mmol) was dissolved in MeOH (15 mL). The flask was evacuated and purged with N$_2$ (×3). A suspension of 10% Pd/C (50 mg, 10 wt %) in THF (1 mL) was carefully added to the reaction mixture. H$_2$ was bubbled through the reaction mixture for 5 min, then the vessel was left under an atmosphere of H$_2$ (balloon) and stirred overnight at room temperature. The reaction mixture was filtered over a bed of Celite, washing with MeOH. Concentration of the MeOH in vacuo gave the title compound with no further purification necessary: yield: 344 mg, 76%; dark red solid; $^1$H NMR (400 MHz; DMSO-d$_6$) 6%$_1$ 7.47 (2H, d, Ar—H, J=7.6 Hz), 7.35 (2H, t, Ar—H, J=7.6 Hz), 7.26 (1H, d, Ar—H, J=7.2 Hz), 7.19 (2H, t, Ar—H, J=7.4H), 7.11 (1H, s, Ar—NH), 6.98 (1H, t, Ar—H, J=7.4 Hz), 6.90 (1H, d, Ar—H, J=8 Hz), 6.61 (1H, d, Ar—H, J=8 Hz), 6.15 (1H, d, Ar—H, J=7.6 Hz), 5.86 (2H, s, Ar—NH$_2$); $^{13}$C NMR (100 MHz; CDCl$_3$) δ$_C$ 146.5, 145.4, 139.1, 138.5, 132.3, 131, 129.07, 129, 128.5, 127.7, 122.8, 121.9, 118.5, 113.2, 108.9; m/z (ESI) 303.1 (M+H)$^+$.

General Procedure for Acylation of Compound 4 to Afford Compounds 5a-5e (Table 2)

Compound 4 (1 eq.) was dissolved in CH$_2$Cl$_2$ (0.1 M), then cooled to 0° C. Et$_3$N (2 eq.) was added, followed by the dropwise addition of the acylating agent (1.1 eq.). The reaction was allowed to react at room temperature overnight. The reaction mixture was diluted with further CH$_2$Cl$_2$, washed with 1 M HCl, dried (Na$_2$SO$_4$), filtered and concentrated. The crude residue was dry-loaded onto silica gel and purified by silica gel flash column chromatography, eluting with a gradient of EtOAc in Hexanes (5a-5c) or CH$_2$Cl$_2$/MeOH/AcOH, 92:7:1 (5d, 5e).

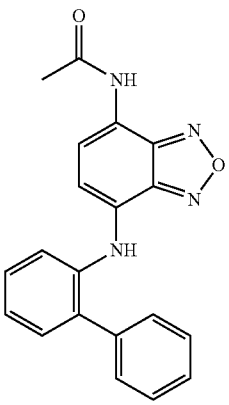

5a

N-(7-([1,1'-Biphenyl]-2-ylamino)benzo[c][1,2,5]oxadiazol-4-yl)acetamide (5a): yield=50 mg, 99%; red solid; $^1$H NMR (400 MHz; DMSO-d$_6$) δ$_H$ 10.0 (1H, s, Ar—NH), 8.93 (1H, s, Ar—NH), 7.47-7.17 (10H, m, Ar—H), 6.12 (1H, d, Ar—H, J=8 Hz), 2.03 (3H, s, CH$_3$); $^{13}$C NMR (100 MHz; DMSO-d$_6$) δ$_C$ 168.7, 146, 144.8, 139.2, 137.6, 136.5, 131, 130.1, 128.5, 128.3, 128.2, 127.1, 125.7, 125.4, 123.6, 115.3, 106.7; m/z (ESI) 367.1 (M+Na)$^+$.

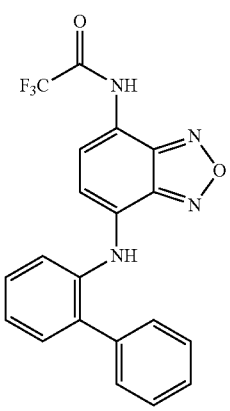

5b

N-(7-([1,1'-Biphenyl]-2-ylamino)benzo[c][1,2,5]oxadiazol-4-yl)-2,2,2-trifluoroacetamide (5b): yield=57 mg, 86%; orange solid; $^1$H NMR (400 MHz; DMSO-d$_6$) δ$_H$ 8.56 (1H, d, Ar—H, J=8.6 Hz), 8.07 (1H, d, Ar—H, J=7.7 Hz), 7.77 (1H, d, Ar—H, J=7.8 Hz), 7.71 (1H, t, Ar—H, J=7.7 Hz), 7.36 (1H, t, Ar—H, J=7.8 Hz), 6.95 (1H, d, Ar—H, J=8.6 Hz); $^{13}$C NMR (100 MHz; DMSO-d$_6$) δ$_C$ 168.7, 145.9, 144.3, 140.8, 139.4, 137.8, 134.4, 132.3, 125.8, 124.9, 123.2, 122.6, 103.7; m/z (ESI) 421.0 (M+Na)$^+$.

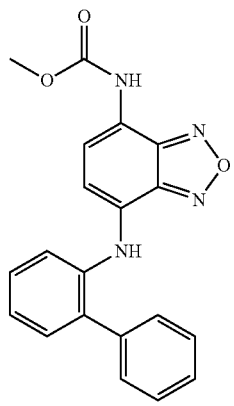

5c

Methyl (7-([1,1'-biphenyl]-2-ylamino)benzo[c][1,2,5]oxadiazol-4-yl)carbamate (5c): yield=19 mg, 38%; red solid; $^1$H NMR (400 MHz; DMSO-d$_6$) δ$_H$ 9.55 (1H, s, Ar—N$\underline{H}$) 8.54 (1H, s, Ar—N$\underline{H}$), 7.49-7.18 (10H, m, Ar—$\underline{H}$), 6.16 (1H, d, Ar—$\underline{H}$, J=7.6 Hz), 3.67 (3H, s, CO$_2$C$\underline{H}_3$; $^{13}$C NMR (100 MHz; DMSO-d$_6$); δ$_C$ 153.7, 145.4, 145.3, 138.1, 137.2, 134.1, 131.2, 128.98, 128.93, 128.3, 127.8, 123.7, 120.9, 118.2, 116.9, 107.5, 52.7; m/z (ESI) 383.0 (M+Na$^+$).

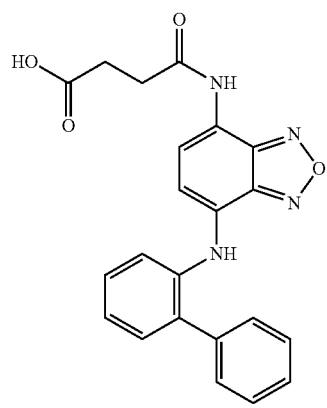 [SMILES: O=C(O)CCC(=O)Nc1ccc(Nc2ccccc2-c2ccccc2)c2nonc12]

5d 4-((7-([1,1'-Biphenyl]-2-ylamino)benzo[c][1,2,5]oxadiazol-4-yl)amino)-4-oxobutanoic acid (5d): yield: 72 mg, 95%; orange solid; $^1$H NMR (400 MHz; DMSO-d$_6$) δ$_H$ 10.3 (1H, s, CO$_2$$\underline{H}$), 8.45 (1H, s, Ar—N$\underline{H}$), 7.56-7.22 (10H, m, Ar—$\underline{H}$), 6.19 (1H, d, Ar—$\underline{H}$, J=8 Hz), 2.64 (2H, t, C$\underline{H}_2$, J=6.6 Hz), 2.50 (2H, t, C$\underline{H}_2$, J=6.6 Hz); $^{13}$C NMR (100 MHz; CDCl$_3$ & CD$_3$OD) δ$_C$ 171.1, 145.5, 145.4, 138.3, 137, 134.4, 131.2, 128.99, 128.96, 128.6, 128.4, 127.8, 124, 121.4, 121.2, 116.6, 107, 31.9, 29.7; m/z (ESI) 425.1 (M+Na$^+$).

5e 2-(2-((7-([1,1'-Biphenyl]-2-ylamino)benzo[c][1,2,5]oxadiazol-4-yl)amino)-2-oxoethoxy)acetic acid (5e): yield=30 mg, 95%; orange semi-solid; $^1$H NMR (400 MHz; DMSO-d$_6$) δ$_H$ 9.84 (1H, s, Ar—N$\underline{H}$), 8.56 (1H, s, Ar—N$\underline{H}$), 7.50-7.21 (10H, m, Ar—$\underline{H}$), 6.14 (1H, d, Ar—$\underline{H}$, J=7.6 Hz), 4.21 (4H, s, (C$\underline{H}_2$)$_2$); $^{13}$C NMR (100 MHz; CDCl$_3$) δ$_C$ 174, 167.7, 145.4, 145.2, 138.1, 136.8, 134.5, 131.2, 129.1, 128.97, 128.91, 128.3, 127.8, 124.1, 121.4, 115.6, 106.4, 71.3, 68.4; m/z (ESI) 441.0 (M+Na)$^+$.

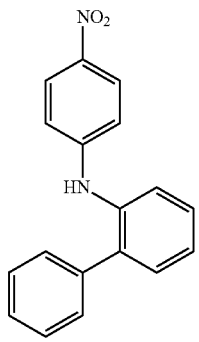

7

(Table 2)

N-(4-Nitrophenyl)-[1,1'-biphenyl]-2-amine (7): To a solution of 2-aminobiphenyl (6; x mg, x mmol, x eq.) in anhydrous DMF (x mL) was added potassium tert-butoxide (x mg, x mmol, 2.2 eq.) under an inert atmosphere at 0° C. After 30 min., 4-fluoronitrobenzene (x uL, x mmol, 1.1 eq.) was added. The reaction was allowed to stir at room temperature for 16 h. The reaction mixture was diluted with water, and the organics were extracted into EtOAc (×3). The combined organic extractions were washed with water (×5), brine, dried (Na$_2$SO$_4$), filtered and concentrated. The crude material was chromatographed over silica gel (eluent:Hex/EtOAc, 1:1) to deliver the title compound as an XXX: yield=x mg, x %; δ$_H$ (400 MHz; CDCl$_3$) 8.10 (d, J=8.4, 2 H, Ar), 7.51-7.32 (m, 8H, Ar), 7.26 (t, J=6.4, 1 H, Ar), 6.88 (d, J=8.4, 2 H, Ar), 6.02 (s, 1H, NH); δ$_C$ (100 MHz; CDCl$_3$) 150.5, 138.2, 136.5, 135.4, 131.3, 129.1, 128.9, 128.5, 127.9, 126.2, 125.1, 122.7, 113.7; m/z (ESI) 291.3 (M+H)$^+$.

General Procedure for Ester Prodrugs of JY-3-094

To aryl acid (40 mg, 0.13 mmol) and K$_2$CO$_3$ (74 mg, 0.53 mmol) in DMF (2 mL) was added the corresponding alkyl halide (2 eq.) at room temperature. The reaction mixture was stirred for 6 h and partitioned between EtOAc/sat. NH₄Cl. The organic layer was washed with H₂O (×3), sat. NaCl, dried over NaSO₄ and reduced in vacuo. The crude residue was purified by column chromatography (SiO₂, Hexane/EtOAc) to provide the title compounds.

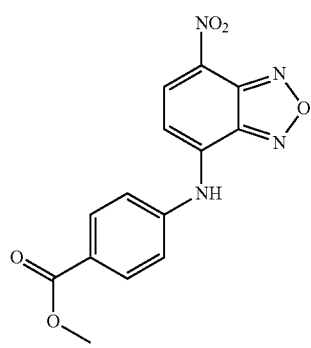

3jc91-1

Methyl 4-((7-nitrobenzo[c][1,2,5]oxadiazol-4-yl)amino)benzoate (3JC-91-1). Following general procedure 1 with methyl iodide gave the title compound as a red solid (28 mg, 68%). $\delta_H$ (DMSO-d₆, 400 MHz) 11.14 (br s, 1H, NH), 8.76 (d, J=8.8, 1H, Ar), 8.04 (d, J=7.6, 1H, Ar), 7.62 (d, J=7.6, 1H, Ar), 7.01 (d, J=8.8, 1H, Ar), 3.86 (s, 3H, CH₃); $\delta_C$ (DMSO-d₆, 100 MHz) 166.0, 145.8, 144.5, 143.1, 141.0, 137.6, 131.1, 126.5, 125.1, 122.8, 104.1, 52.6; m/z (APCI+ve) 315 [M+H]⁺.

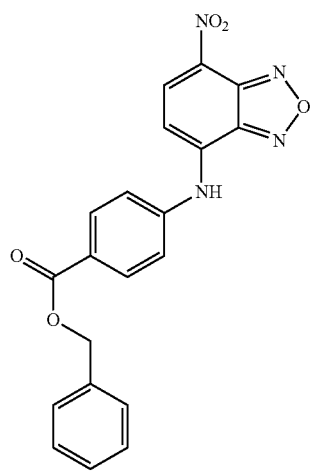

3jc91-2

Benzyl 4-((7-nitrobenzo[c][1,2,5]oxadiazol-4-yl)amino)benzoate (3JC-91-2). Following general procedure 1 with benzyl bromide gave the title compound as a red solid (41 mg, 82%). $\delta_H$ (DMSO-d₆, 400 MHz) 8.49 (d, J=8.8, 1H, Ar), 8.21 (d, J=8.8, 2H, Ar), 7.95 (br s, 1H, NH), 7.51-7.29 (m, 7H, Ar), 6.94 (d, J=8.8, 1H, Ar), 5.40 (s, 2H, CH₂); $\delta_C$ (DMSO-d₆, 100 MHz) 165.3, 145.0, 141.2, 139.3, 135.7, 135.4, 131.8, 128.7, 128.4, 128.3, 127.9, 121.7, 102.3, 67.0; m/z (APCI+ve) 391 [M+H]⁺.

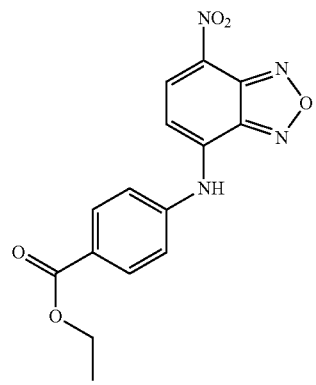

3jc91-3

Ethyl 4-((7-nitrobenzo[c][1,2,5]oxadiazol-4-yl)amino)benzoate (3JC-91-3). Following general procedure 1 with ethyl bromide gave the title compound as a red solid (35 mg, 81%). $\delta_H$ (DMSO-d₆, 400 MHz) 11.16 (br s, 1H, NH), 8.57 (d, J=8.8, 1 H, Ar), 8.05 (d, J=7.6, 2 H, Ar), 7.63 (d, J=7.6, 2 H, Ar), 7.01 (d, J=8.8, 1H, Ar), 4.33 (q, J=7.2, 2 H, CH₂), 1.33 (t, J=7.2, 3 H, CH₃); $\delta_C$ (DMSO-d₆, 100 MHz) 165.1, 154.4, 144.2, 142.7, 140.8, 137.2, 130.7, 126.4, 124.6, 122.4, 103.7, 60.8, 14.2; m/z (APCI+ve) 329 [M+H]⁺.

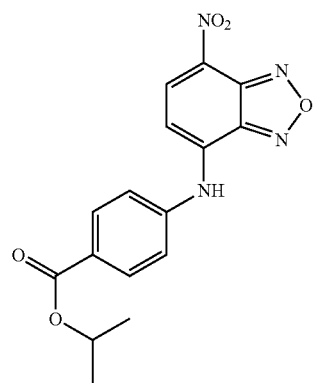

3jc91-4

Following general procedure 1 with isopropyl iodide gave the title compound as a red solid (18 mg, 40%). $\delta_H$ (DMSO-d₆, 400 MHz) 11.15 (br s, 1H, NH), 8.56 (d, J=8.4, 1H, Ar), 8.04 (d, J=8.0, 2 H, Ar), 7.61 (d, J=8.0, 2 H, Ar), 6.78 (d, J=8.4, 1H, Ar), 4.33 (hept, J=6.4, 1H, CH), 1.34 (d, J=6.4, 6 H, 2×CH₃); $\delta_C$ (DMSO-d₆, 100 MHz) 164.6, 145.4, 144.2, 142.7, 140.9, 137.2, 130.6, 126.8, 124.5, 122.4, 103.6, 68.1, 21.7; m/z (APCI+ve) 343 [M+H]⁺.

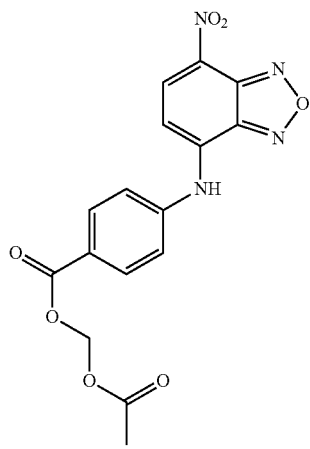

Acetoxymethyl 4-((7-nitrobenzo[c][1,2,5]oxadiazol-4-yl)amino)benzoate (3JC-91-5). Following general procedure 1 with bromomethyl acetate gave the title compound as a red solid (31 mg, 64%). $\delta_H$ (DMSO-$d_6$, 400 MHz) 11.17 (br s, 1H, NH), 8.58 (d, J=8.8, 1H, Ar), 8.06 (d, J=8.0, 2H, Ar), 7.65 (d, J=8.0, 2H, Ar), 7.06 (d, J=8.8, 1H, Ar), 5.94 (s, 2H, $CH_2$), 2.12 (s, 3H, $CH_3$); $\delta_C$ (DMSO-$d_6$, 100 MHz) 169.9, 164.3, 145.9, 144.5, 143.9, 140.8, 137.6, 131.6, 125.4, 125.2, 122.7, 104.5, 80.1, 21.0; m/z (APCI+ve) 373 [M+H]$^+$.

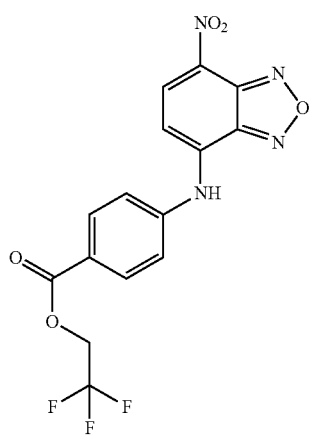

Trifluoroethyl 4-((7-nitrobenzo[c][1,2,5]oxadiazol-4-yl)amino)benzoate (3JC-91-7). Following general procedure 1 with 2-bromo-1,1,1-trifluoroethane gave the title compound as a red solid (38 mg, 76%). $\delta_H$ (CDCl$_3$, 400 MHz) 8.48 (d, J=8.8, 1H, Ar), 8.18 (d, J=8.4, 2H, Ar), 7.50 (d, J=8.4, 2H, Ar), 6.97 (d, J=8.4, 1H, Ar), 4.71 (q, J=7.6, 1H, Ar); $\delta_C$ (CDCl$_3$, 100 MHz) 163.8, 145.1, 143.7, 142.1, 138.8, 135.2, 132.2, 125.9, 121.6, 102.6, 61.4, 60.8; m/z (APCI+ve) 383 [M+H]$_+$.

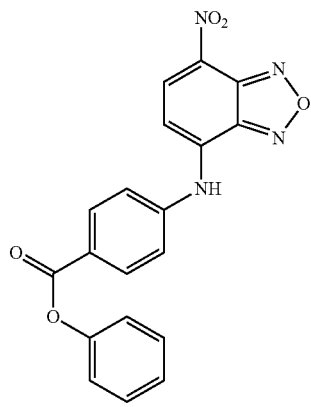

Phenyl 4-((7-nitrobenzo[c][1,2,5]oxadiazol-4-yl)amino)benzoate (SF-4-017). To aryl acid (50 mg, 0.17 mmol) and HBTU (74 mg, mmol) in DMF (2 mL) was added DIPEA (58 uL, 0.33 mmol) at room temperature. After 1 h, phenol (24 mg, 0.25 mmol) was added and the reaction mixture was stirred for 20 h before being partitioned between EtOAc/sat. NH$_4$Cl. The organic layer was washed with H$_2$O (×3), sat. NaCl, dried over NaSO$_4$ and reduced in vacuo. The crude residue was purified by column chromatography (SiO$_2$, Hexane/EtOAc) to provide the title compound (28 mg, 68%). $\delta_H$ (DMSO-$d_6$, 400 MHz) 11.21 (br s, 1H, NH), 8.60 (d, J=8.8, 1H, Ar), 8.22 (d, J=8.4, 2H, Ar), 7.71 (d, J=8.4, 2H, Ar), 7.49 (t, J=8.0, 2H, Ar), 7.35-7.28 (m, 3H, Ar), 7.08 (d, J=8.8, 1H, Ar); $\delta_C$ (DMSO-$d_6$, 100 MHz) 164.3, 151.1, 145.9, 144.6, 143.9, 140.9, 137.6, 131.9, 130.0, 126.5, 125.4, 122.7, 122.4, 104.5; m/z (APCI+ve) 377 [M+H]$^+$.

General Procedure for $S_NAr$ and Deprotection to Prepare 2-Aminobiphenyls and 3-Aminobiphenyls

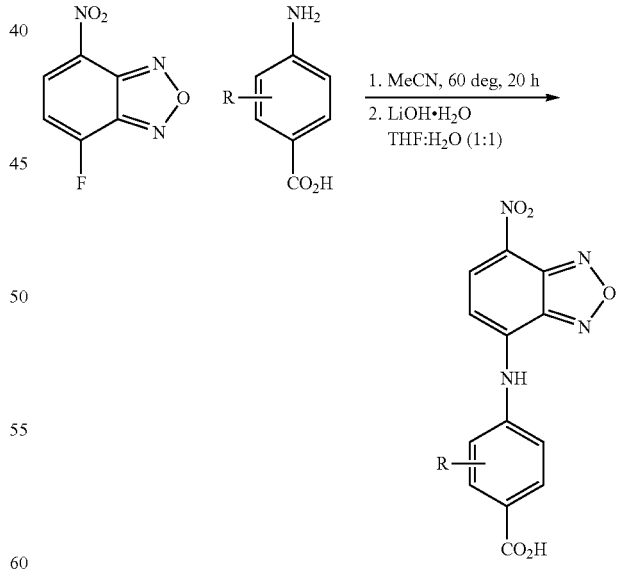

NDB-F (30 mg, 0.16 mmol) and aniline (1.1 eq) were dissolved in MeCN. The reaction mixture was heated to 60° C. for 20 hours. The reaction mixture was cooled, reduced in vacuo and partitioned between EtOAC/H$_2$O. The organic layer was washed with H$_2$O (×2), sat. NaCl, dried over NaSO$_4$ and reduced in vacuo. The crude mixture was purified by column chromatography (SiO$_2$, hexane/EtOAc) to afford the corresponding methyl ester. The ester was dissolved in 1:1 THF/H$_2$O (2 mL) and treated with 2 M LiOH.H$_2$O (3 eq.) at room temperature for 20 h. The reaction mixture was diluted with H$_2$O and washed with EtOAc (×2). The aqueous phase was neutralized with 1 M HCl and extracted with EtOAc (×2). The organic layer was washed with sat. NaCl, dried over NaSO$_4$, reduced in vacuo and lyophilized to give the title compound as a red solid.

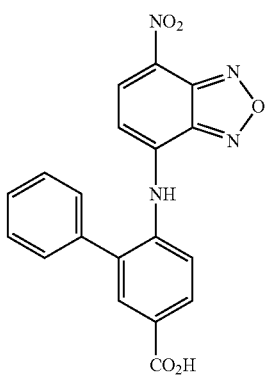

3jc42

General procedure gave the title compound as a red solid 47 mg, 77%.

$\delta_H$ (DMSO-d$_6$, 400 MHz) 13.20 (br s, 1H, CO$_2$H), 11.04 (br s, 1H, NH), 8.39 (d, J=8.8, 1H, Ar), 8.07 (d, J=8.0, 1H, Ar), 8.03 (s, 1H, Ar), 7.66 (d, J=8.0, 1H, Ar), 7.46-7.23 (m, 5H, Ar), 6.23 (d, J=8.8, 1H, Ar); $\delta_C$ (DMSO-d$_6$, 100 MHz) 171.7, 149.5, 149.2, 148.2, 144.0, 143.6, 142.7, 137.3, 135.6, 134.9, 133.8, 133.6, 133.2, 133.1, 128.1, 108.3.

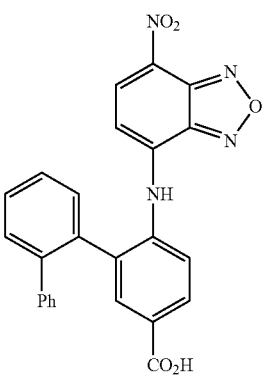

3jc53-1

General procedure gave the title compound as a red solid 20 mg, 28%.

$\delta_H$ (DMSO-d$_6$, 400 MHz) 13.14 (br s, 1H, CO$_2$H), 10.41 (br s, 1H, NH), 8.28 (d, J=8.4, 1H, Ar), 7.99-7.93 (m, 2H, Ar), 7.50 (d, J=8.4, 1H, Ar), 7.48-7.38 (m, 3H, Ar), 7.31-7.28 (m, 1H, Ar), 6.97-6.90 (m, 3H, Ar), 6.84 (dd, J=7.6, 1.2, 1H, Ar), 5.99 (d, J=8.4, 1H, Ar); $\delta_C$ (DMSO-d$_6$, 100 MHz) 171.7, 149.4, 149.1, 147.4, 145.7, 145.6, 144.3, 142.5, 142.3, 140.8, 138.8, 136.9, 135.4, 134.5, 134.3, 133.8, 133.0, 132.9, 131.9, 131.5, 127.9, 107.3.

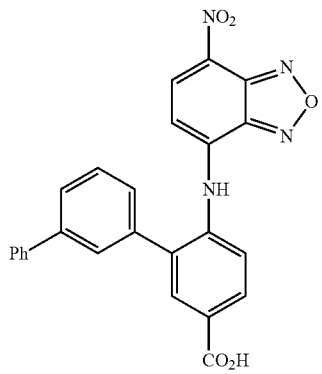

3jc53-2

General procedure gave the title compound as a red solid 36 mg, 49%. $\delta_H$ (DMSO-d$_6$, 400 MHz) 13.27 (br s, 1H, CO$_2$H), 11.15 (br s, 1H, NH), 8.38 (d, J=8.8, 1H, Ar), 8.14-8.08 (m, 2H, Ar), 7.71-7.66 (m, 2H, Ar), 7.55-7.47 (m, 3H, Ar), 7.42-7.30 (m, 5H, Ar), 6.24 (d, J=8.8, 1H, Ar); $\delta_C$ (DMSO-d$_6$, 100 MHz) 171.3, 149.5, 149.1, 148.2, 145.6, 144.8, 144.1, 143.5, 143.3, 142.3, 137.3, 135.7, 135.1, 134.4, 134.0, 133.4, 132.8, 132.6, 132.0, 131.8, 131.4, 128.1, 108.2.

3jc53-3

Ph

General procedure gave the title compound as a red solid 46 mg, 63%. $\delta_H$ (DMSO-d$_6$, 400 MHz) 13.24 (br s, 1H, CO$_2$H), 11.07 (br s, 1H, NH), 8.44 (d, J=8.8, 1H, Ar), 8.10-8.06 (m, 2H, Ar), 7.72-7.59 (m, 5H, Ar), 7.54 (d, J=8.0, 2 H, Ar), 7.43 (t, J=7.2, 2 H, Ar), 7.34 (t, J=7.2, 1H, Ar), 6.32 (d, J=8.8, 1H, Ar); $\delta_C$ (DMSO-d$_6$, 100 MHz) 171.7, 149.6, 149.3, 148.4, 144.7, 144.4, 144.1, 143.1, 141.8, 137.3, 135.6, 134.9, 134.3, 134.1, 133.3, 132.8, 132.0, 131.7, 128.3, 108.0.

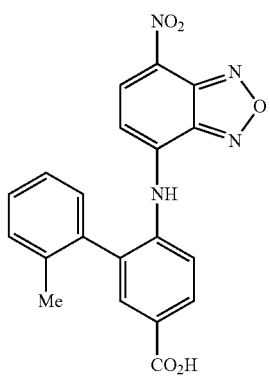

3jc53-4

General procedure gave the title compound as a red solid 30 mg, 48%. $\delta_H$ (DMSO-d$_6$, 400 MHz) 13.10 (br s, 1H, CO₂H), 10.83 (br s, 1H, NH), 8.41 (d, J=8.8, 1H, Ar), 8.07 (d, J=7.8, 1H, Ar), 7.87 (s, 1H, Ar), 7.65 (d, J=7.8, 1H, Ar), 7.20-7.18 (m, 4H, Ar), 6.32 (d, J=8.8, 1H, Ar), 2.10 (s, 3H, Me); $\delta_C$ (DMSO-d₆, 100 MHz) 171.8, 149.5, 149.1, 147.7, 143.1, 142.2, 140.5, 137.8, 135.3, 134.9, 134.8, 133.2, 132.4, 130.9, 128.2, 108.7, 24.8.

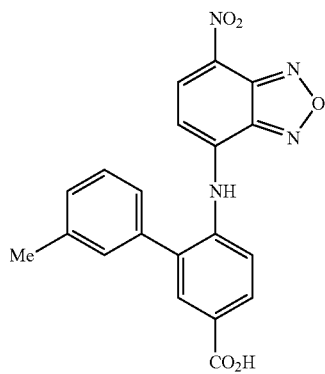

3jc53-5

General procedure gave the title compound as a red solid 28 mg, 45%. $\delta_H$ (DMSO-d₆, 400 MHz) 13.24 (br s, 1H, CO₂H), 11.01 (br s, 1H, NH), 8.39 (d, J=8.4, 1H, Ar), 8.07-8.05 (m, 2H, Ar), 7.64 (d, J=7.6, 1H, Ar), 7.26 (s, 1H, Ar), 7.23-7.15 (m, 2H, Ar), 7.08 (s, 1H, Ar), 6.22 (d, J=8.4, 1H, Ar), 2.21 (s, 3H, Me); $\delta_C$ (DMSO-d₆, 100 MHz) 171.7, 149.5, 149.2, 148.2, 144.1, 143.6, 143.0, 142.7, 142.3, 137.3, 135.5, 134.8, 134.3, 133.6, 133.5, 133.2, 130.6, 128.1, 108.1.

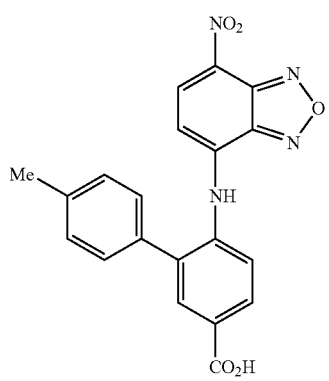

3jc53-6

General procedure gave the title compound as a red solid 56 mg, 88%. $\delta_H$ (DMSO-d₆, 400 MHz) 13.20 (br s, 1H, CO₂H), 11.01 (br s, 1H, NH), 8.40 (d, J=8.4, 1H, Ar), 8.05-8.00 (m, 2H, Ar), 7.64 (d, J=8.4, 1H, Ar), 7.33 (d, J=7.6, 2 H, Ar), 7.14 (d, J=7.6, 2 H, Ar), 6.22 (d, J=8.4, 1H, Ar), 2.23 (s, 3H, Me); $\delta_C$ (DMSO-d₆, 100 MHz) 171.7, 149.5, 149.2, 148.3, 143.9, 143.6, 142.5, 139.8, 137.3, 135.6, 134.6, 134.4, 133.5, 133.3, 128.1, 107.8.

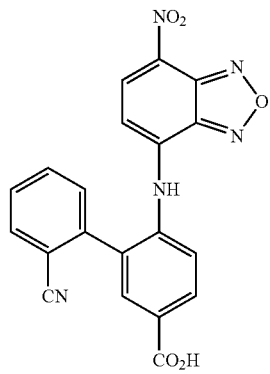

3jc53-7

General procedure gave the title compound as a red solid 37 mg, 57%. $\delta_H$ (DMSO-d₆, 400 MHz) 12.81 (br s, 1H, CO₂H), 11.13 (br s, 1H, NH), 8.48 (d, J=8.8, 1H, Ar), 8.07 (d, J=8.0, 1H, Ar), 7.83 (d, J=8.0, 1H, Ar), 7.69 (t, J=8.0, 1H, Ar), 7.63 (d, J=8.0, 1H, Ar), 7.51 (t, J=8.0, 1H, Ar), 7.48 (d, J=8.0, 1H, Ar), 7.40 (s, 1H, Ar), 7.04 (d, J=8.8, 1H, Ar); $\delta_C$ (DMSO-d₆, 100 MHz) 167.1, 145.9, 145.3, 144.5, 141.9, 141.1, 137.5, 133.3, 132.7, 130.0, 128.5, 127.4, 125.1, 125.0, 122.5, 118.6, 111.8, 104.4.

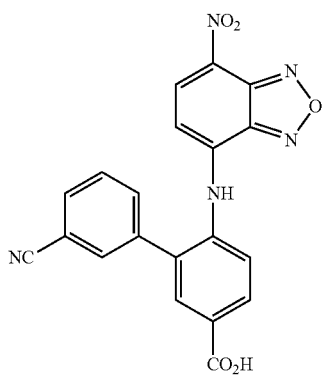

3jc53-8

General procedure gave the title compound as a red solid 24 mg, 38%. $\delta_H$ (DMSO-d₆, 400 MHz) 13.26 (br s, 1H, CO₂H), 10.99 (br s, 1H, NH), 8.40 (d, J=8.4, 1H, Ar), 8.11 (d, J=8.0, 1H, Ar), 8.08 (s, 1H, Ar), 7.95 (s, 1H, Ar), 7.77-7.67 (m, 3H, Ar), 7.51 (t, J=7.6, 1H, Ar), 6.27 (d, J=8.4, 1H, Ar); $\delta_C$ (DMSO-d₆, 100 MHz) 171.6, 149.6, 149.2, 147.9, 144.2, 143.9, 142.2, 141.5, 138.6, 137.4, 136.8, 135.7, 135.6, 134.9, 133.2, 128.6, 123.6, 116.9, 108.3.

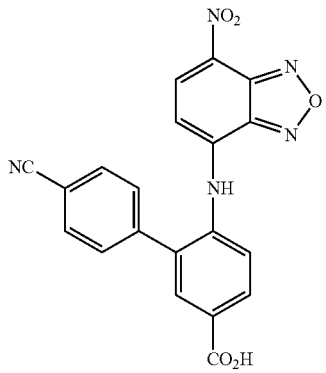

3jc53-9

General procedure gave the title compound as a red solid 40 mg, 62%. $\delta_H$ (DMSO-d₆, 400 MHz) 13.29 (br s, 1H, CO₂H), 11.01 (br s, 1H, NH), 8.42 (d, J=8.8, 1H, Ar), 8.12 (dd, J=8.4, 2.0, 1H, Ar), 8.05 (d, J=2.0, 1H, Ar), 7.82 (dd, J=6.4, 1.6 2H, Ar), 7.70 (d, J=8.4, 1H, Ar), 7.64 (dd, J=6.4, 1.6, 2 H, Ar), 6.30 (d, J=8.8, 1H, Ar); δ_C (DMSO-d₆, 100 MHz) 166.8, 144.9, 144.5, 1443.3, 142.8, 139.5, 137.5, 137.0, 132.9, 132.5, 131.1, 130.8, 130.0, 128.5, 123.8, 119.0, 111.0, 103.4.

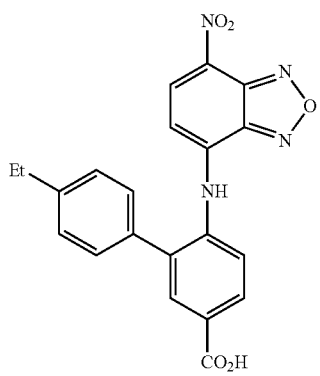

3jc53-10

General procedure gave the title compound as a red solid 42 mg, 64%. δ_H (DMSO-d₆, 400 MHz) 13.17 (br s, 1H, CO₂H), 10.98 (br s, 1H, NH), 8.37 (d, J=8.8, 1H, Ar), 8.03-7.88 (m, 2H, Ar), 7.61 (d, J=7.6, 1H, Ar), 7.30 (d, J=8.0, 2 H, Ar), 7.12 (d, J=8.0, 2H, Ar), 6.20 (d, J=8.8, 1H, Ar), 2.54-2.44 (m, 2H, CH₂), 1.04 (t, 3H, CH₃); δ_C (DMSO-d₆, 100 MHz) 171.7, 149.5, 149.2, 148.7, 148.3, 144.1, 143.4, 140.1, 137.3, 135.5, 134.6, 133.6, 133.2, 128.1, 108.1, 32.9, 20.6.

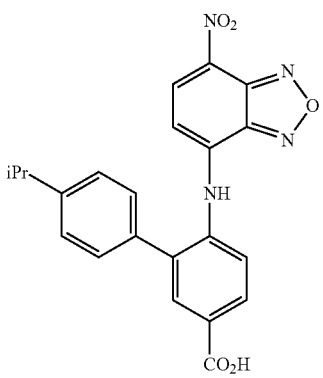

3jc53-11

General procedure gave the title compound as a red solid 48 mg, 71%. δ_H (DMSO-d₆, 400 MHz) 13.20 (br s, 1H, CO₂H), 11.01 (br s, 1H, NH), 8.40 (d, J=8.8, 1H, Ar), 8.06-8.00 (m, 2H, Ar), 7.64 (d, J=8.8, 1H, Ar), 7.32 (d, J=8.0, 2H, Ar), 7.18 (d, J=8.0, 2H, Ar), 6.26 (d, J=8.8, 1H, Ar), 2.81 (hept, 1H, CH), 1.10 (d, 6H, 2×CH₃); δ_C (DMSO-d₆, 100 MHz) 171.7, 153.3, 149.6, 149.2, 148.3, 144.2, 143.2, 142.3, 140.3, 137.2, 135.4, 134.6, 133.6, 133.1, 131.7, 128.1, 108.4, 38.2, 28.8.

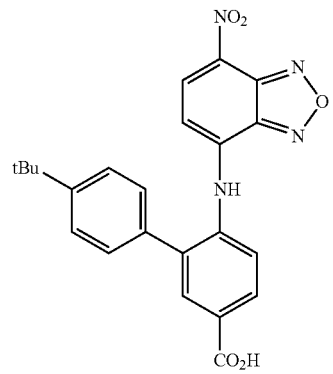

3jc53-12

General procedure gave the title compound as a red solid 41 mg, 59%. δ_H (DMSO-d₆, 400 MHz) 13.19 (br s, 1H, CO₂H), 11.01 (br s, 1H, NH), 8.40 (d, J=8.4, 1H, Ar), 8.06-8.00 (m, 2H, Ar), 7.65 (d, J=8.8, 1H, Ar), 7.35-7.30 (m, 4H, Ar), 6.27 (d, J=8.4, 1H, Ar), 1.19 (d, 9H, 3×CH₃); δ_C (DMSO-d₆, 100 MHz) 171.7, 155.5, 149.6, 149.2, 148.4, 144.2, 143.1, 139.9, 137.2, 135.4, 134.6, 133.4, 133.1, 130.5, 128.2, 108.5, 39.4, 36.1.

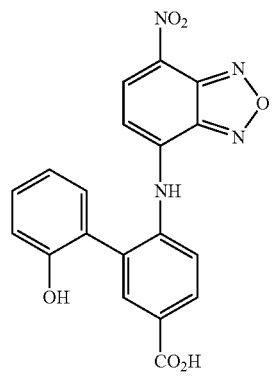

3jc53-13

General procedure gave the title compound as a red solid 22 mg, 35%. δ_H (DMSO-d₆, 400 MHz) 12.98 (br s, 1H, CO₂H), 10.57 (br s, 1H, NH), 10.15 (br s, 1H, OH), 8.43 (d, J=8.4, 1H, Ar), 8.05 (d, J=7.6, 1H, Ar), 7.99 (s, 1H, Ar), 7.71 (d, J=8.0, 1H, Ar), 7.22-7.10 (m, 2H, Ar), 6.89 (d, J=7.6, 1H, Ar), 6.82 (d, J=7.6, 1H, Ar), 6.49 (d, J=8.4, 1H, Ar); δ_C (DMSO-d₆, 100 MHz) 171.8, 159.0, 149.8, 149.2, 147.3, 144.8, 140.3, 138.4, 136.3, 134.8, 134.4, 131.0, 129.6, 128.3, 124.8, 124.7, 120.9, 107.9.

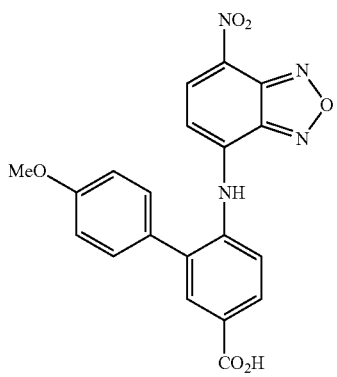

3jc53-14

General procedure gave the title compound as a red solid 26 mg, 40%. δ_H (DMSO-d₆, 400 MHz) 13.20 (br s, 1H, CO$_2$H), 11.02 (br s, 1H, NH), 8.40 (d, J=8.8, 1H, Ar), 8.05-7.98 (m, 2H, Ar), 7.62 (d, J=8.0, 1H, Ar), 7.37 (d, J=8.0, 2 H, Ar), 6.89 (d, J=8.0, 2 H, Ar), 6.20 (d, J=8.8, 1H, Ar), 3.69 (s, 3H, OCH$_3$); δ$_C$ (DMSO-d$_6$, 100 MHz) 167.0, 159.4, 144.8, 144.5, 143.6, 138.6, 137.6, 132.4, 130.8, 130.2, 130.1, 129.6, 128.5, 114.5, 103.1, 55.5.

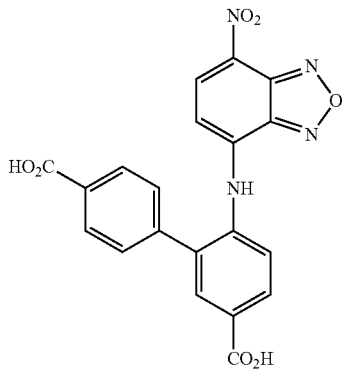

3jc53-15

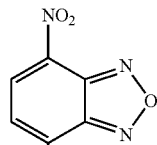

3jc62-1

General procedure gave the title compound as a red solid 46 mg, 72%. δ$_H$ (DMSO-d$_6$, 400 MHz) 12.58 (br s, 1H, CO$_2$H), 11.12 (br s, 1H, NH), 8.58 (d, J=8.8, 1H, Ar), 7.99 (d, J=8.4, 1H, Ar), 7.59 (dd, J=8.4, 2.4, 1H, Ar), 7.27 (d, J=2.4, 1H, Ar), 7.26-7.15 (m, 3H, Ar), 7.10 (d, J=7.2, 1H, Ar), 6.98 (d, J=8.8, 1H, Ar), 2.09 (s, 3H, CH$_3$); δ$_C$ (DMSO-d$_6$, 100 MHz) 167.6, 145.4, 144.2, 143.4, 141.1, 140.9, 140.8, 137.4, 134.8, 131.4, 129.4, 128.4, 128.2, 127.2, 125.3, 124.6, 124.3, 121.0, 103.6, 19.8.

General procedure gave the title compound as a red solid 28 mg, 41%. δ$_H$ (DMSO-d$_6$, 400 MHz) 13.12 (br s, 2H, 2×CO$_2$H), 11.02 (br s, 1H, NH), 8.42 (d, J=8.4, 1H, Ar), 8.12-8.04 (m, 2H, Ar), 7.89 (d, J=8.0, 1H, Ar), 7.75-7.66 (m, 1H, Ar), 7.56 (d, J=8.0, 2 H, Ar), 6.29 (d, J=8.4, 1 H, Ar); δ$_C$ (DMSO-d$_6$, 100 MHz) 167.4, 166.9, 144.8, 144.5, 143.4, 142.4, 139.4, 137.8, 137.6, 132.5, 130.9, 130.7, 130.4, 130.0, 129.8, 129.3, 129.2, 128.6, 123.7, 103.3.

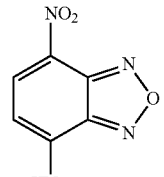

3jc62-2

General procedure gave the title compound as a red solid 41 mg, 65%. δ$_H$ (DMSO-d$_6$, 400 MHz) 12.79 (br s, 1H, CO$_2$H), 11.16 (br s, 1H, NH), 8.56 (d, J=8.4, 1H, Ar), 7.85 (d, J=8.4, 1H, Ar), 7.54 (d, J=8.0, 1H, Ar), 7.45 (s, 1H, Ar), 7.30 (t, J=8.0, 1H, Ar), 7.22-7.14 (m, 3H, Ar), 6.97 (d, J=8.4 1H, Ar), 2.35 (s, 3H, CH$_3$); δ$_C$ (DMSO-d$_6$, 100 MHz) 168.9, 145.4, 144.2, 142.8, 141.4, 140.5, 140.2, 137.4, 137.2, 130.9, 129.0, 128.9, 128.1, 128.0, 125.5, 124.5, 123.9, 121.2, 103.2.

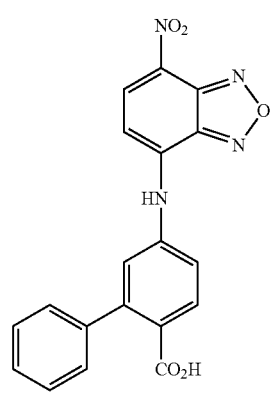

3jc62-7

General procedure gave the title compound as a red solid 34 mg, 56% δ$_H$ (DMSO-d$_6$, 400 MHz) 13.23 (br s, 1H, CO$_2$H), 11.05 (br s, 1H, NH), 8.39 (d, J=8.4, 1H, Ar), 8.07 (d, J=8.0, 1H, Ar), 8.03 (s, 1H, Ar), 7.65 (d, J=8.0, 1H, Ar), 7.46-7.22 (m, 5H, Ar), 6.22 (d, J=8.4, 1H, Ar); δ$_C$ (DMSO-d$_6$, 100 MHz) 167.0, 144.8, 144.5, 1443.5, 139.4, 138.7, 138.0, 137.5, 132.6, 130.8, 130.1, 129.0, 128.8, 128.4, 128.3, 123.3, 103.3.

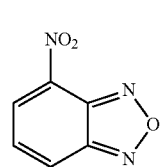

3jc62-3

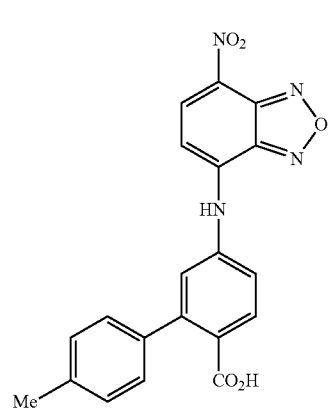

General procedure gave the title compound as a red solid 52 mg, 81%. δ$_H$ (DMSO-d$_6$, 400 MHz) 12.76 (br s, 1H, CO₂H), 11.15 (br s, 1H, NH), 8.55 (d, J=8.8, 1H, Ar), 7.84 (d, J=8.8, 1H, Ar), 7.51 (d, J=8.0, 1H, Ar), 7.43 (s, 1H, Ar), 7.28 (d, J=8.0, 2 H, Ar), 7.23 (d, J=8.0, 2 H, Ar), 6.95 (d, J=8.8, 1H, Ar), 2.35 (s, 3H, CH₃); $\delta_C$ (DMSO-d₆, 100 MHz) 169.4, 145.8, 144.7, 143.1, 137.8, 137.2, 131.4, 129.3, 129.2, 128.6, 124.9, 121.5, 103.7, 21.2.

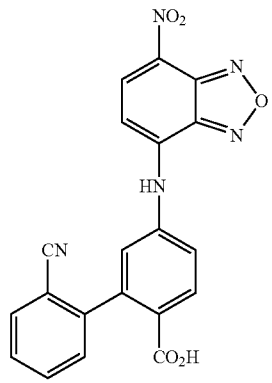

3jc62-4

General procedure gave the title compound as a red solid 51 mg, 78%. $\delta_H$ (DMSO-d₆, 400 MHz) 12.87 (br s, 1H, CO₂H), 11.20 (br s, 1H, NH), 8.54 (d, J=8.8, 1H, Ar), 8.13 (d, J=8.0, 1H, Ar), 7.89 (d, J=8.0, 1H, Ar), 7.75 (t, J=8.0, 1H, Ar), 7.70 (d, J=8.0, 1H, Ar), 7.57 (t, J=8.0, 1H, Ar), 7.52 (d, J=8.0, 1H, Ar), 7.46 (s, 1H, Ar), 7.10 (d, J=8.8, 1H, Ar); $\delta_C$ (DMSO-d₆, 100 MHz) 167.1, 145.9, 145.3, 144.5, 141.9, 141.1, 137.5, 133.3, 132.7, 130.0, 128.5, 127.4, 125.1, 125.0, 122.5, 118.6, 111.8, 104.4.

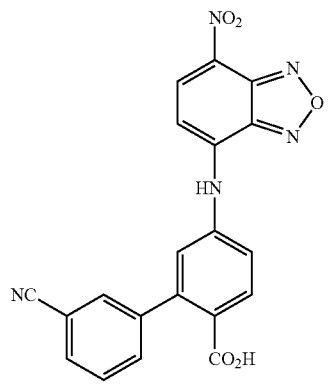

3jc62-5

General procedure gave the title compound as a red solid 43 mg, 66%. $\delta_H$ (DMSO-d₆, 400 MHz) 12.92 (br s, 1H, CO₂H), 11.14 (br s, 1H, NH), 8.56 (d, J=8.4, 1H, Ar), 7.99 (d, J=8.8, 1H, Ar), 7.88-7.82 (m, 2H, Ar), 7.71 (d, J=8.0, 1H, Ar), 7.63 (t, J=8.0, 2 H, Ar), 7.51 (s, 1H, Ar), 7.08 (d, J=8.4, 1H, Ar); $\delta_C$ (DMSO-d₆, 100 MHz) 168.3, 145.7, 144.5, 142.2, 141.8, 141.4, 141.2, 137.8, 133.9, 132.3, 132.2, 131.6, 129.7, 128.2, 125.0, 124.9, 122.2, 119.2, 111.5, 104.2.

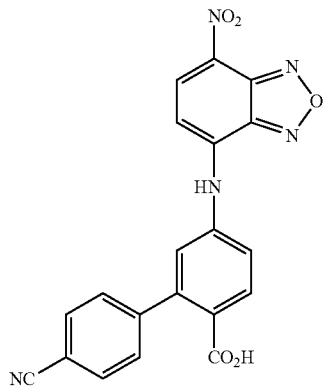

3jc62-6

General procedure gave the title compound as a red solid 33 mg, 51%. $\delta_H$ (DMSO-d₆, 400 MHz) 12.91 (br s, 1H, CO₂H), 11.22 (br s, 1H, NH), 8.54 (d, J=8.8, 1H, Ar), 7.95 (d, J=8.4, 1H, Ar), 7.86 (d, J=8.8, 2 H, Ar), 7.60 (d, J=8.4, 1H, Ar), 7.54 (d, J=8.8, 2 H, Ar), 7.45 (s, 1H, Ar), 7.04 (d, J=8.8, 1H, Ar); $\delta_C$ (DMSO-d₆, 100 MHz) 168.2, 146.0, 144.7, 142.2, 137.6, 132.4, 132.1, 129.9, 124.7, 122.3, 119.3, 110.6, 104.4.

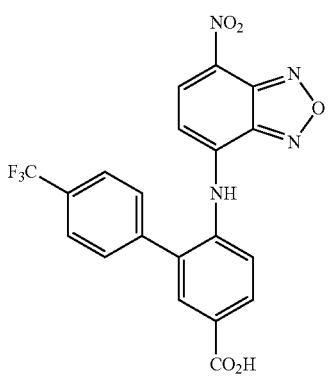

4jc23-6

Methyl ester 4jc23-4 (20 mg, 0.043 mmol) 1:1 THF/H₂O (2 mL) was treated with 2 M LiOH.H₂O (32 uL, 0.065 mmol) at room temperature for 20 h. The reaction mixture was neutralized with 1 M HCl and extracted with EtOAc (×2). The organic layer was washed with sat. NaCl, dried over NaSO₄, reduced in vacuo and lyophilized to give the title compound as a red solid (18 mg, 98%). $\delta_H$ (DMSO-d₆, 400 MHz) 13.20 (br s, 1H, COOH), 11.04 (br s, 1H, NH), 8.43 (d, J=8.8, 1H, Ar), 8.11 (d, J=8.0, 1H, Ar), 8.07 (s, 1H, Ar), 7.75-7.61 (m, 5H, Ar), 6.35 (d, J=8.8, 1H, Ar); $\delta_C$ (DMSO-d₆, 100 MHz) 166.4, 144.5, 144.1, 143.2, 141.8, 137.1, 136.7, 132.1, 130.5, 130.4, 129.5, 128.0, 125.5, 103.1.

General Procedure for S$_N$Ar of 2-Aminobiphenyl to Generate Library of Benzofurazan Replacements

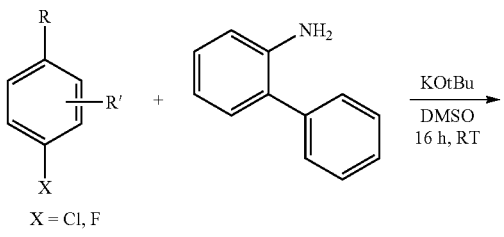

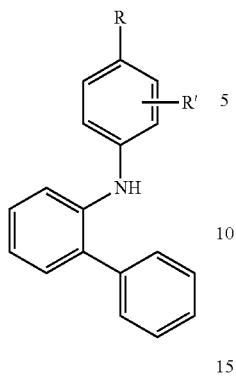

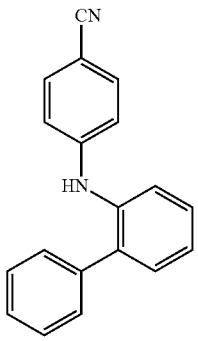

SF-3-078

To a solution of the aryl fluoride or chloride (1 equiv) and 2-aminobiphenyl (1 equiv) in anhydrous DMSO (0.2 M) at room temperature was added potassium tert-butoxide (2 equiv). After 16 h, the reaction mixture was diluted with water, and extracted into EtOAc (×3). The EtOAc extractions were combined, washed with water (×5), brine, dried (Na$_2$SO$_4$), filtered and concentrated. The crude residue was dry-loaded onto silica gel and purified by flash column chromatography (CH$_2$Cl$_2$/Hex/EtOAc, 10:10:1) to afford the target compound.

$\delta_H$ (CDCl$_3$, 400 MHz) 7.46-7.31 (m, 10H, Ar), 7.19 (t, J=6.8, 1H, Ar), 6.89 (d, J=7.6, 2 H, Ar), 5.81 (br s, 1H, NH); $\delta_C$ (CDCl$_3$, 100 MHz) 148.3, 138.4, 137.0, 134.8, 133.8, 131.3, 129.1, 128.9, 128.4, 127.8, 124.4, 121.9, 119.9, 115.0, 101.5.

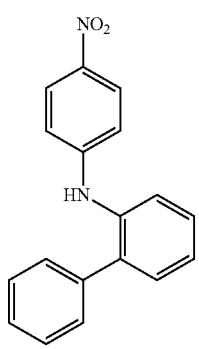

SF-3-068

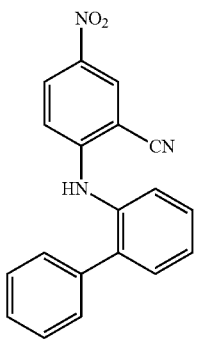

SF-3-079

$\delta_H$ (CDCl$_3$, 400 MHz) 8.10 (d, J=8.4, 2 H, Ar), 7.51-7.32 (m, 8H, Ar), 7.26 (t, J=6.4, 1H, Ar), 6.88 (d, J=8.4, 2 H, Ar), 6.02 (s, 1H, NH); $\delta_C$ (CDCl$_3$, 100 MHz) 150.5, 138.2, 136.5, 135.4, 131.3, 129.1, 128.9, 128.5, 127.9, 126.2, 125.1, 122.7, 113.7.

$\delta_H$ (CDCl$_3$, 400 MHz) 8.31 (d, J=2.4, 1H, Ar), 8.10 (dd, J=9.6, 2.4, 1H, Ar), 7.50-7.24 (m, 9H, Ar), 6.92 (d, J=9.6, 1H, Ar), 6.79 (s, 1H, NH); $\delta_C$ (CDCl$_3$, 100 MHz) 152.2, 138.5, 137.9, 137.5, 134.4, 131.6, 129.7, 129.5, 128.9, 128.8, 128.6, 128.2, 127.6, 125.4, 115.2, 112.5, 96.7.

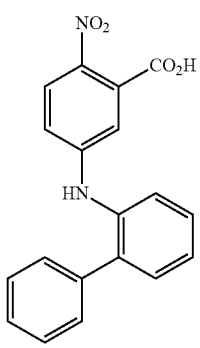

SF-3-070

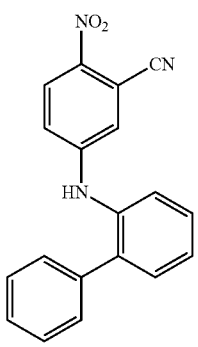

SF-3-080

$\delta_H$ (CDCl$_3$+MeOH-d$_4$, 400 MHz) 7.78 (d, J=8.8, 1H, Ar), 7.38-7.15 (m, 10H, Ar), 6.82 (br s, 1H, NH), 7.77 (d, J=8.8, 1H, Ar); $\delta_C$ (CDCl$_3$, 100 MHz) 150.4, 138.3, 136.1, 131.3, 128.9, 128.7, 128.5, 127.7, 127.0, 125.6, 123.6, 113.6, 112.8.

$\delta_H$ (CDCl$_3$, 400 MHz) 8.12 (d, J=9.6, 1H, Ar), 7.48-7.25 (m, 9H, Ar), 7.12 (s, 1H, Ar), 6.98 (d, J=9.6, 1H, Ar), 6.33 (s, 1H, NH); $\delta_C$ (CDCl$_3$, 100 MHz) 150.3, 138.7, 137.9, 136.7, 135.1, 131.6, 128.9, 128.8, 128.7, 128.1, 126.7, 123.9, 119.3, 116.4, 115.7, 110.2.

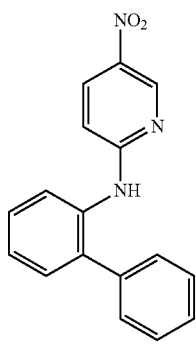

SF-3-081

$\delta_H$(CDCl$_3$, 400 MHz) 8.93 (d, J=2.4, 1H, NH), 8.17 (dd, J=9.6, 2.4, 1H, Ar), 7.68 (d, J=7.6, 1H, Ar), 7.46-7.22 (m, 9H, Ar), 6.66 (d, J=9.6, 1H, Ar); $\delta_C$ (CDCl$_3$, 100 MHz) 159.6, 146.7, 138.0, 135.9, 124.9, 133.3, 131.2, 129.1, 128.9, 128.6, 128.0, 126.1, 123.8, 106.3.

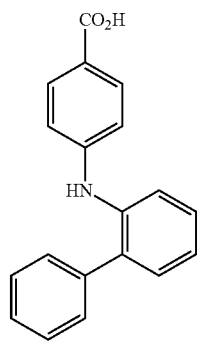

SF-3-093B $\delta_H$ (CDCl$_3$, 400 MHz) 7.96 (d, J=7.6, 2 H, Ar), 7.49 (d, J=8.4, 1H, Ar), 7.45-7.30 (m, 7H, Ar), 7.17 (t, J=6.8, 1H, Ar), 6.94 (d, J=7.6, 2 H, Ar), 5.85 (br s, 1H, NH); $\delta_C$ (CDCl$_3$, 100 MHz) 172.0, 149.3, 138.5, 137.5, 134.3, 132.3, 131.1, 129.2, 128.9, 128.3, 127.7, 123.8, 121.5, 120.0, 114.4.

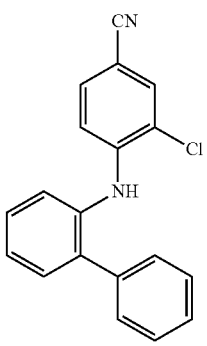

SF-3-083

$\delta_H$(CDCl$_3$, 400 MHz) 7.52 (s, 1H, Ar), 7.42-7.23 (m, 10H, Ar), 7.09 (d, J=8.8, 1H, Ar), 6.41 (br s, 1H, NH); $\delta_C$ (CDCl$_3$, 100 MHz) 144.9, 138.1, 136.3, 135.9, 133.0, 131.9, 131.3, 128.8, 128.5, 127.9, 125.6, 123.5, 120.0, 118.6, 113.0, 101.4.

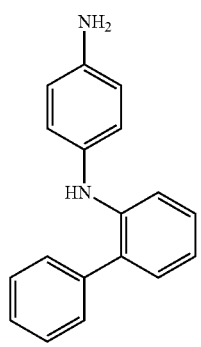

SF-3-098

$\delta_H$ (CDCl$_3$, 400 MHz) 7.53-7.42 (m, 4H, Ar), 7.37 (d, J=6.8, 1H, Ar), 7.27 (t, J=6.8, 2H, Ar), 7.04 (d, J=7.6, 1H, Ar), 6.94 (d, J=7.6, 2 H, Ar), 6.86 (t, J=7.6, 1H, Ar), 6.66 (d, J=7.6, 2 H, Ar), 5.48 (br s, 1H, NH), 3.40 (br s, 2H, NH$_2$); $\delta_C$ (CDCl$_3$, 100 MHz) 142.9, 141.9, 139.3, 134.1, 130.6, 129.4, 129.0, 128.9, 128.3, 127.3, 123.8, 118.9, 116.3, 114.2.

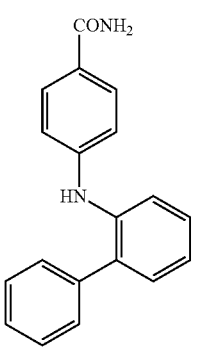

SF-3-093A $\delta_H$ (CDCl$_3$, 400 MHz) 7.68 (d, J=7.6, 2 H, Ar), 7.48-7.27 (m, 8H, Ar), 7.12 (t, J=6.8, 1H, Ar), 6.94 (d, J=7.6, 2 H, Ar), 5.95 (br s, 2H, NH$_2$), 5.78 (br s, 1H, NH); $\delta_C$ (CDCl$_3$, 100 MHz) 169.1, 147.7, 138.6, 138.0, 133.8, 131.1, 129.2, 128.9, 128.3, 127.7, 124.2, 123.3, 120.7, 115.1.

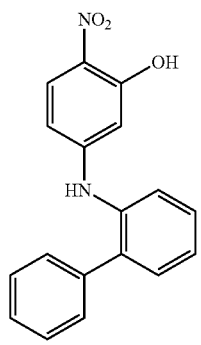

SF-3-101

$\delta_H$ (CDCl$_3$, 400 MHz) 11.24 (s, 1H, OH), 7.94 (d, J=9.6, 1H, Ar), 7.50-7.23 (m, 9H, Ar), 6.48 (s, 1H, Ar), 6.34 (dd, J=9.6, 1.6, 1H, Ar), 6.08 (s, 1H, NH); $\delta_C$ (CDCl$_3$, 100 MHz) 158.3, 153.4, 138.0, 136.2, 135.6, 131.3, 129.0, 128.9, 128.5, 127.9, 127.6, 125.9, 124.1, 108.5, 100.0.

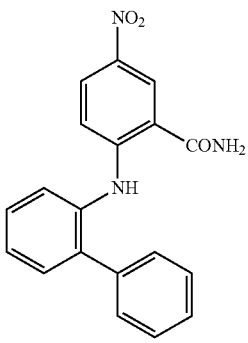

SF-3-103A

δ$_H$ (CDCl$_3$, 400 MHz) 10.36 (s, 1H, NH), 8.36 (s, 1H, Ar), 7.98 (dd, J=9.6, 2.4, 1H, Ar), 7.46-7.22 (m, 9H, Ar), 6.93 (d, J=9.6, 1H, Ar); δ$_C$ (CDCl$_3$, 100 MHz) 170.0, 152.7, 138.4, 137.9, 136.6, 135.8, 131.4, 128.9, 128.5, 128.4, 127.6, 126.6, 125.5, 125.4, 113.6, 112.7.

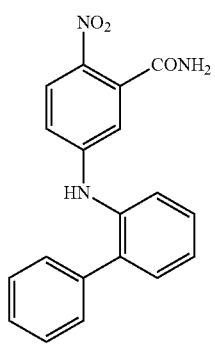

SF-3-104A

δ$_H$ (CDCl$_3$+MeOH-d$_4$, 400 MHz) 7.78 (d, J=9.6, 1H, Ar), 7.31-7.07 (m, 9H, Ar), 6.59 (d, J=9.6, 1H, Ar), 6.56 (s, 1H, Ar); δ$_C$ (CDCl$_3$, 100 MHz) 171.1, 151.1, 138.5, 136.8, 136.0, 135.2, 135.0, 131.2, 128.7, 128.4, 128.3, 127.4, 127.3, 125.9, 124.6, 112.9, 112.2.

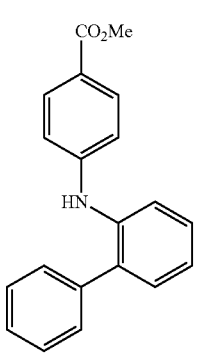

SF-3-105

δ$_H$ (CDCl$_3$, 400 MHz) 7.88 (d, J=8.8, 2 H, Ar), 7.49-7.29 (m, 8H, Ar), 7.14 (t, J=8.0, 1H, Ar), 6.92 (d, J=8.8, 2 H, Ar), 5.78 (br s, 1H, NH), 3.86 (s, 3H, OMe); δ$_C$ (CDCl$_3$, 100 MHz) 166.9, 148.4, 138.5, 137.8, 134.0, 131.5, 131.1, 129.2, 128.9, 128.3, 127.7, 123.5, 121.1, 121.0, 114.7, 51.7.

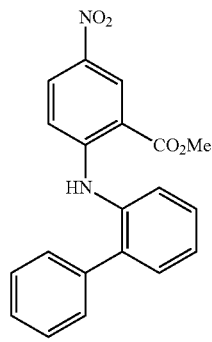

SF-3-106

δ$_H$ (CDCl$_3$, 400 MHz) 9.94 (br s, 1H, NH), 8.81 (s, 1H, Ar), 8.02 (d, J=8.8, 1H, Ar), 7.47-7.24 (m, 9H, Ar), 6.87 (d, J=8.8, 1H, Ar), 3.86 (s, 3H, OMe); δ$_C$ (CDCl$_3$, 100 MHz) 167.4, 153.0, 138.4, 138.3, 137.1, 135.5, 131.5, 129.2, 128.9, 128.8, 128.6, 128.5, 127.7, 127.0, 126.1, 113.2, 109.9, 52.3.

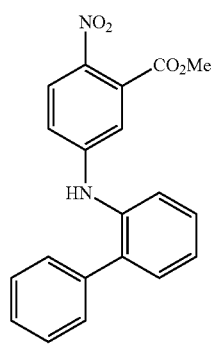

SF-3-107

δ$_H$ (CDCl$_3$, 400 MHz) 7.97 (d, J=8.4, 1H, Ar), 7.51-7.16 (m, 9H, Ar), 6.92-6.84 (m, 2H, Ar), 6.09 (br s, 1H, NH), 3.89 (s, 3H, OMe); δ$_C$ (CDCl$_3$, 100 MHz) 167.4, 149.8, 138.0, 135.9, 135.8, 132.1, 132.0, 131.4, 129.0, 128.9, 128.7, 128.6, 128.1, 128.0, 127.2, 125.6, 123.0, 53.8.

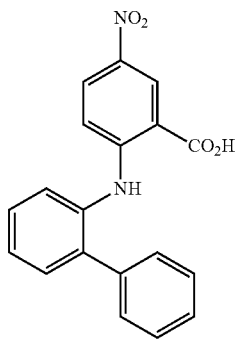

SF-3-103B 2-([1,1'-Biphenyl]-2-ylamino)-5-nitrobenzoic. To a solution of 2-fluoro-5-nitrobenzonitrile (690 mg, 4.13 mmol, 1 equiv) and 2-aminobiphenyl (700 mg, 4.13 mmol, 1 equiv) in anhydrous DMSO (20 mL) at room temperature was added potassium tert-butoxide (930 mg, 8.26 mmol, 2 equiv). After 16 h, the reaction mixture was diluted with water, and extracted into EtOAc (×3). The EtOAc extractions were combined, washed with water (×5), brine, dried (Na₂SO₄), filtered and concentrated. The crude residue was dry-loaded onto silica gel and purified by flash column chromatography (CH₂Cl₂/Hex/EtOAc, 10:10:1) to afford 2-([1,1'-biphenyl]-2-ylamino)-5-nitrobenzonitrile as an orange solid (728 mg, 56%): $\delta_H$ (CDCl₃, 400 MHz) 8.31 (d, J=2.4, 1H, Ar), 8.10 (dd, J=9.6, 2.4, 1H, Ar), 7.50-7.24 (m, 9H, Ar), 6.92 (d, J=9.6, 1H, Ar), 6.79 (s, 1H, NH); $\delta_C$ (CDCl₃, 100 MHz) 152.2, 138.5, 137.9, 137.5, 134.4, 131.6, 129.7, 129.5, 128.9, 128.8, 128.6, 128.2, 127.6, 125.4, 115.2, 112.5, 96.7), which was subsequently hydrolyzed (1.17 mmol scale) with NaOH (140 mg, 3.52 mmol, 2 equiv) in a 1:1:1 mixture of dioxane/EtOH/H₂O (12 mL) at reflux for 48 h. The reaction mixture was concentrated to dryness, and then partitioned between Et₂O and H₂O to remove neutral organics. The aqueous layer was acidified with 1M HCl, and then extracted with EtOAc (×3). The EtOAc extractions were combined, washed with brine, dried (Na₂SO₄), filtered and concentrated. The crude residue was dry-loaded onto silica gel and purified by flash column chromatography (CH₂Cl₂/MeOH/AcOH, 92:7:1) to deliver the title compound 2-([1,1'-biphenyl]-2-ylamino)-5-nitrobenzoic acid (SF-3-103B) as an orange solid (293 mg, 75%): $\delta_H$ (CDCl₃+MeOH-d4, 400 MHz) 10.01 (s, 1H, OH), 8.80 (d, J=2.4, 1H, NH), 7.98 (dd, J=9.6, 2.4, 1H, Ar), 7.43-7.17 (m, 11H, Ar), 6.82 (d, J=9.6, 1H, Ar); $\delta_C$ (CDCl₃, 100 MHz) 169.2, 153.2, 138.3, 138.2, 137.0, 135.4, 131.4, 129.5, 129.1, 128.8, 128.5, 128.4, 127.5, 126.9, 126.0, 113.0, 110.2.

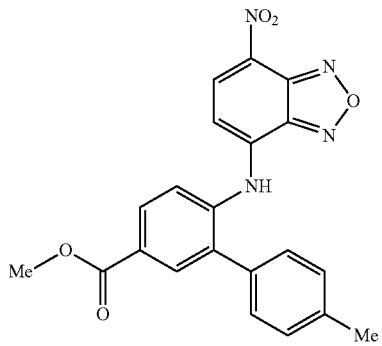

3jc48-3

Methyl 4'-methyl-6-((7-nitrobenzo[c][1,2,5]oxadiazol-4-yl)amino)-[1,1'-biphenyl]-3-carboxylate (3jc48-3). 4-Fluoro-7-nitrobenzo[c][1,2,5]oxadiazole(34) ("NDB-F"; 40 mg, 0.22 mmol) and methyl 6-amino-4'-methyl-[1,1'-biphenyl]-3-carboxylate (1.1 eq) were dissolved in MeCN (2 mL). The reaction mixture was heated at 60° C. for 20 hours. The reaction mixture was cooled, reduced in vacuo and partitioned between EtOAC/H₂O. The organic layer was washed twice with H₂O, sat. NaCl, dried over NaSO₄ and reduced in vacuo. The crude mixture was purified by column chromatography (hexane/EtOAc) to afford the corresponding title compound (25 mg, 70%): $\delta_H$ (d₆-DMSO, 400 MHz) 11.02 (s, 1H, NH), 8.42 (d, J=8.8, 1H, Ar), 8.07 (d, J=8.4, 1H, Ar), 8.03 (s, 1H, Ar), 7.67 (d, J=8.4, 1H, Ar), 7.34 (d, J=7.6, 2 H, Ar), 7.16 (d, J=7.6, 2 H, Ar), 6.24 (d, J=8.8, 1H, Ar), 3.91 (s, 3H, CO₂Me), 2.25 (s, 3H, Me); $\delta_C$ (d₆-DMSO, 100 MHz) 166.0, 144.8, 144.5, 143.5, 138.9, 137.8, 137.6, 134.9, 132.3, 129.7, 129.6, 129.5, 128.7, 128.6, 103.3, 52.9, 21.1; m/z 405 [M+H]⁺. $t_R$=27.54 (94.30%).

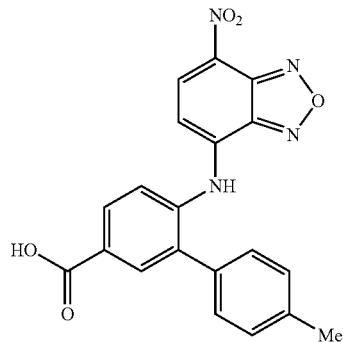

3jc56-3

4'-Methyl-6-((7-nitrobenzo[c][1,2,5]oxadiazol-4-yl)amino)-[1,1'-biphenyl]-3-carboxylic acid (3jc56-3). Methyl ester 3jc48-3 (20 mg, 0.050 mmol) 1:1 THF/H₂O (2 mL) was treated with 2 M LiOH.H₂O (38 μL, 0.075 mmol) at room temperature for 20 h. The reaction mixture was neutralized with 1 M HCl and extracted with EtOAc (×2). The organic layer was washed with sat. NaCl, dried over NaSO₄, reduced in vacuo and lyophilized to give the title compound as a red solid (18 mg, 98%). General procedure gave the title compound as a red solid 56 mg, 88%. $\delta_H$ (d₆-DMSO, 400 MHz) 13.20 (br s, 1H, CO₂H), 11.01 (br s, 1H, NH), 8.40 (d, J=8.4, 1H, Ar), 8.05-8.00 (m, 2H, Ar), 7.64 (d, J=8.4, 1H, Ar), 7.33 (d, J=7.6, 2 H, Ar), 7.14 (d, J=7.6, 2 H, Ar), 6.22 (d, J=8.4, 1H, Ar), 2.23 (s, 3H, Me); $\delta_C$ (d₆-DMSO, 100 MHz) 171.7, 149.5, 149.2, 148.3, 143.9, 143.6, 142.5, 139.8, 137.3, 135.6, 134.6, 134.4, 133.5, 133.3, 128.1, 107.8.

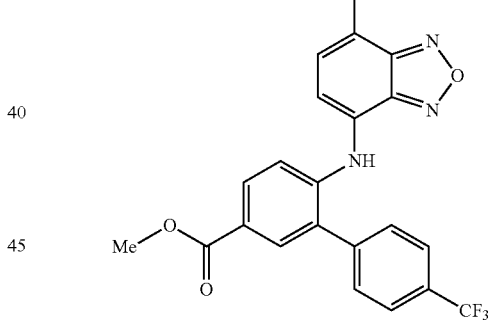

4jc23-4

Methyl 6-((7-nitrobenzo[c][1,2,5]oxadiazol-4-yl)amino)-4'-(trifluoromethyl)-[1,1'-biphenyl]-3-carboxylate.

4-Fluoro-7-nitrobenzo[c][1,2,5]oxadiazole(34) ("NDB-F"; 40 mg, 0.22 mmol) and methyl 6-amino-4'-(trifluoromethyl)-[1,1'-biphenyl]-3-carboxylate (1.1 eq) were dissolved in MeCN (2 mL). The reaction mixture was heated at 60° C. for 20 hours. The reaction mixture was cooled, reduced in vacuo and partitioned between EtOAC/H₂O. The organic layer was washed twice with H₂O, sat. NaCl, dried over NaSO₄ and reduced in vacuo. The crude mixture was purified by column chromatography (hexane/EtOAc) to afford the corresponding title compound as a red solid (63 mg, 63%): $\delta_H$ (d₆-DMSO, 400 MHz) 11.00 (br s, 1H, NH), 8.45 (d, J=8.8, 1H, Ar), 8.13 (dd, J=8.4, 2.0, 1H, Ar), 8.08 (d, J=2.0, 1H, Ar), 7.77-7.63 (m, 5H, Ar), 6.37 (d, J=8.8, 1H, Ar), 3.91 (s, 3H, CH₃); $\delta_C$ (d₆-DMSO, 100 MHz) 165.8, 144.9, 144.5, 143.3, 142.0, 140.0, 137.5, 137.3, 132.5, 130.7, 129.9, 129.5, 128.6, 125.9, 124.0, 103.7, 52.9; m/z 459 [M+H]⁺. $t_R$=27.37 (92.02%).

JY-5-195

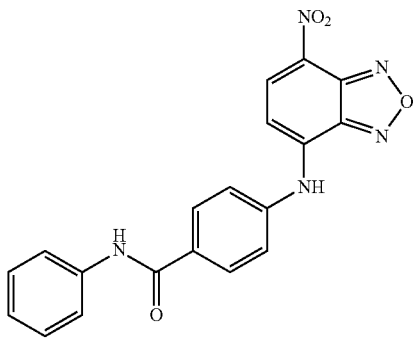

4-((7-Nitrobenzo[c][1,2,5]oxadiazol-4-yl)amino)-N-phenylbenzamide. A round bottom flask was charged with JY-3-094 (0.46 mmol), solvated with anhydrous CH$_2$Cl$_2$ (4.6 mL) and stirred at 0° C. under an inert atmosphere. (COCl)$_2$ (2 eq.) was added dropwise, followed by one drop of DMF, and the reaction was allowed to stir for 1 h under an inert atmosphere. The excess (COCl)$_2$ and CH$_2$Cl$_2$ were removed in vacuo and azeotroped twice with anhydrous CH$_2$Cl$_2$. The residue was re-solvated with anhydrous CH$_2$Cl$_2$ (4.6 mL) at 0° C. DIPEA (4 eq.) was added and the reaction mixture was allowed to stir for 10 min under an inert atmosphere. Aniline (1.2 eq.) was added and the reaction mixture was allowed to stir overnight at RT. The next day, the reaction solution was concentrated in vacuo and the residue was re-dissolved in EtOAc. The EtOAc layer was washed with sat. NaHCO$_3$, 1M HCl (×5), and dried with brine, Na$_2$SO$_4$, and re-concentrated in vacuo to give the title compound as a red solid (16%): δ$_H$ (d$_6$-DMSO, 400 MHz) 11.17 (1H, s, Ar—NH), 10.29 (1H, s, Ar—NH), 8.60 (1H, d, Ar—H, J=8.8 Hz), 8.08 (2H, d, Ar—H, J=8.4 Hz), 7.79 (2H, d, Ar—H, J=7.6 Hz), 7.65 (2H, d, Ar—H, J=8 Hz), 7.36 (2H, t, Ar—H, J=7.8 Hz), 7.11 (1H, t, Ar—H, J=7 Hz), 6.95 (1H, d, Ar—H, J=8.8 Hz); δ$_C$ (d$_6$-DMSO, 100 MHz) 165, 145.6, 144.5, 141.5, 141.4, 139.5, 137.8, 132.2, 129.7, 129.6, 129, 128.8, 124.5, 124.1, 122.9, 120.7, 120.5, 103.3. t$_R$=24.42 (93.51%).

JY-5-261

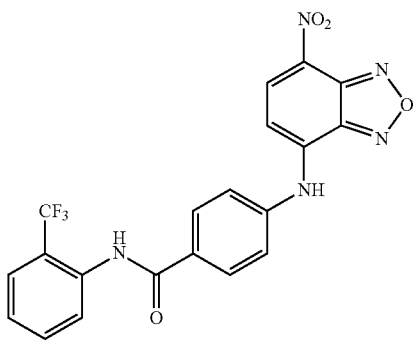

4-((7-Nitrobenzo[c][1,2,5]oxadiazol-4-yl)amino)-N-(2-(trifluoromethyl)phenyl)benzamide. A round bottom flask was charged with JY-3-094 (0.46 mmol), solvated with anhydrous CH$_2$Cl$_2$ (4.6 mL) and stirred at 0° C. under an inert atmosphere. (COCl)$_2$ (2 eq.) was added dropwise, followed by one drop of DMF, and the reaction was allowed to stir for 1 h under an inert atmosphere. The excess (COCl)$_2$ and CH$_2$Cl$_2$ were removed in vacuo and azeotroped twice with anhydrous CH$_2$Cl$_2$. The residue was re-solvated with anhydrous CH$_2$Cl$_2$ (4.6 mL) at 0° C. DIPEA (4 eq.) was added and the reaction mixture was allowed to stir for 10 min under an inert atmosphere. 2-Trifluoromethylaniline (1.2 eq.) was added and the reaction mixture was allowed to stir overnight at RT. The next day, the reaction solution was concentrated in vacuo and the residue was re-dissolved in EtOAc. The EtOAc layer was washed with sat. NaHCO$_3$, 1M HCl (×5), and dried with brine, Na$_2$SO$_4$, and re-concentrated in vacuo to give the title compound as red crystals (36%): δ$_H$ (d$_6$-DMSO, 400 MHz) 11.17 (1H, s, Ar—NH), 10.20 (1H, s, Ar—NH), 8.58 (1H, d, Ar—H, J=8.4 Hz), 8.07 (2H, d, Ar—H, J=8.4 Hz), 7.82 (1H, d, Ar—H, J=8 Hz), 7.63 (2H, t, Ar—H, J=7.4 Hz), 7.66 (2H, d, Ar—H, J=8.4 Hz), 7.56 (2H, d, Ar—H, J=6.8 Hz), 6.98 (1H, d, Ar—H, J=8.8 Hz); δ$_C$ (d$_6$-DMSO, 100 MHz) 165.8, 145.6, 144.5, 141.6, 141.5, 137.8, 136.1, 133.5, 133.2, 131.7, 131.4, 131.1, 129.7, 129.5, 127.9, 127.1, 126.9, 126.7, 124.6, 123.1, 113.9, 103.5. t$_R$=24.87 (90.52%).

Biological Assays

EMSAs.

These were performed essentially as described previously (23). Briefly, Ni$^+$-agarose-purified His$_6$-tagged c-Myc bHLH-ZIP domain (residues 353-437) was used for all binding assays as was the His$_6$-tagged 151 residue isoform of Max, otherwise referred to as Max(S) (residues 2-151) (21). For each binding reaction, the proteins were allowed to heterodimerize at a concentration of 30 nM each in the presence of 20 nM of a 5'-HEX-tagged double-stranded 22-base pair oligonucleotide 5'-hexachlorofluoresceine-CACCCGGT-CACGTGGCCTACAC-3' (SEQ ID NO: 1) containing a consensus c-Myc binding site (CACGTG) and the indicated concentration of small molecule inhibitor. Control reactions contained the same oligonucleotide in the presence of 60 nM of the 160 residue isoform of Max referred to as Max(L) (21). All binding reactions were prepared in a buffer consisting of PBS (pH 7.3), 1 mmol/L EDTA, 0.1% NP40, 5% glycerol, 1 mmol/L DTT, and 0.4 mg/mL bovine serum albumin. Electrophoresis was performed on 8% polyacrylamide/bisacrylamide (80:1) gels in 0.5 M Tris-borate EDTA (23). Each reaction was run on at least three separate occasions.

Growth Inhibition Assays.

These were performed using HL60 human promyelocytic leukemia cells or Daudi Burkitt lymphoma cells essentially as described previously (23). Briefly, cells were seeded into 96 well dishes (5000 cells/well and 10,000 cells/well for HL60 and Daudi cells, respectively). Growth medium consisted of RPMI medium supplemented with Penicillin/Streptomycin, glutamine and 10% fetal bovine serum. The indicated concentrations of each compound were then added and 10-point growth inhibition assays were performed 3-5 days later using the MTT assay. Each point was performed in quadruplicate.

c-Myc-Max Electrophoretic Mobility Shift Assays (EMSAs).

EMSAs were performed essentially as described utilizing bacterially-expressed recombinant proteins purified nearly to homogeneity.(23) Experiments with Max homodimers used the His6-tagged 160 amino acid isoform of the protein, termed Max(L), which homodimerizes and binds DNA well. For studies with Myc-Max heterodimers, the His6-tagged 151 residue isoform of Max [Max(S)] was used, which binds DNA well as a heterodimer with Myc but poorly as a homodimer.(23) Recombinant Myc protein, expressed in the pET151 vector, consisted of the His6-TEV protease substrate-tagged 85 amino acid bHLH-ZIP domain. (23) Each protein was purified by Ni-agarose affinity chromatography as previously described. (23) The His6-TEV tag was removed from the Myc protein by TEV protease cleavage followed by re-purification using Ni-agarose affinity chromatography to remove the His6-TEV protease and the cleaved His6-TEV tag as previously described. Binding assays were performed with 30 nM of each protein and 30 nM of a 6-carboxy-2',4,4',5',7, 7'-hexachlorofluorescein (HEX)-tagged double-stranded oligonucleotide containing a consensus Myc binding site (IDT, Coralville, Iowa).(23)

Growth Inhibition Assays.

Daudi Burkitt lymphoma and HL60 promyelocytic leukemia cells were maintained in RPMI medium supplemented with 10% fetal bovine serum.(23) For growth inhibition studies, $3\times10^3$ cells were seeded in 96 well plates in the presence of serial dilutions of each compound. A total of 10 dilutions, ranging from 0.1 to 50 µM were performed for each compound. Standard MTT assays (23) were used to quantify cell number 3-4 days later and compared to wells exposed to DMSO vehicle only. Each point was assayed in quadruplicate with the results being presented as the mean+/−1 standard error.

Co-Immunoprecipitation (Co-IP) Assays.

Co-IP assays were performed essentially as described previously.(23) Briefly, $5\times10^6$ HL60 cells (>90% viable) in log-phase growth were treated in suspension for 4-6 h with the stated concentration of 3jc48-3. As a negative control, samples exposed to DMSO vehicle only were included and processed in parallel. Treated cells were collected by centrifugation, washed twice in ice-cold PBS and lysed in IP Buffer. 300 µg of cleared lysate was then precipitated with a 1:200 dilution of anti-Max antibody(23) followed by subsequent precipitation with protein G-Sepharose using conditions recommended by the supplier (Santa Cruz Biotechnology, Inc. Santa Cruz, Calif.). The precipitate was washed three times in IP buffer, boiled in running buffer and resolved by 10% SDS-PAGE. After electrotransfer of the proteins to a PVDF membrane (Millipore Corp. Billercica, Mass.), the blot was probed with a 1:1000 dilution of anti-Myc monoclonal antibody (9E10, Santa Cruz Biotechnology, Santa Cruz, Calif.). Blots were developed using a Pierce ECL Plus enhanced chemiluminescence kit according to the directions of the supplier (Thermo-Fisher, Pittsburgh, Pa.).

Cell Cycle Analysis.

Sub-confluent cultures of cells at >90% viability were plated into fresh medium at densities that were typically about 10% of those attained at the point of density arrest. The next day, Myc inhibitors at the stated concentrations were added for 24-48 hr. The cells were then harvested, washed twice in PBS and stained with propidium iodide as previously described(23). Cell cycle analyses were performed on a BD FACSCalibur™ flow cytometer (Becton Dickinson, Inc. Franklin Lakes, N.J.) and analyzed using ModFit LT 3.3 (Verity Software House, Topsham, Me.).

Assay of Myc Reporter Gene Expression.

The generic reporter vector pGL4.28(luc2CP/minP/Hygro) (Promega Corp., Madison Wis.), which is specifically designed to reduce anomalous transcription and which contains a highly de-stabilized luciferase reporter was used to assess the effects of Myc inhibitors. A double-stranded palindromic oligonucleotide containing three tandem Myc-responsive E-box elements (5'-TCGAGCCACGTGGC-CACGTGGCCACGTGGC-3') (SEQ ID NO: 2) (E-boxes underlined) was self-annealed and cloned into an XhoI site just upstream of the minimal promoter element of this vector. A control vector containing this same oligonucleotide with mutant E-box sites (5'-TCGAGCCTCGAGGCCTCGAG-GCCTCGAGGC-3') (SEQ ID NO: 3) was used as a negative control. An additional vector was similarly constructed that contained a tandemly triplicated binding site for NF-kB (5'-TCGAGGGACTTTCCATGGGACTTTC-CATGGGACTTTCC-3') (SEQ ID NO: 4). After automated DNA sequencing to confirm the identity of its respective insert, each vector was then separately co-transfected into HeLa cells together with the vector pFR400, which encodes a mutant form of dihydrofolate reductase that facilitates the step-wise amplification of the plasmid and any co-transfected sequences in the presence of increasing concentrations of the folate antagonist methotrexate (MTX). After first selecting for stably transfected cells by growth in hygromycin, the resistant clones were pooled and grown in serial four-fold increasing concentrations of MTX ranging from 0.25-16 mM), thus allowing the luciferase signal originating from the first vector to be easily detected above background. No luciferase signal over background values could be obtained in unamplified cells or in amplified cells transfected with the mutant E-box-containing vector. An additional HeLa cell line was prepared that expressed a Renilla luciferase under the control of an SV40 early promoter (Promega).

TABLE 3

Generic ester prodrugs A and metabolically stable amides B of JY-3-094 to Improve Cellular Activity

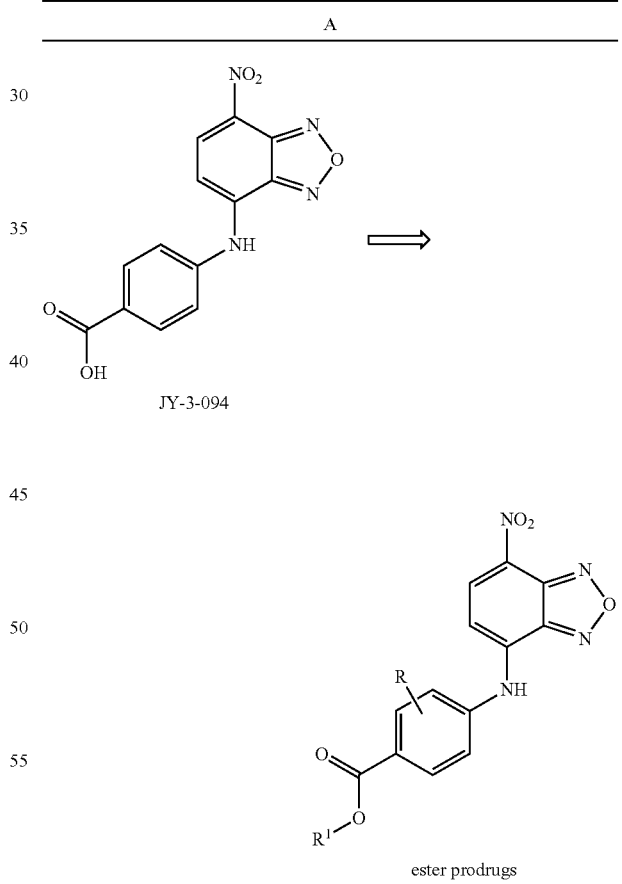

A

JY-3-094 ester prodrugs $R^1$ = alkyl, aryl, cycloalkyl, benzyl, $CH_2CF_3$, $CF_2CF_3$, $CH_2O(CO)CH_3$ R = H, alkyl, aryl, heteroaryl, CN, $CO_2H$, $CONH_2$, OH, halogen, $NH_2$, $NO_2$

TABLE 3-continued

Generic ester prodrugs A and metabolically stable amides B of JY-3-094 to Improve Cellular Activity

B

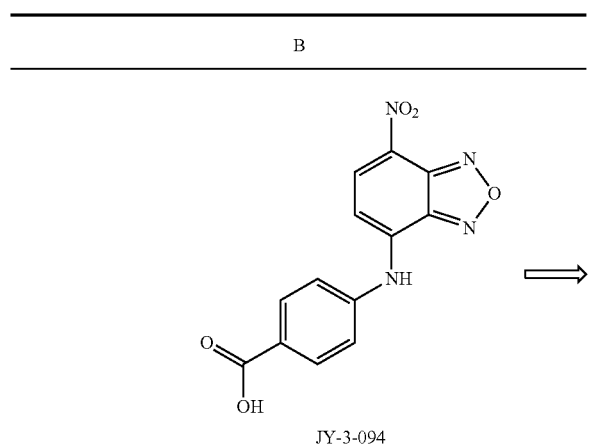

JY-3-094

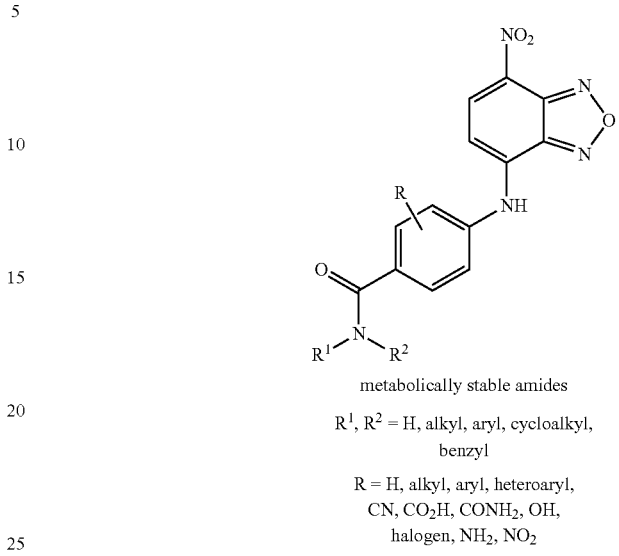

metabolically stable amides $R^1, R^2$ = H, alkyl, aryl, cycloalkyl, benzyl

R = H, alkyl, aryl, heteroaryl, CN, $CO_2H$, $CONH_2$, OH, halogen, $NH_2$, $NO_2$

TABLE 4

Amalgamation of the ortho-phenyl ring of 10074-G5 and the para-carboxylic acid of JY-3-094 towards potent c-Myc inhibitors.

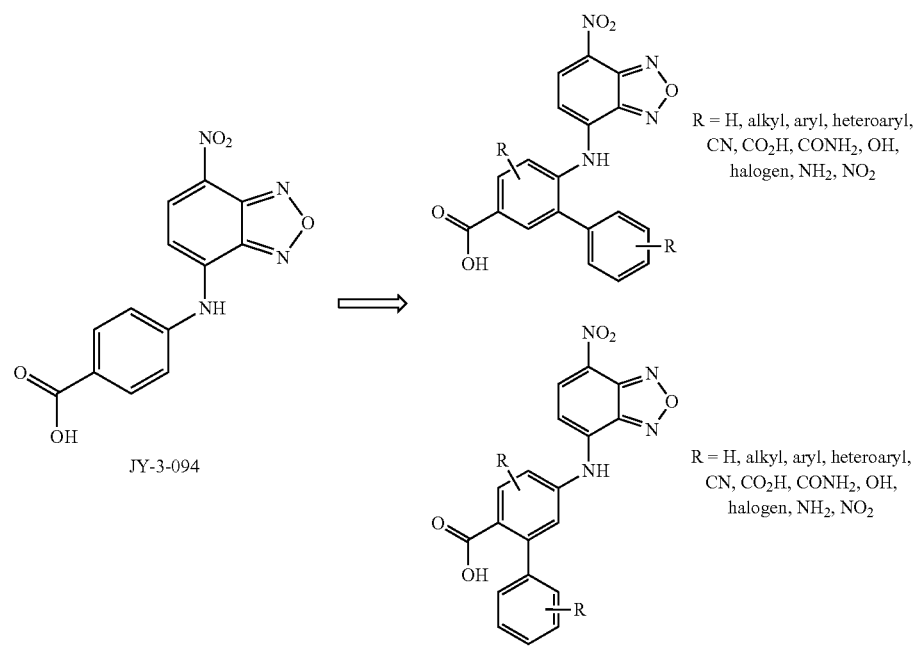

R = H, alkyl, aryl, heteroaryl, CN, $CO_2H$, $CONH_2$, OH, halogen, $NH_2$, $NO_2$ R = H, alkyl, aryl, heteroaryl, CN, $CO_2H$, $CONH_2$, OH, halogen, $NH_2$, $NO_2$

TABLE 5
Towards improved metabolic stability: Structural analogues of 10074-G5
Nitro Group Bioisosteres
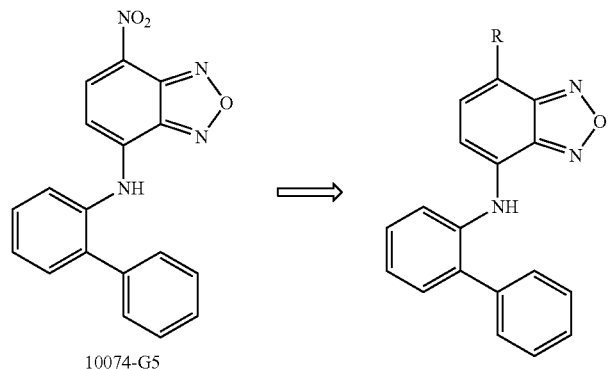
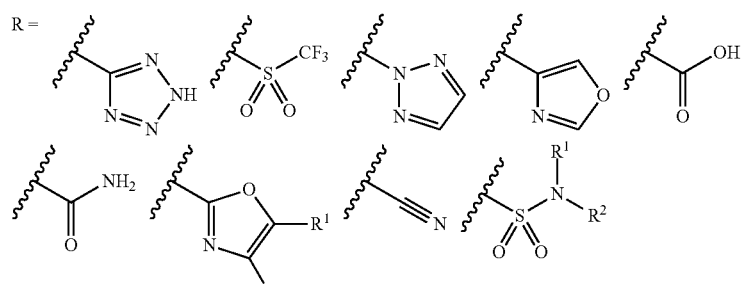
$R^1, R^2$ = H, alkyl, aryl
C—H -> C—F Bond Replacements to Block Oxidation of Phenyl Rings
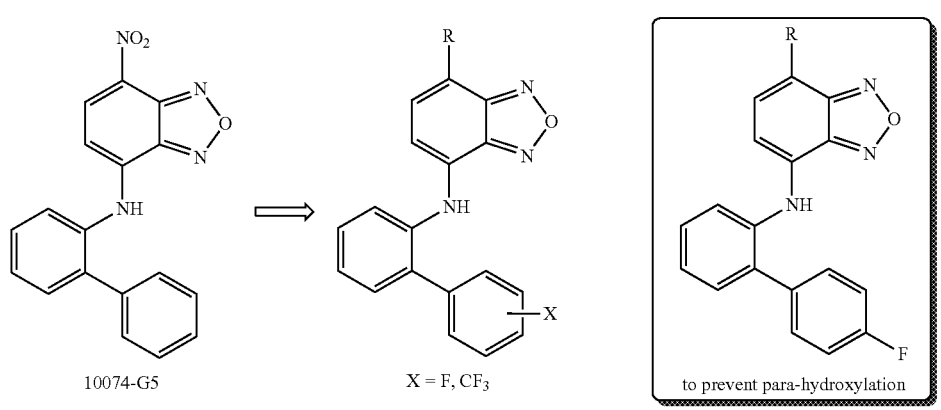
Replacement of Furazan Ring TABLE 5-continued
Towards improved metabolic stability: Structural analogues of 10074-G5
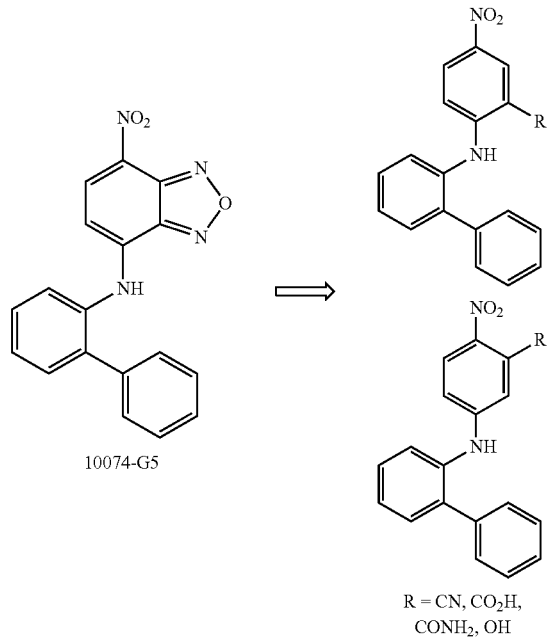
TABLE 6
Nitro bioisosteres of JY-3-094
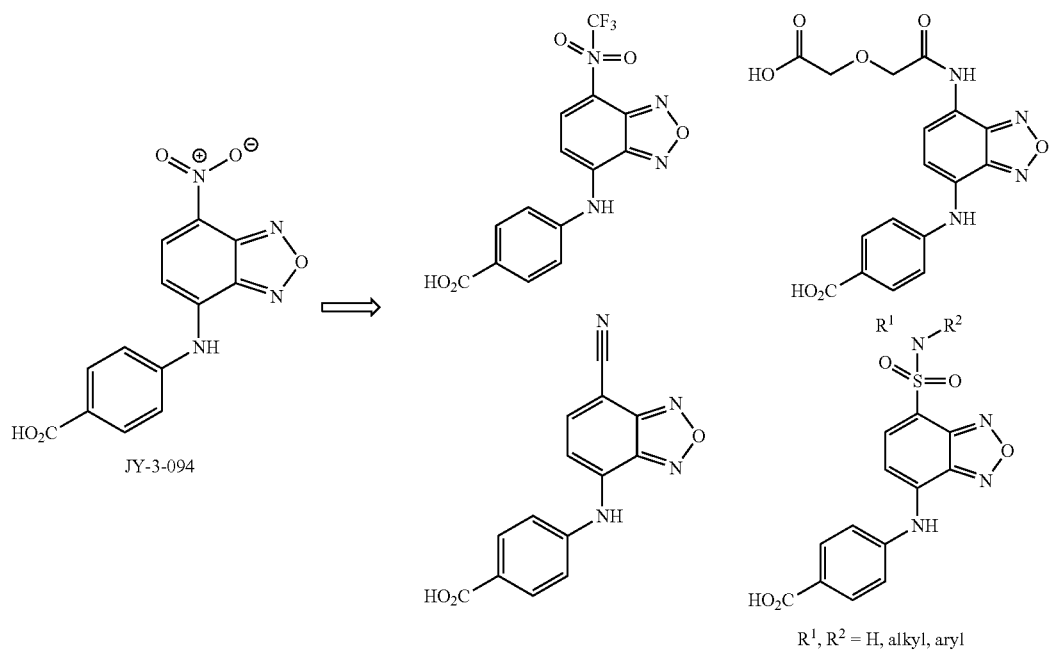

TABLE 6-continued
Nitro bioisosteres of JY-3-094
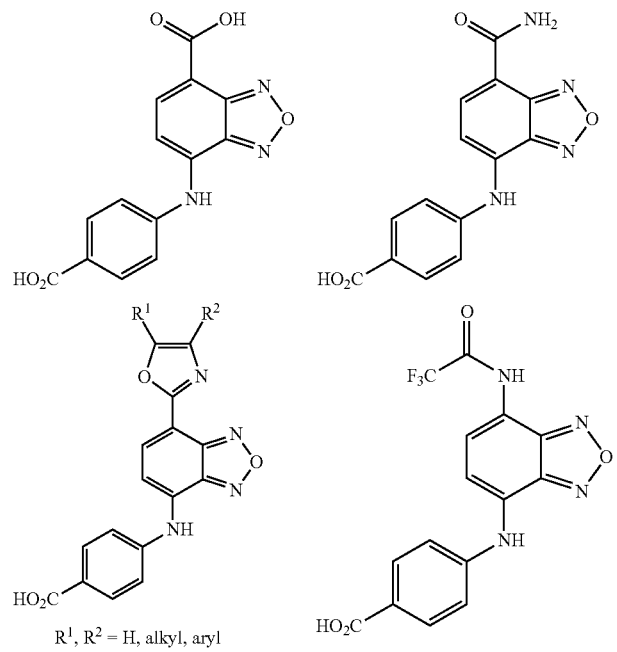
TABLE 7
Carboxylic acid bioisosteres of JY-3-094
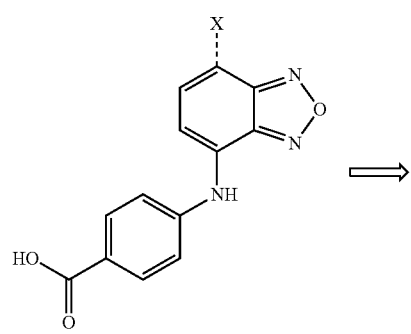
TABLE 7-continued
Carboxylic acid bioisosteres of JY-3-094
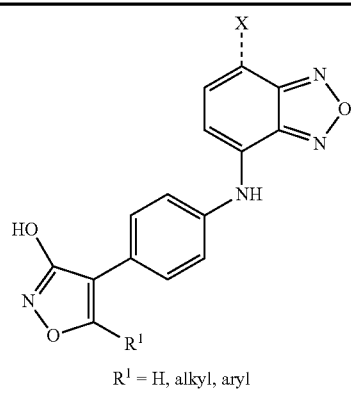
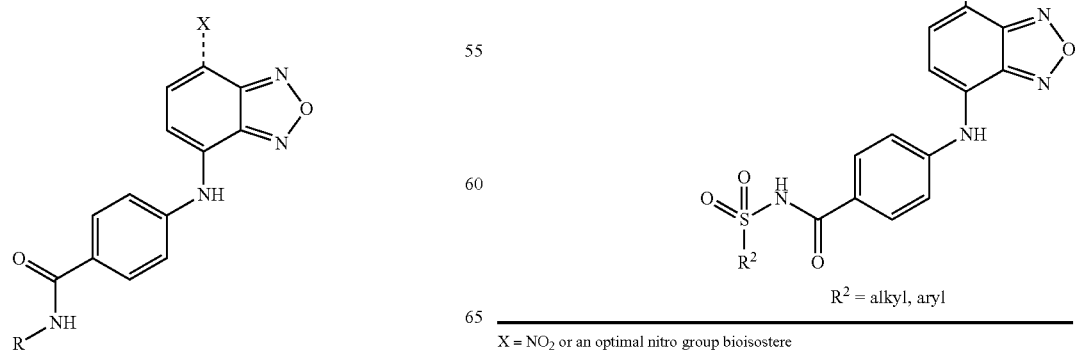
X = NO₂ or an optimal nitro group bioisostere TABLE 8
Structures and activities of c-Myc-Max dimerization inhibitors.
| Code Number | Structure | IC$_{50}$ Myc-Max[a] (uM) | IC$_{50}$ Max-Max[b] (uM) |
|---|---|---|---|
| 10074-G5 | 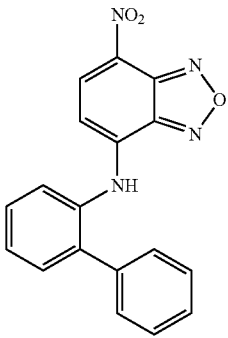 [SMILES: O=[N+]([O-])c1ccc(Nc2ccccc2-c2ccccc2)c2nonc12] | 154 | ND |
| JY-3-094 | 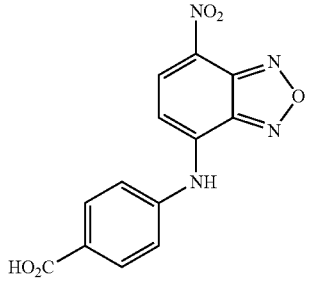 [SMILES: O=C(O)c1ccc(Nc2ccc([N+](=O)[O-])c3nonc23)cc1] | 33 | >100 |
| SF-3-103B | 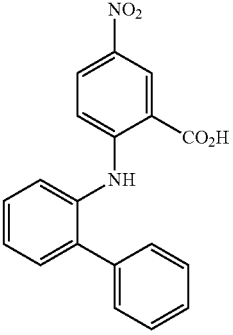 [SMILES: O=C(O)c1cc([N+](=O)[O-])ccc1Nc1ccccc1-c1ccccc1] | 84.0 | >100 |
| 3jc53-6 | 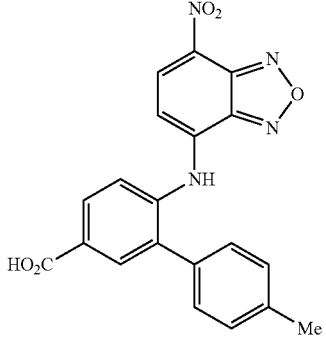 [SMILES: Cc1ccc(-c2cc(C(=O)O)ccc2Nc2ccc([N+](=O)[O-])c3nonc23)cc1] | >100 | >100 |

TABLE 8-continued

Structures and activities of c-Myc-Max dimerization inhibitors.

| Code Number | Structure | IC$_{50}$ Myc-Max[a] (uM) | IC$_{50}$ Max-Max[b] (uM) |
|---|---|---|---|
| 3jc48-3 | 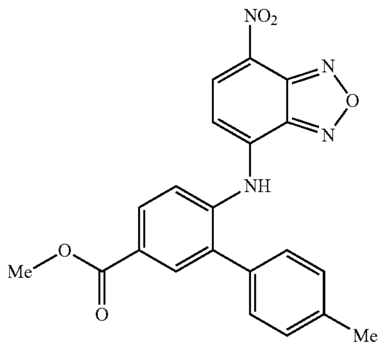 [SMILES: COC(=O)c1ccc(Nc2ccc([N+](=O)[O-])c3nonc23)c(-c2ccc(C)cc2)c1] | 34.8 | 60.6 |
| 4jc23-4 | 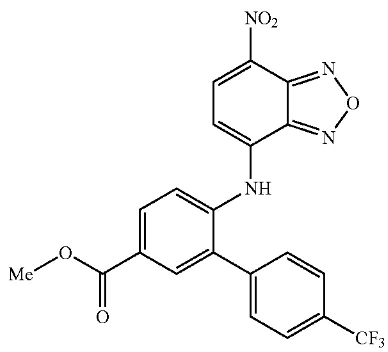 [SMILES: COC(=O)c1ccc(Nc2ccc([N+](=O)[O-])c3nonc23)c(-c2ccc(C(F)(F)F)cc2)c1] | 75 | >100 |
| SF-4-017 | 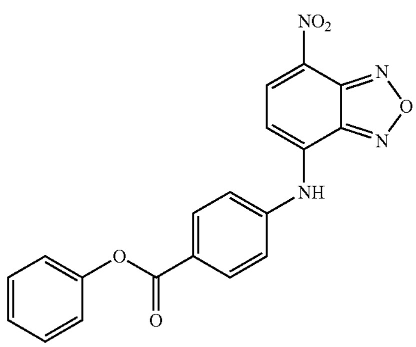 [SMILES: O=C(Oc1ccccc1)c1ccc(Nc2ccc([N+](=O)[O-])c3nonc23)cc1] | 39.7 | >50 |
| JY-5-195 | 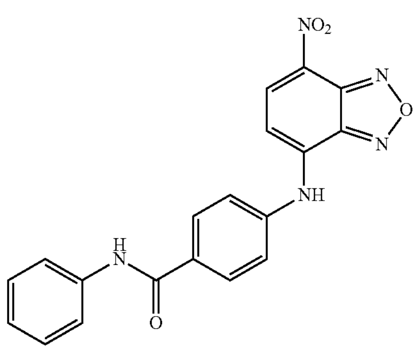 [SMILES: O=C(Nc1ccccc1)c1ccc(Nc2ccc([N+](=O)[O-])c3nonc23)cc1] | 57.9 | >100 |

TABLE 8-continued

Structures and activities of c-Myc-Max dimerization inhibitors.

| Code Number | Structure | IC$_{50}$ Myc-Max[a] (uM) | IC$_{50}$ Max-Max[b] (uM) |
|---|---|---|---|
| JY-5-261 | (structure with NO$_2$, benzofurazan, NH, benzamide, CF$_3$) | 71 | >100 |

[a]Concentration of compounds at which 50% inhibition of c-Myc-Max dimerization and DNA binding was observed in EMSAs
[b]Concentration of compounds at which 50% inhibition of Max-Max dimerization and DNA binding was observed in EMSAs.

TABLE 9

Cell proliferation inhibition data (MTT assay) for c-Myc-Max dimerization Inhibitors.[a]

| Code Number | IC$_{50}$ HL60 (uM) | IC$_{50}$ Daudi (uM) |
|---|---|---|
| 10074-G5 | ~10 | ~30 |
| JY-3-094 | >100 | >100 |
| SF-3-103B | >100 | >100 |
| 3jc53-6 | >100 | >100 |
| 3jc48-3 | 3.50 ± 0.54 | 1.28 ± 0.73 |
| 4jc23-4 | 0.877 ± 0.07 | 0.500 ± 0.025 |
| SF-4-017 | 9.20 ± 0.78 | 2.50 ± 0.05 |
| JY-5-195 | 3.1 ± 0.3 | 5.10 ± 0.56 |
| JY-5-261 | 5.3 ± 0.3 | 3.9 ± 0.4 |

[a]Compounds were tested against logarithmically growing HL60 and Daudi cells in a standard 10-point serial dilution assay with each point being tested in quadruplicate in a standard MTT-based assay.

TABLE 10

Screening Data: % Inhibition of c-Myc-Max Dimerization by 100 μM Small-Molecule as Assessed by an EMSA

| Code Number | % Inhibition of c-Myc-Max Dimerization |
|---|---|
| 10074-G5 | 39 |
| JY-3-094 | 94 |
| Biphenyl B Variants | |
| 3jc42 | 10 |
| 3jc53-1 | 18 |
| 3jc53-2 | 0 |
| 3jc53-3 | 41 |
| 3jc53-4 | 7 |
| 3j53-5 | 16 |
| 3jc53-6 | 16 |
| 3jc53-7 | 44 |
| 3jc53-8 | 23 |
| 3jc53-9 | 13 |
| 3jc53-10 | 34 |
| 3jc53-11 | 0 |
| 3jc53-12 | 2 |
| 3jc53-13 | 0 |
| 3jc53-14 | 4 |
| 3jc53-15 | 6 |
| 4jc23-6 | 0 |
| 3jc48-3 | 94 |
| 4jc23-4 | 74 |
| 3jc62-7 | 0 |
| 3jc62-1 | 0 |
| 3jc62-2 | 0 |
| 3jc62-3 | 0 |
| 3jc62-4 | 0 |
| 3jc62-5 | 8 |
| 3jc62-6 | 25 |

TABLE 11

| Code Number | % Inhibition of c-Myc-Max Dimerization |
|---|---|
| 10074-G5 | 39 |
| JY-3-094 | 94 |
| Benzofurazan Variants | |
| SF-3-068 | 0 |
| SF-3-070 | 5 |
| SF-3-078 | 2 |
| SF-3-079 | 0 |
| SF-3-080 | 0 |
| SF-3-081 | 0 |
| SF-3-083 | 9 |
| SF-3-093A | 0 |
| SF-3-093B | 4 |
| SF-3-098 | 0 |
| SF-3-101 | 0 |
| SF-3-103A | 0 |
| SF-3-103B | 49 |
| SF-3-104A | 0 |
| SF-3-105 | 0 |
| SF-3-106 | 0 |
| SF-3-107 | 0 |

REFERENCES

The contents of all reference cited herein are incorporated by reference herein for all purposes.
[1] C. V. Dang, *Mol. Cell Biol.* 1999, 19, 1-11.
[2] C. E. Nesbit, J. M. Tersak, E. V. Prochownik, *Oncogene* 1999, 18, 3004-3016.

[3] L. M. Boxer, C. V. Dang, *Oncogene* 2001, 20, 5595-5610.
[4] S. Adhikary, M. Eilers, *Nat. Rev. Mol. Cell Biol.* 2005, 6, 635-645.
[5] S. Pelengaris, M. Khan, G. I. Evan, *Nat. Rev. Cancer* 2002, 2, 764-776.
[6] S. K. Nair, S. K. Burley, *Cell* 2003, 112, 193-205.
[7] Hecht, J. L., Aster, J. C., *J. Clin. Oncol.* 2000, 18, 3707-3721.
[8] L. Soucek, J. R. Whitfield, N. M. Sodir, D. Masso-Valles, E. Serrano, A. N. Karnezis, L. B. Swigart, G. I. Evan, *Genes Dev.* 2013, 27, 504-513.
[9] M. D. Delgado, J. Leon, *Genes Cancer* 2010, 1, 605-616.
[10] R. Dalla-Favera, M. Bregni, J. Erikson, D. Patterson, R. C. Gallo, C. M. Croce, *Proc. Natl. Acad. Sci. USA* 1982, 79, 7824-7827.
[11] E. M. Berns, J. G. Klijn, W. L. van Putten, I. L. van Staveren, H. Portengen, J. A. Foekens, *Cancer Res* 1992, 52, 1107-1113.
[12] M. Buchholz, A. Schatz, M. Wagner, P. Michl, T. Linhart, G. Adler, T. M. Gress, V. Ellenrieder, *Embo J.* 2006, 25, 3714-3724.
[13] (a) S. Mitani, H. Kamata, M. Fujiwara, N. Aoki, T. Tango, K. Fukuchi, T. Oka, *Clin. Exp. Med.* 2001, 1, 105-111; (b) U. R. Rapp, C. Korn, F. Ceteci, C. Karreman, K. Luetkenhaus, V. Serafin, E. Zanucco, I. Castro, T. Potapenko, *PLoS One* 2009, 4, e6029.
[14] (a) M. D. Erisman, P. G. Rothberg, R. E. Diehl, C. C. Morse, J. M. Spandorfer, S. M. Astrin, *Mol. Cell. Biol.* 1985, 5, 1969-1976; (b) H. Hermeking, C. Rago, M. Schuhmacher, Q. Li, J. F. Barrett, A. J. Obaya, B. C. O'Connell, M. K. Mateyak, W. Tam, F. Kohlhuber, C. V. Dang, J. M. Sedivy, D. Eick, B. Vogelstein, K. W. Kinzler, *Proc Natl Acad Sci USA* 2000, 97, 2229-2234.
[15] L. Soucek, G. I. Evan, *Curr. Opin. Genet. Dev.* 2010, 20:91.
[16] L. Soucek, J. Whitfield, C. P. Martins, A. J. Finch, D. J. Murphy, N. M. Sodir, A. N. Karnezis, L. B. Swigart, S, Nasi, G. I. Evan, *Nature* 2008, 455, 679-683.
[17] J. E. Delmore, G. C. Issa, M. E. Lemieux, P. B. Rahl, J. Shi, H. M. Jacobs, E. Kastritis, T. Gilpatrick, R. M. Paranal, J. Qi, M. Chesi, A. C. Schinzel, M. R. McKeown, T. P. Heffernan, C. R. Vakoc, P. L. Bergsagel, I. M. Ghobrial, P. G. Richardson, R. A. Young, W. C. Hahn, K. C. Anderson, A. L. Kung, J. E. Bradner, C. S. Mitsiades, *Cell* 2011, 146, 904-917.
[18] C. Y. Lin, J. Loven, P. B. Rahl, R. M. Paranal, C. B. Burge, J. E. Bradner, T. I. Lee, R. A. Young, *Cell* 2012, 151, 56-67.
[19] Z. Nie, G. Hu, G. Wei, K. Cui, A. Yamane, W. Resch, R. Wang, D. R. Green, L. Tessarollo, R. Casellas, K. Zhao, D. Levens, *Cell* 2012, 151, 68-79.
[20] J. L. Yap, J. Chauhan, K.-Y. Jung, L. Chen, E. V. Prochownik, S. Fletcher, *Med. Chem. Commun.* 2012, 3, 541-551.
[21] E. V. Prochownik, P. K. Vogt, *Genes Cancer* 2010, 1, 650-659.
[22] X. Yin, C. Giap, J. S. Lazo, E. V. Prochownik, *Oncogene* 2003, 22, 6151-6159.
[23] H. Wang, D. I. Hammoudeh, A. V. Follis, B. E. Reese, J. S. Lazo, S. J. Metallo, E. V. Prochownik, *Mol. Cancer Ther.* 2007, 6, 2399-2408.
[24] T. Berg, S. B. Cohen, J. Desharnais, C. Sonderegger, D. J. Maslyar, J. Goldberg, D. L. Boger, P. K. Vogt, *Proc. Natl. Acad. Sci. USA* 2002, 99, 3830-3835.
[25] J. Shi, J. S. Strover, L. R. Whitby, P. K. Vogt, D. L. Boger, *Bioorg. Med. Chem. Lett.* 2009, 19, 6038-6041.
[26] Y. Xu, J. Shi, N. Yamamoto, J. A. Moss, P. K. Vogt, K. D. Janda, *Bioorg. Med. Chem.* 2006, 14, 2660-2673.
[27] A. Kiessling, B. Sperl, A. Hollis, D. Eick, T. Berg, *Chem. Biol.* 2006, 13, 745-751.
[28] A. Kiessling, R. Wiesinger, B. Sperl, T. Berg, *ChemMedChem* 2007, 2, 627-630.
[29] P. Filippakopoulos, J. Qi, S. Picaud, Y. Shen, W. B. Smith, O. Fedorov, E. M. Morse, T. Keates, T. T. Hickman, I. Felletar, M. Philpott, S. Munro, M. R. McKeown, Y. Wang, A. L. Christie, N. West, M. J. Cameron, B. Schwartz, T. D. Heightman, N. La Thangue, C. A. French, O. Wiest, A. L. Kung, S. Knapp, J. E. Bradner, *Nature* 2010, 468, 1067-1073.
[30] A. V. Follis, D. I. Hammoudeh, Wang, H. E. V. Prochownik, S. J. Metallo, *Chem. Biol.* 2008, 15, 1149-1155.
[31] D. I. Hammoudeh, A. V. Follis, E. V. Prochownik, S. J. Metallo, *J. Am. Chem. Soc.* 2009, 131, 7390-7401.
[32] J. L. Yap, H. Wang, A. Hu, J. Chauhan, K.-Y. Jung, R. B. Gharavi, E. V. Prochownik, S. Fletcher, *Bioorg. Med. Chem. Lett.* 2013, 23, 370-374.
[33] H. Wang, J. Chauhan, A. Hu, K. Pendleton, J. L. Yap, P. E. Sabato, J. W. Jones, M. Perri, J. Yu, E. Cione, M. A. Kane, S. Fletcher, E. V. Prochownik, *Oncotarget* 2013, 4:936-947.
[34] M. E. Jung, T. A. Dong, X. Cai, *Tetrahedron Lett.* 2011, 52, 2533-2535.
[35] D. M. Clausen, J. Guo, R. A. Parise, J. H. Beumer, M. J. Egorin, J. S. Lazo, E. V. Prochownik, J. L. Eiseman, *J. Pharmacol. Exp. Ther.* 2010, 335, 715-727.
[36] C. M. Park, M. Bruncko, J. Adickes, J. Bauch, H. Ding, A. Kunzer, K. C. Marsh, P. Nimmer, A. R. Shoemaker, X. Song, S. K. Tahir, C. Tse, S. Wang, M. D. Wendt, X. Yang, H. Zhang, S. W. Fesik, S. H. Rosenberg, S. W. Elmore, *J. Med. Chem.* 2008, 51, 6902-6915.
[37] M. Jagodzinska, F. Huguenot, G. Candiani, M. Zanda, *ChemMedChem* 2008, 4, 49-51.
[38] Gardner, L. B.; Lee, L. A.; Dang, C. V. *Encyclopedia of Cancer*, 2$^{nd}$ Ed (Bertino J Eds) pp 555-561, Elsevier Science, Burlington, Mass.
[39]. www.cancer.org
[40] Felsher, D. W.; Bishop, J. M. *Mol. Cell.* 1999, 4, 199-207.
[41] Huang, M. J.; Cheng, Y. C.; Liu, C. R.; Lin, S.; Liu, H. E. *Exp. Hematol.* 2006, 34, 1480-1489.
[42] Mo, H.; Henriksson, M. *Proc. Natl. Acad. Sci. USA* 2006, 103, 6344-6349.
[43] Blackwood, E. M.; Eisenman, R. N. *Science* 1991, 251, 1211-1217.
[44] Prendergast, G. C.; Lawe, D.; Ziff, E. B. *Cell* 1991, 65, 395-407.
[45] Kretzner, L.; Blackwood, E. M.; Eisenman, R. N. *Nature* 1992, 359, 426-429.
[46] Kiessling, A.; Sperl, B.; Hollis, A.; Eick, D.; Berg, T. *Chem. Biol.* 2006, 13, 745-751.
[47] Kiessling, A.; Wiesinger, R.; Sperl, B.; Berg, T. *ChemMedChem*, 2007, 2, 627-630.
[48.] Boger, D. L.; Lee, J. K.; Goldberg, J.; Jin, Q. *J. Org. Chem.* 2000, 65, 1467-1474.
[49] Guo J, Parise R A, Joseph E, Egorin M J, Lazo J S, Prochownik E V, Eiseman J L. *Cancer Chemother. Pharmacol.* 2009, 63, 615-625.
[50] Michel, J.; Cuchillo, R. *PLoS One* 2012, 7, e41070.

That which is claimed is:

1. A compound represented by the formula:

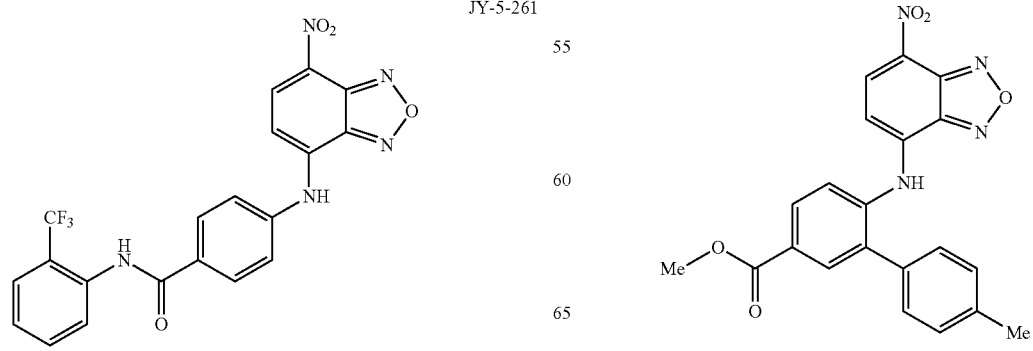

-continued

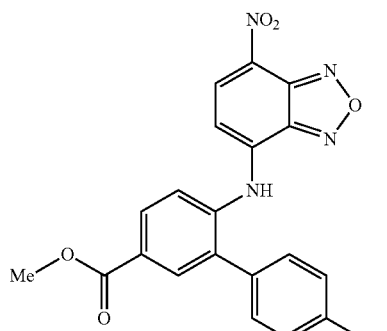
4jc23-4 or a pharmaceutically acceptable salt thereof.

2. A compound having the formula:

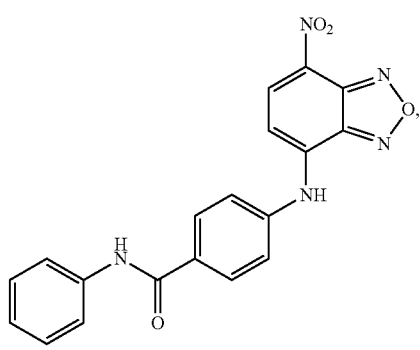
JY-5-195

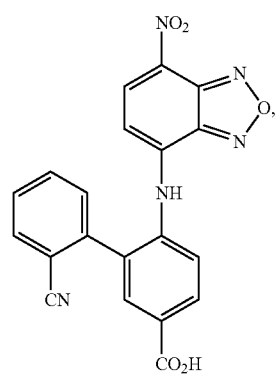
3jc53-7

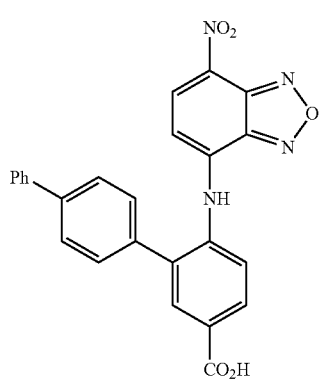
3jc53-3 or a pharmaceutically acceptable salt thereof.

3. A compound having the formula:

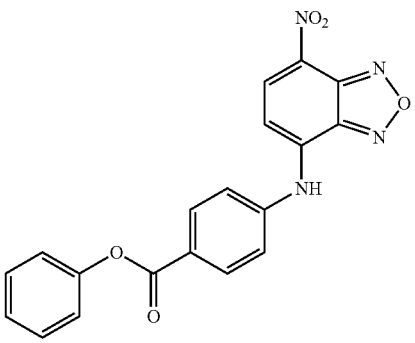
SF-4-017 or a pharmaceutically acceptable salt thereof.

4. The compound of claim 1, wherein the compound is a pharmaceutically acceptable salt of one of an inorganic acid salt, an organic acid salt and a basic salt.

5. A pharmaceutical composition comprising a compound of claim 1, or a pharmaceutically acceptable salt thereof, and a pharmaceutically acceptable excipient.

6. A compound having a formula:

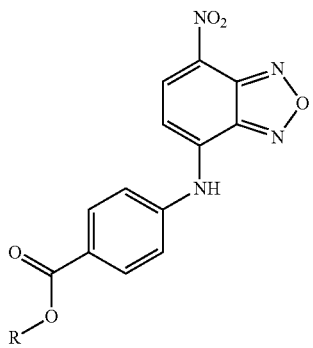

wherein R is Bn, $CH_2O(CO)CH_3$ or $CH_2CF_3$.

7. A compound having a formula:

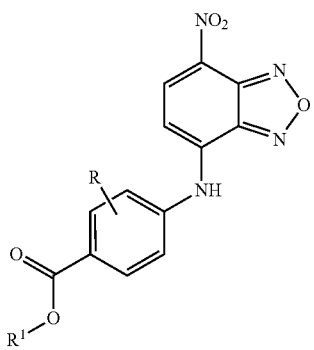

wherein R is alkyl, aryl, heteroaryl, CN, $CO_2H$, $CONH_2$, OH, halogen, $NH_2$ or $NO_2$ and $R^1$ is alkyl, cycloalkyl, $CH_2CF_3$, $CF_2CF_3$ or $CH_2O(CO)CH_3$;

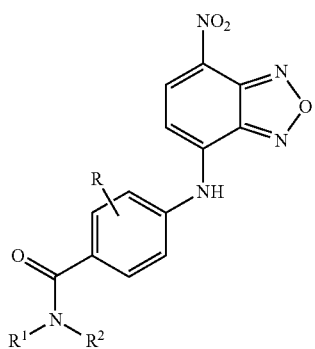

wherein R is alkyl, aryl, heteroaryl, CN, $CO_2H$, $CONH_2$, OH, halogen, $NH_2$ or $NO_2$ and $R^1$ and $R^2$ are independently alkyl, or cycloalkyl;

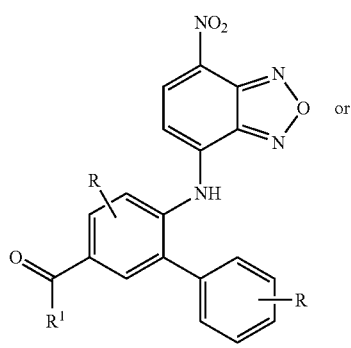 or

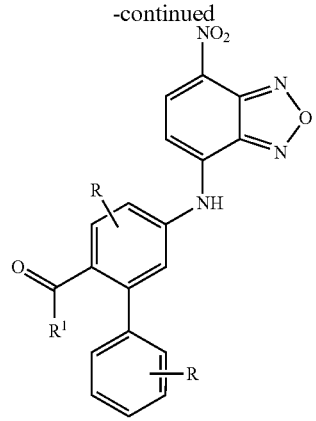

wherein R is H, aryl, heteroaryl, CN, $CO_2H$, $CONH_2$, OH, halogen, $NH_2$, or $NO_2$ and $R^1$ is alkyl $C_1$ to $C_4$ or OH.

8. The compound of claim 2, wherein the compound is a pharmaceutically acceptable salt of one of an inorganic acid salt, an organic acid salt and a basic salt.

9. A pharmaceutical composition comprising a compound of claim 2, or a pharmaceutically acceptable salt thereof, and a pharmaceutically acceptable excipient.

10. The compound of claim 3, wherein the compound is a pharmaceutically acceptable salt of one of an inorganic acid salt, an organic acid salt and a basic salt.

11. A pharmaceutical composition comprising a compound of claim 3, or a pharmaceutically acceptable salt thereof, and a pharmaceutically acceptable excipient.

* * * * *

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Synthetic Construct

<400> SEQUENCE: 1
cacccggtca cgtggcctac ac                                        22

<210> SEQ ID NO 2
<211> LENGTH: 30
<212> TYPE: DNA
<213> ORGANISM: Artificial Sequence
<220> FEATURE:
<223> OTHER INFORMATION: Synthetic Construct

<400> SEQUENCE: 2
tcgagccacg tggccacgtg gccacgtggc                                30

<210> SEQ ID NO 3
<211> LENGTH: 30
<212> TYPE: DNA
<213> ORGANISM: Artificial Sequence
<220> FEATURE:
<223> OTHER INFORMATION: Synthetic Construct

<400> SEQUENCE: 3
tcgagcctcg aggcctcgag gcctcgaggc                                30

<210> SEQ ID NO 4
<211> LENGTH: 38
<212> TYPE: DNA
<213> ORGANISM: Artificial Sequence
<220> FEATURE:
<223> OTHER INFORMATION: Synthetic Construct

<400> SEQUENCE: 4
tcgagggact ttccatggga ctttccatgg gactttcc                       38